United States Patent [19]
Emanuele et al.

[11] Patent Number: 5,674,911
[45] Date of Patent: Oct. 7, 1997

[54] ANTIINFECTIVE POLYOXYPROPYLENE/ POLYOXYETHYLENE COPOLYMERS AND METHODS OF USE

[75] Inventors: R. Martin Emanuele, Alpharetta; Mannarsamy Balasubramanian, Roswell; Hameedsulthan S. Allaudeen, Alpharetta, all of Ga.

[73] Assignee: Cytrx Corporation, Norcross, Ga.

[21] Appl. No.: 468,137

[22] Filed: Jun. 6, 1995

Related U.S. Application Data

[63] Continuation-in-part of Ser. No. 292,803, Aug. 9, 1994, and Ser. No. 457,808, Jun. 1, 1995, which is a continuation of Ser. No. 161,551, Dec. 2, 1993, abandoned, which is a continuation-in-part of Ser. No. 81,006, Jun. 22, 1993, abandoned, which is a continuation of Ser. No. 760,808, Sep. 16, 1991, abandoned, which is a continuation of Ser. No. 419,016, Oct. 10, 1989, abandoned, which is a continuation-in-part of Ser. No. 150,731, Feb. 16, 1988, abandoned, which is a continuation-in-part of Ser. No. 141,668, Jan. 7, 1988, abandoned, which is a continuation of Ser. No. 17,330, Feb. 20, 1987, abandoned, said Ser. No. 292,803, is a continuation-in-part of Ser. No. 87,136, Jul. 2, 1993, which is a continuation of Ser. No. 847,874, Mar. 13, 1992, abandoned, which is a continuation-in-part of Ser. No. 673,289, Mar. 19, 1991, abandoned.

[51] Int. Cl.$^6$ .................. A61K 31/075; C07C 43/11
[52] U.S. Cl. .................................. 514/723; 568/624
[58] Field of Search ........................ 568/624; 514/723

[56] References Cited

U.S. PATENT DOCUMENTS

| | | |
|---|---|---|
| 2,674,619 | 4/1954 | Lundsted. |
| 2,854,378 | 9/1958 | Buckwalter et al.. |
| 2,979,528 | 4/1961 | Lundsted. |
| 3,022,335 | 2/1962 | Lundsted. |
| 3,036,118 | 5/1962 | Jackson et al.. |
| 3,089,818 | 5/1963 | Stone. |
| 3,140,232 | 7/1964 | Noseworthy. |
| 3,228,834 | 1/1966 | Gans et al.. |
| 3,391,196 | 7/1968 | Earing et al.. |
| 3,450,502 | 6/1969 | Hymes. |
| 3,577,522 | 5/1971 | Hymes. |
| 3,590,125 | 6/1971 | Hymes. |
| 3,641,240 | 2/1972 | Hymes et al.. |
| 3,740,421 | 6/1973 | Schmolka. |
| 3,867,521 | 2/1975 | Miskel et al.. |
| 3,867,533 | 2/1975 | Schmolka. |
| 3,956,259 | 5/1976 | Garcia et al.. |
| 3,980,772 | 9/1976 | Ginger et al.. |
| 4,073,886 | 2/1978 | Kehm. |
| 4,100,271 | 7/1978 | Krezanoski. |
| 4,104,455 | 8/1978 | Nagasawa. |
| 4,179,337 | 12/1979 | Davis et al.. |
| 4,186,253 | 1/1980 | Yokoyama et al.. |
| 4,305,922 | 12/1981 | Rhodes. |
| 4,323,560 | 4/1982 | Baschang et al.. |
| 4,395,393 | 7/1983 | Schmolka. |
| 4,407,790 | 10/1983 | Oakes et al.. |
| 4,409,209 | 10/1983 | Baschang et al.. |
| 4,410,660 | 10/1983 | Straus. |
| 4,423,038 | 12/1983 | Baschang et al.. |
| 4,489,158 | 12/1984 | Straus. |
| 4,575,484 | 3/1986 | Straus. |
| 4,600,652 | 7/1986 | Solomon et al.. |
| 4,606,918 | 8/1986 | Allison et al.. |
| 4,609,546 | 9/1986 | Hiratani. |
| 4,764,567 | 8/1988 | Ott. |
| 4,801,452 | 1/1989 | Hunter et al.. |
| 4,837,014 | 6/1989 | Hunter et al.. |
| 4,837,083 | 6/1989 | Hunter et al.. |
| 4,879,109 | 11/1989 | Hunter. |
| 4,897,263 | 1/1990 | Hunter. |
| 4,937,070 | 6/1990 | Hunter. |
| 4,997,644 | 3/1991 | Hunter. |
| 5,017,370 | 5/1991 | Hunter et al.. |
| 5,028,599 | 7/1991 | Hunter. |
| 5,030,448 | 7/1991 | Hunter. |
| 5,032,394 | 7/1991 | Hunter. |
| 5,039,520 | 8/1991 | Hunter. |
| 5,041,288 | 8/1991 | Hunter. |
| 5,047,236 | 9/1991 | Hunter et al.. |
| 5,064,643 | 11/1991 | Hunter et al.. |
| 5,071,649 | 12/1991 | Hunter. |
| 5,078,995 | 1/1992 | Hunter et al.. |
| 5,080,894 | 1/1992 | Hunter et al.. |
| 5,089,260 | 2/1992 | Hunter et al.. |

FOREIGN PATENT DOCUMENTS

| | | |
|---|---|---|
| 0 000 704 | 7/1978 | European Pat. Off.. |
| 0003999 | 9/1979 | European Pat. Off.. |
| 0011237 | 5/1980 | European Pat. Off.. |
| 0 049 422 | 9/1981 | European Pat. Off.. |
| 0 103 290 | 9/1983 | European Pat. Off.. |
| 2081436 | 1/1971 | France. |
| 2708152 | 2/1977 | Germany. |
| 90/07336 | 7/1990 | WIPO. |

OTHER PUBLICATIONS

Schmolka, I., "A Review of Block Polymer Surfactants", *Journal of American Oil Chemists Society*, 54, No. 3, pp. 110–116 (1977).

Rodeheaver, G.T., "Pluronic® F–68: A Promising New Skin Wound Cleanser", *Ann Emerg Med*, 9:11, pp. 572–576 (1980).

Moore, A.R., et al., "Reduction of Splenic Vascular Resistance During Profusion by Pluronic® F–68", *Journal of Surgical Research*, Vo.. 8, pp. 563–566 (1968).

(List continued on next page.)

*Primary Examiner*—Johann Richter
*Assistant Examiner*—John Peabody
*Attorney, Agent, or Firm*—Jones & Askew

[57] ABSTRACT

The present invention comprises novel preparations of polyoxypropylene/polyoxyethylene copolymers which retain the therapeutic activity of the commercial preparations, but substantially reduce the undesirable effects which are inherent in the prior art preparations. Because the preparations of polyoxypropylene/polyoxyethylene copolymers which comprise the present invention are a less polydisperse population of molecules than the prior art polyoxypropylene/polyoxyethylene copolymers, the biological activity of the copolymers is better defined and more predictable and the cardiotoxicity inherent in the native copolymers is substantially reduced.

17 Claims, 33 Drawing Sheets

OTHER PUBLICATIONS

Benner, K.U., et al., "Cold–Induced Platelet Aggregation In Vivo And Its Inhibition By A Nonionic Surface Active Substance", *Thrombosis Research*, vol. 2, pp. 331–342 (1973).

Hymes, A.C., et al., "The Influence Of An Industrial Surfactant Pluronic® F–68, In The Treatment of Hemorrhagic Shock", *Journal of Surgical Research*, vol. 11, pp. 191–197 (1971).

Hoie, J., et al., "Effects of Pluronic® F–68, Poloralkol, On Vascular Resistance in Vivo", *Journal of Surgical Research*, vol. 11, pp. 515–517 (1971).

Grover, F.L., et al., "A nonionic Surfactant And Blood Viscosity", *Arch. Surg.*, vol. 106, pp. 307–310 (1973).

Grover, F.L., et al., "The Effect of Pluronic® F–68 On Circulatory Dynamics And Renal and Carotid Artery Flow During Hemorrhagic Shock", *Journal of Surgical Research*, vol. 17, pp. 30–35 (1974).

Ketchum, L.D., et al., "Experimental Use of Pluronic® F-68 In Microvascular Surgery", *Plastic and Reconstructive Surgery*, vol. 53, pp. 288–292 (1974); Ketchum, L. D., Experimental Use of Pluronic F–68 in Microvascular Surgery, *Plastic Reconstructive Surgery*, vol. 54, p. 478 (October 1974).

Block and Graft Copolymerization, vol. 2, (ed. by R. J. Ceresa, John Wiley & Sons, 1976), "The Applications of Block Copolymer Polyol Surfactants", L. G. Lundsted and I. R. Schmolka; pp. 174–205 and pp. 255–272 (references).

Reindorf, C.A., et al., "Perfluorocarbon Compounds: Effects on the Rheological Properties of Sickle Erythrocytes in vitro", *American Journal of Hematology*, vol. 19, pp. 229–236 (1985).

Padilla, F., et al., "Effect of Fluorocarbon Emulsions on the Mechanical Fragility of Normal and Sickle Cells: In Vitro Studies" Federation Proceedings, vol. 34, pp. 1510–1512 (1975).

Vercellotti, G. M., et al., "Activation of Plasma Complement by Perfluorocarbon Artificial Blood: Probable Mechanism of Adverse Pulmonary Reactions in Treated Patients and Rationale for Corticosteroid Prophylaxis", *Blood*, vol. 59, pp. 1299–1304 (1982).

Janoff, A. S., et al., "The Modification of Human Erythrocyte Membrane Structure by Membrane Stabilizers: An Electron Spin Resonance Study", *American Journal of Hematology*, vol. 10, pp. 171–179 (1981).

Ketchum, L. D., "Pharmacological Alterations in the Clotting Mechanism: Use in Microvascular Surgery", *Journal of Hand Surgery*, vol. 3, pp. 407–415 (1978).

Vasko, K. A., et al., "Poloxalkol® (Pluronic F–68): A Priming Solution for Cardiopulmonary Bypass", *Trans. Am. Soc. Artif. Int. Organs*, 18, 526–531 (1972).

Block, N. L., et al., "Acutely Traumatized Canine Ureter: Effects of Low Molecular Weight Dextran and Surfactant Pluronic F–68", *Urology*, vol. III 190–194 (1974).

Knize, D. M., et al., "Use of Antisludging Agents in Experimental Cold Injuries", *Surgery, Gynecology & Obstetrics*, vol. 129, pp. 1019–1026 (1969).

Organ Perfusion and Preservation, (ed. by Norman, J. C., Appleton–Century–Crofts,)1968), Paton, B.C., et al., "The Use of a Nonionic Detergent Added to Organ Perfusates", pp. 105–120.

Smillie, J. A., et al., "Cryopreservation of Human Platelets with Polyvinylpyrrolidone", *Transfusion*, vol. 21, pp. 552–556 (1981).

Gaehtgens, P., et al., "Disaggregation of Human Red Blood Cells by Various Surface–Active Agents as Related to Changes of Cell Shape and Hemolysis", *Act Heamat.*, vol. 33, pp 82–89 (1975).

Advances in Blood Substitute Research (ed. by Bolin, et al., Alan R. Liss, Inc. New York (1983) Sugi, et al., The Use of Fluosol–DA (FDA) in Emergency Situations: A report of 67 clinical cases, Abstract/451.

Lane, T. A., et al., "Reduction in the Toxicity of a Component of an Artificial Blood Substitute by Supercritical Fluid Fractionation", *Transfusion*, vol. 28, pp. 375–378 (1987).

Lane, T. A., et al., "Paralysis of Phagocyte Migration Due to an Artificial Blood Substitute", *Blood*, vol. 64, pp. 400–405 (1984).

Kanter; K. R., et al., "Superiority of Perfluorocarbon Cardioplegia Over Blood or Crystalloid Cardioplegia", *Circulation*, vol. 64, pp. II–75–II–80 (1981).

Harjula, A., et al., "Perfluorocarbon Solution as a Myocardial Preservative", *J. Applied Cardiology*, vol. 2, pp. 121–136 (1987).

Tokioka, M.D., et al., "Effects of Intracoronary Infusion of Arterial Blood or Fluosol–DA 20% on Regional Myocardial Metabolism and Function During Brief Coronary Artery Occlusions", *Laboratory Investigation*, vol. 75, pp. 473–481 (1987).

Forman, M. B., et al., "Reduction of Infarct Size with Intracoronary Perfluorochemical in a Canine Preparation of Reperfusion", *Circulation*, vol. 71, pp. 1060–1068 (1985).

Forman, M. B., et al., "Beneficial Long–Term Effect of Intracoronary Perfluorochemical on Infarct Size and Ventricular Function in a Canine Reperfusion Model", *J. Am. Col. of Cardiol.*, 1082–1080 (May, 1987).

Goodman, R. L., et al., "Perfluorocarbon Emulsions in Canter Therapy: Preliminary Observations on Presently Available Formulations", *Int. J. Radiation Oncology Biol. Phys.*, vol. 10, pp. 1421–1424 (1984).

Spiess, B. D., et al., "Protection from Cerebral Air Emboli With Pefluorocarbons in Rabbits", *Stroke*, vol. 17, pp. 1146–1149 (1986).

Hunter Robert, "Adjuvant activity of non–ionic block copolymers. IV. Effect of molecular weight and formulation on titre and of isotype antibody", Vaccine, vol. 9, pp. 250–256 (Apr. 1991).

Cornforth et al., "Antituberculosis Effect of Certain Surface––Active Polyoxyethylene Ethers in Mice," Nature, vol. 168, pp. 150–153 (1951).

Lin, T. S. and Prusoff, W. H., "Synthesis and Biological Activity of Several Amio Analogs of Thymidine," *J. Med. Chem.*, vol. 21, pp. 109–112 (1978).

McDougal, J. S., et al., "Immunoassay for the detection and Quantitation of infectious human retrovirus, lymphadenopathy–associated virus (LAV)." *J. Immun. Meth.* vol.76, pp. 171–183 (1985).

Groopman, J. E., et al., "Characterization of serum neutralization response to the human immunodeficiency virus (HIV)," *AIDS Res. Human Retro.*, vol. 3, pp. 71–85 (1987).

Spira, et al. "Micromethod for assaying the reverse transcriptase of LAV– HTLV–III/lymphadenopathy–associated virus." *J. Clin. Microbiol.*, vol. 25, pp. 97–99 (1987).

Schinazi, R.F. et al., "Combinations of Isopfinosine and 3'–Azido–3'–Deoxythymidine in Lymphocytes Infected with Human Immunodeficiency Virus Type 1," *Antimicrob. Agents Chemother.* vol. 32, pg. 1784–1789 (1988).

Schinazi, R.F. et al., "Effect of combination of acyclovir, and vidarabine or its 5'-monophosphate on herpes simplex viruses in cell culture and in mice," *Antimicrob. Agents Chemother.* vol. 22, pp. 499–507 (1982).

Chou, T. C., and Talalay, P. "Quantitatuve analysis of dose–effect relationships: the combined effects of multiple drugs or enzyme inhibitors," *Adv. Enz.Regul.*, vol. 22, pg. 27–55 (1984).

Weintraub, Harold M., "Antisense RNA and DNA," *Scientific American*, pp. 40–46 (Jan. 1990).

Schmolka, I.R. et al., "Artificial Skin I. Preparation and Properties of Pluronic F–127 Gels for Treatment of Burns," *J. Biomed. Mater. Res.*, vol. 6, pp. 571–582 (1972).

Snippe, H. et al., "Adjuvant Effect of Nonionic Block Polymer Surfactants in Humoral and Cellular Immunity," *Int. Archs Allergy appl. Immun.* vol. 65, pp. 390–398 (1981).

Takayama, K. et al.. "Adjuvant activity of non–ionic block copolymers. V. Modulation of antibody isotype by lipopolysaccharides, lipid A and precursors," *Vaccine*, vol. 9, pp. 257–265 (Apr. 1991).

Williams, J.H. et al., "Modulation of Rat Granulocyte Traffic by a Surface Active Agent in Vitro and Bleomycin Injury," *Proceedings of the Society for Experimental Biology and Medicine*, vol. 188, pp. 461–470 (1988).

Matsukura, M. et al., "Phosphorothioate analogs of oligodeoxynucleotides: Inhibitors of replication and cytopathic effects of human immunodeficiency virus," *Proc. Natl. Acad. Sci.*, vol. 84, pg. 7706–7710 (Nov. 1987).

Rodeheavier et al, "Mechanical Cleansing of Contaminated Wounds with Surfactant," *Am. J. Surg.*, vol. 129, No. 3, pp. 241–245 (1975).

Database WPI, Derwent Publications Ltd., London, GB; AN 82–14781E(08) & JP-A-57 008 223 (mitsui Petrochem.) 17 Jan. 1982. *abstract only*.

Schick, M.J., *Non–ionic Surfactants*, Marcel Dekker Inc., New York, pp. 893–920 (1967).

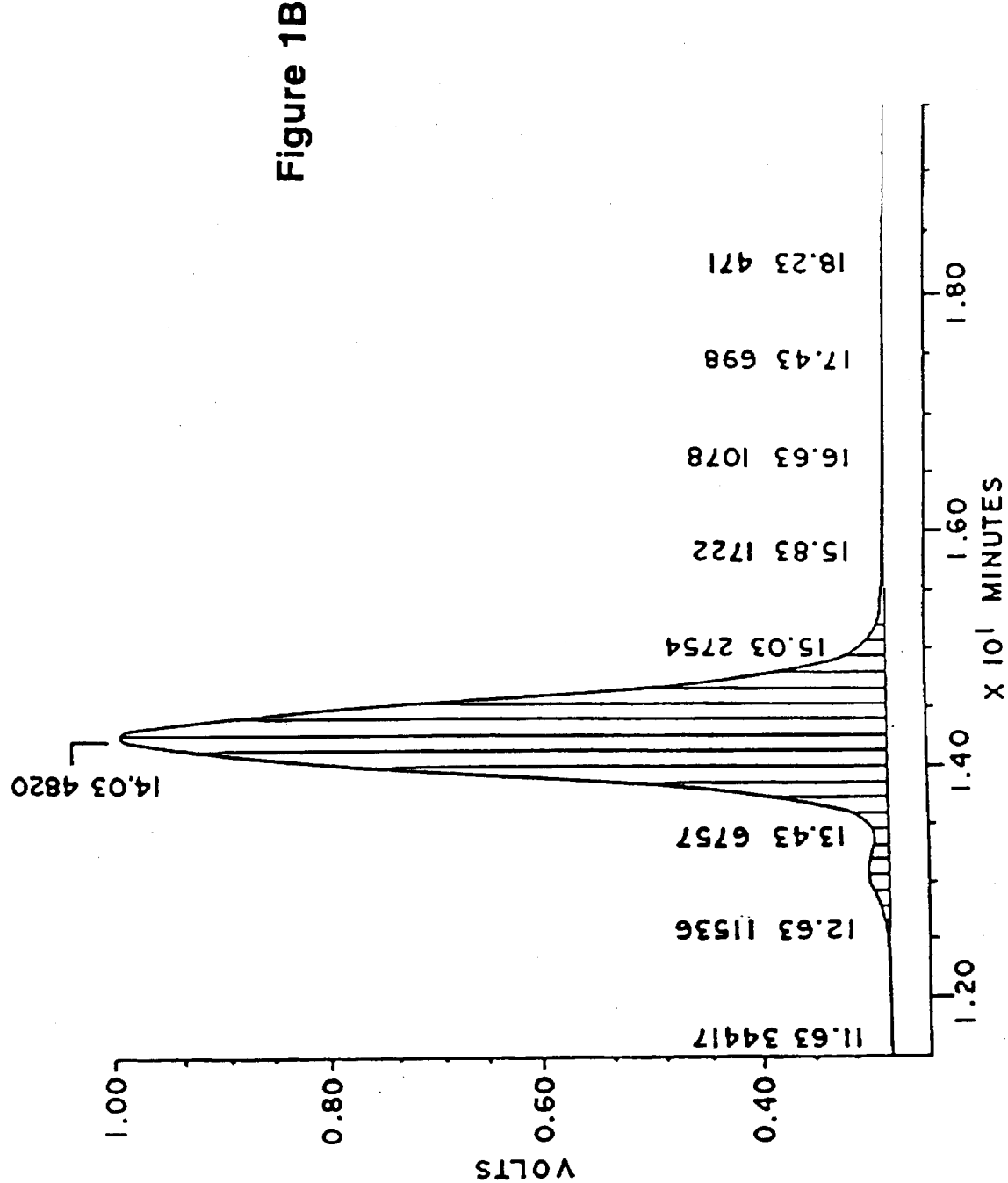

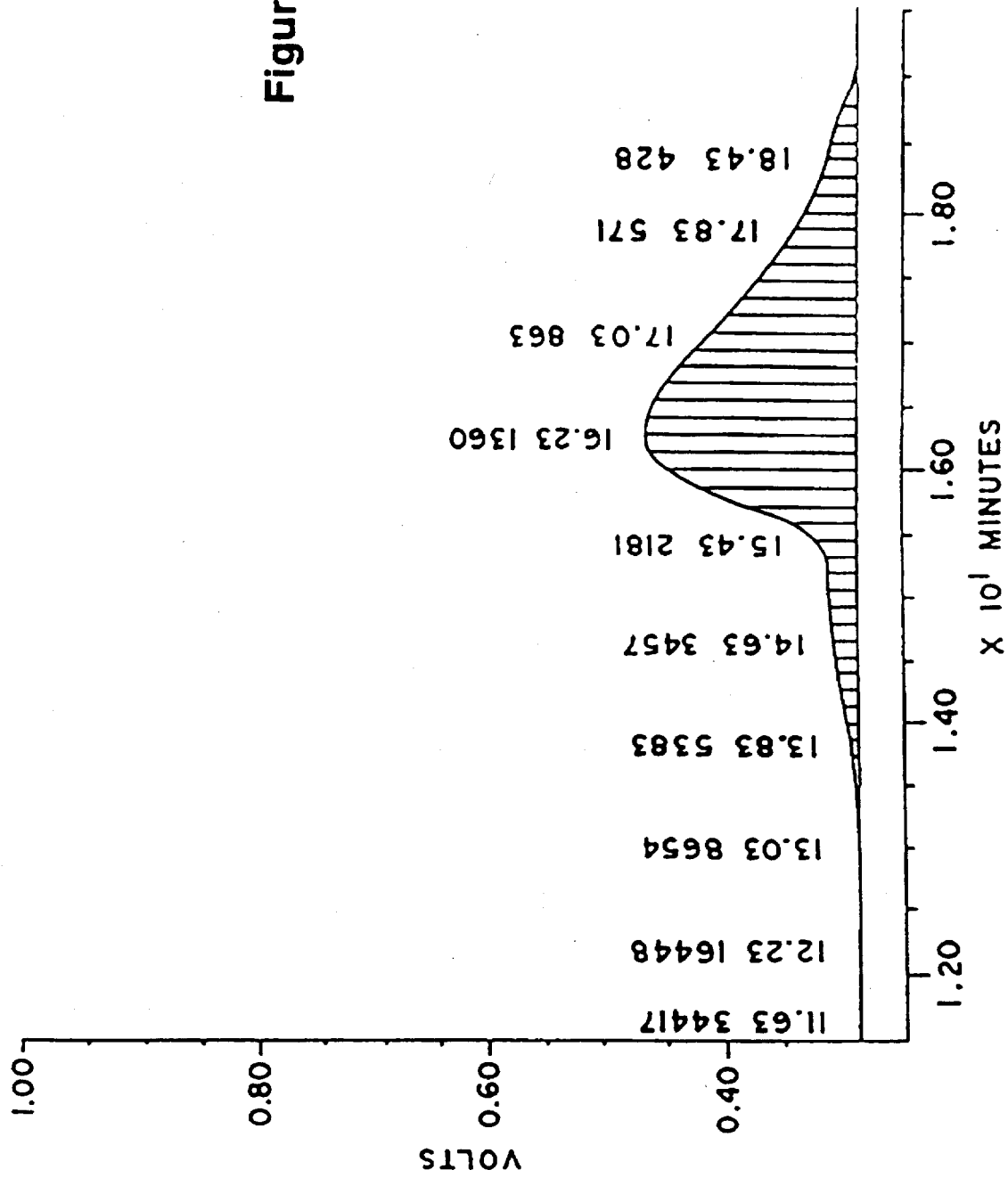

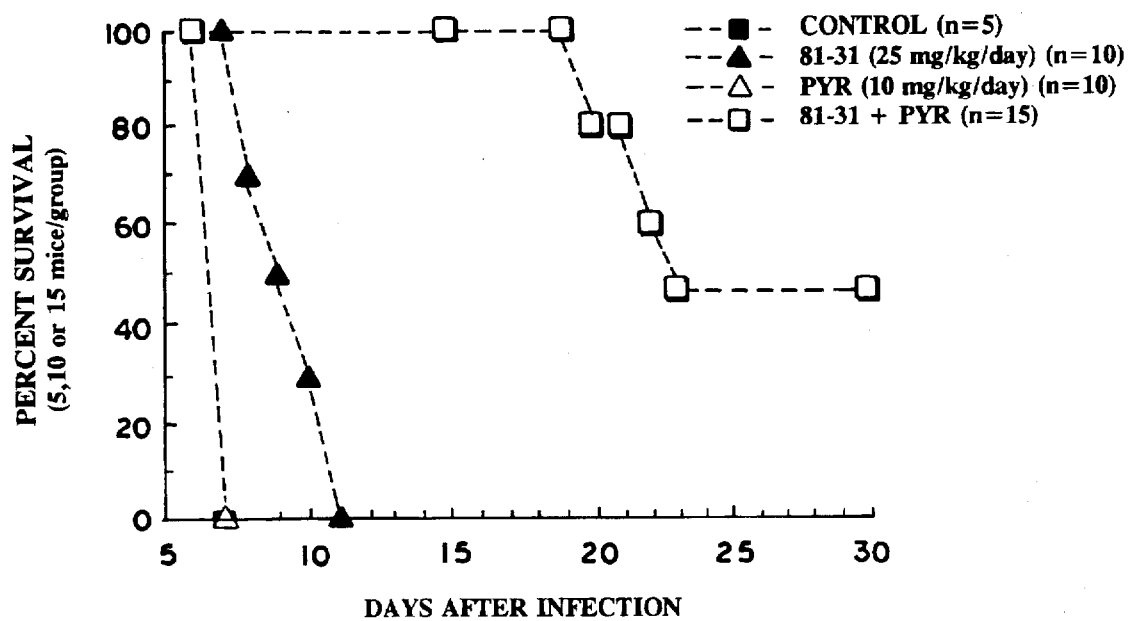
Fig_25
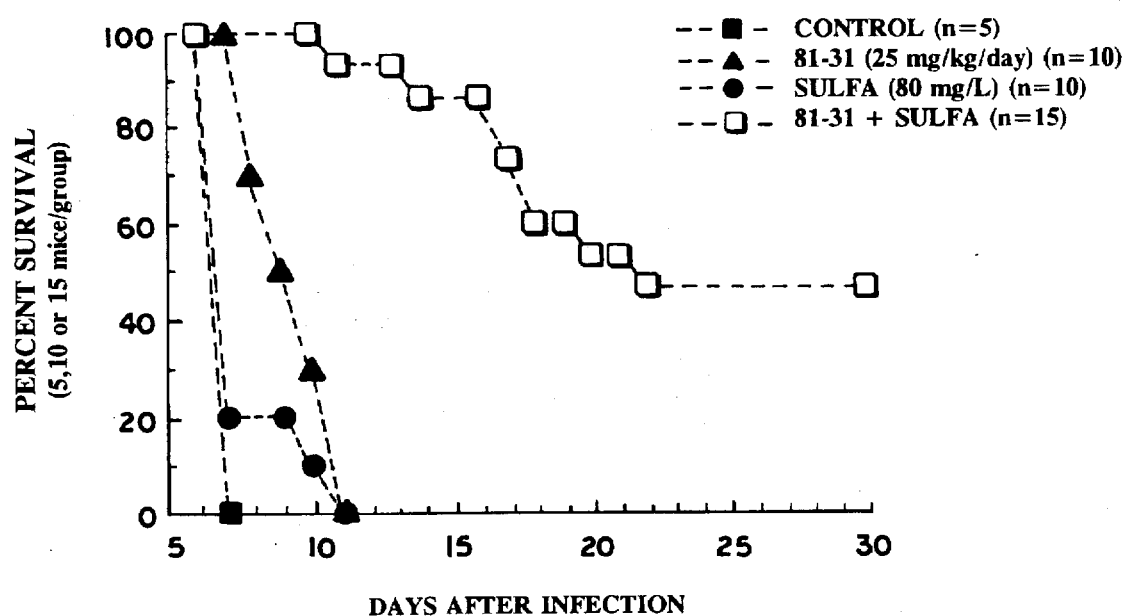
Fig_26

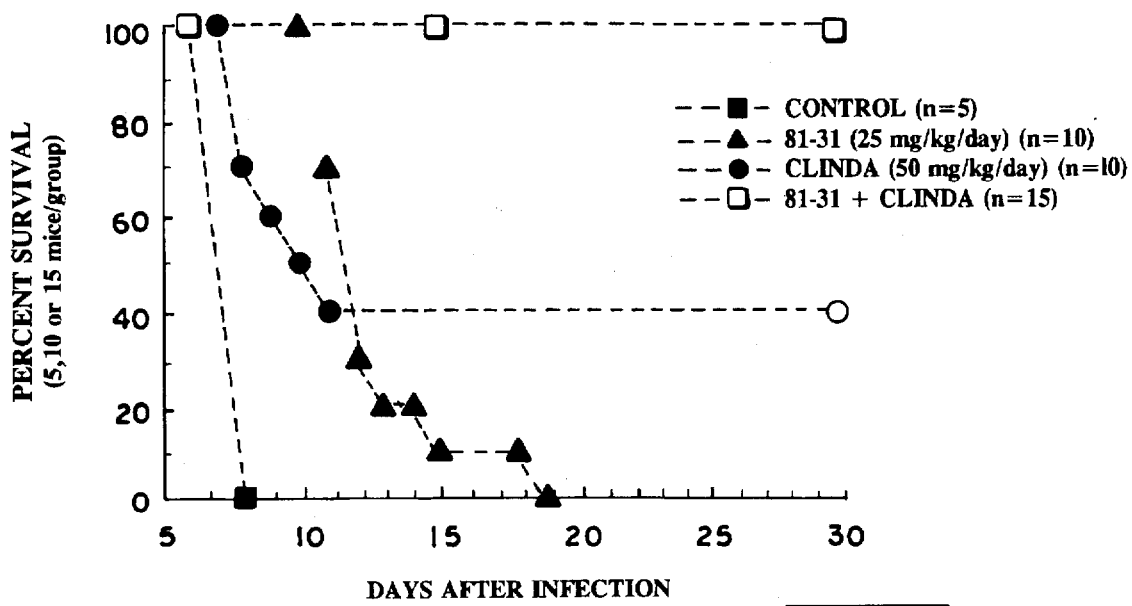
Fig_27
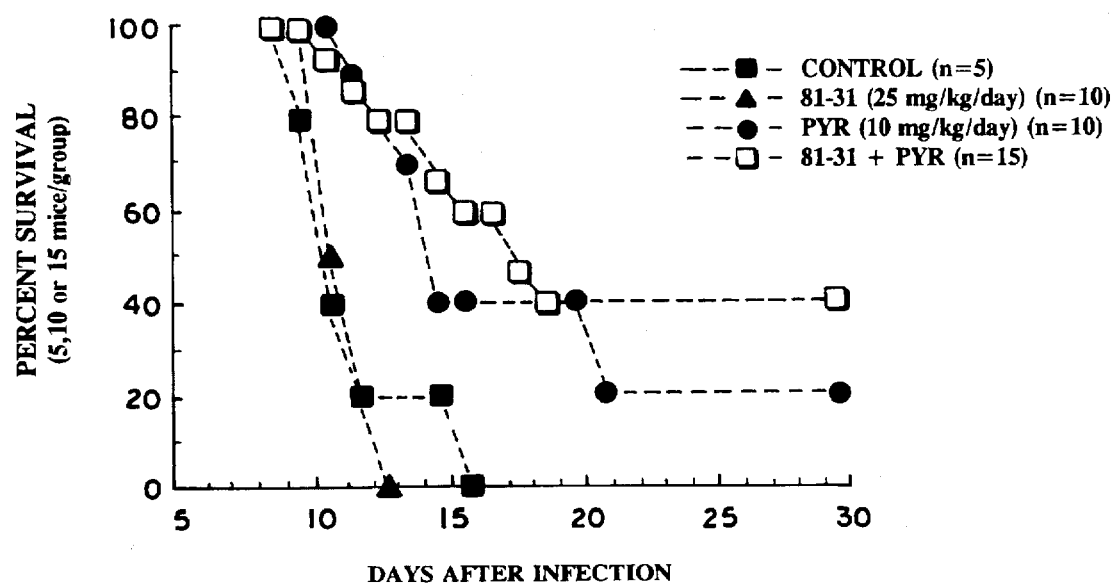
Fig_28

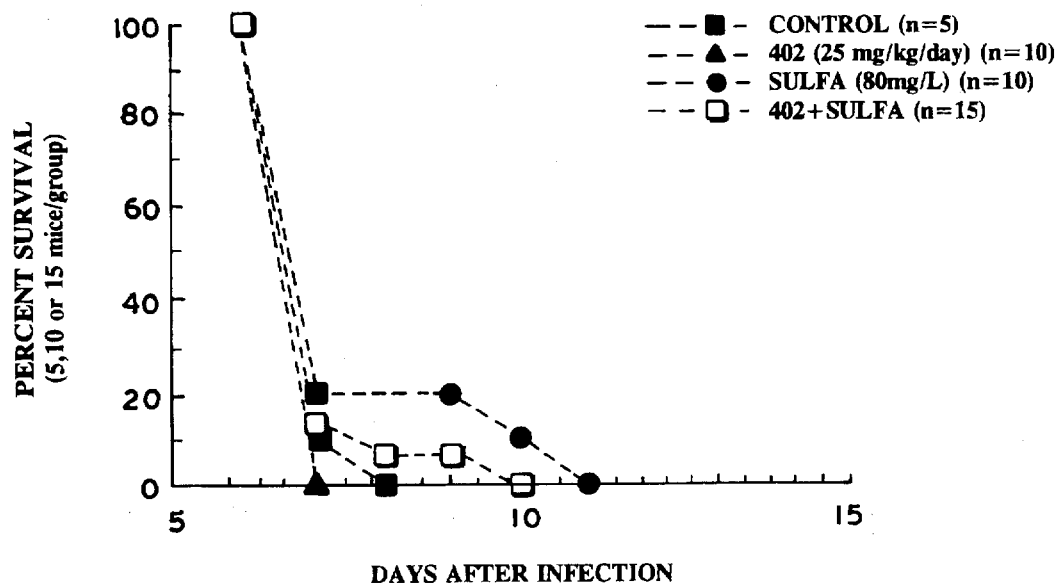
Fig_31
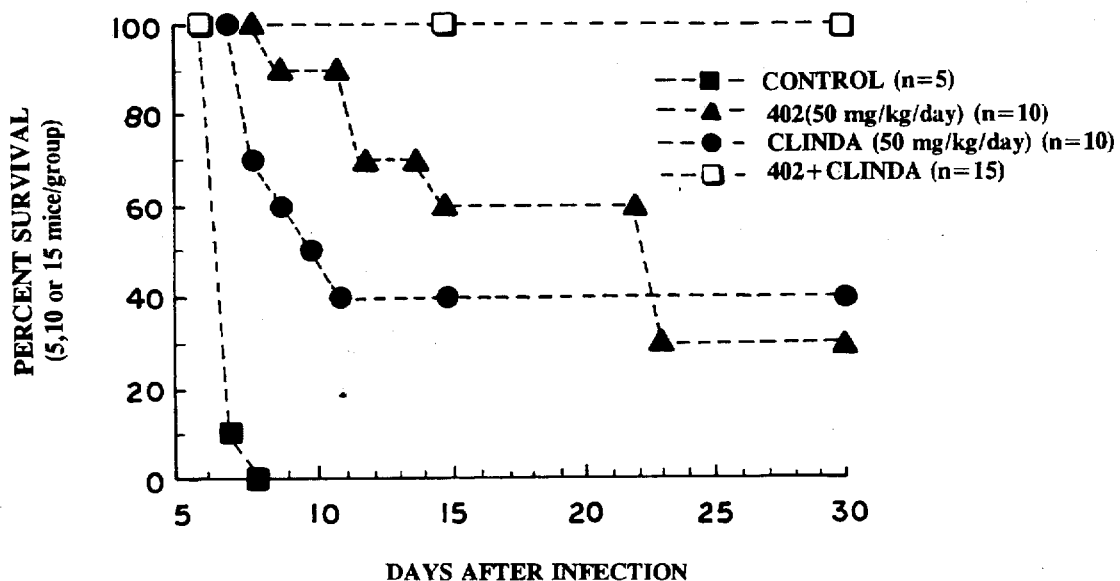
Fig_32

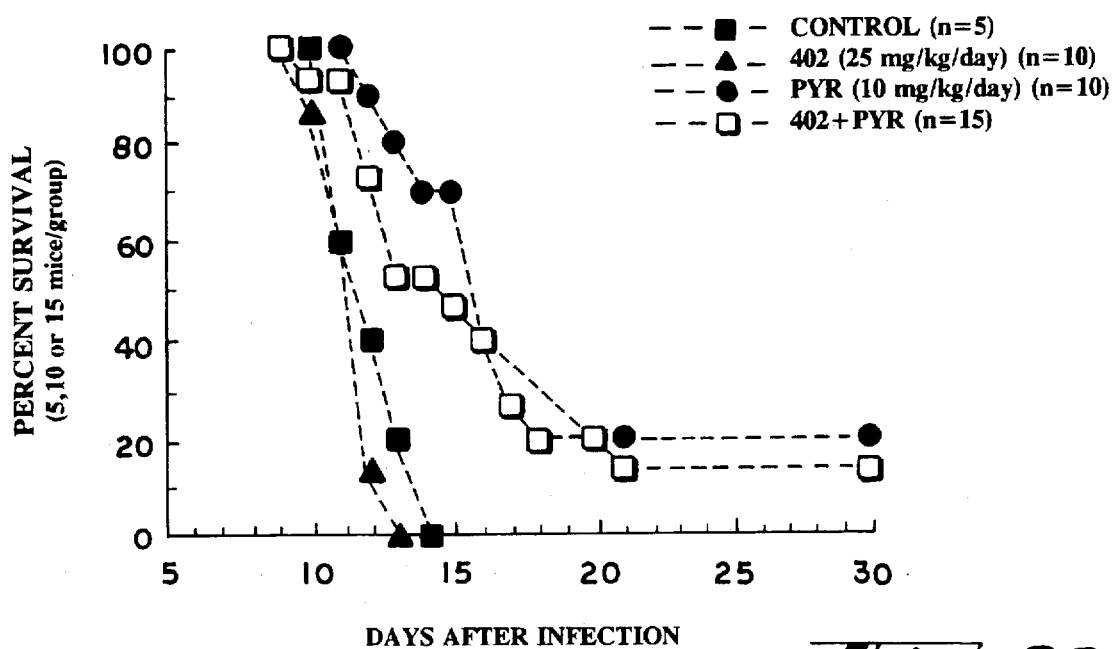
Fig_33
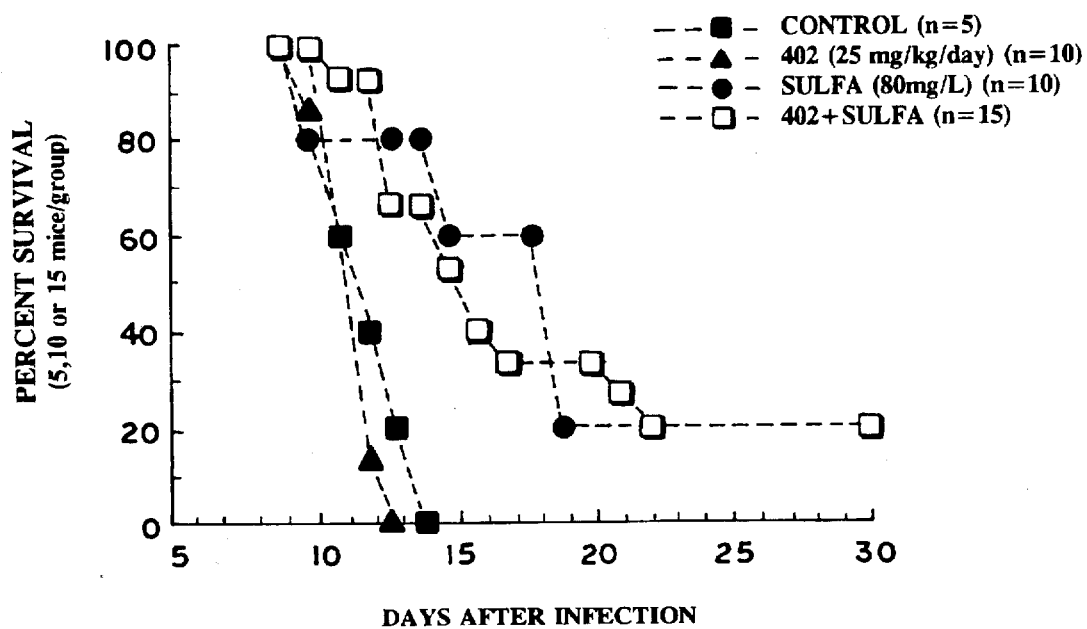
Fig_34

ANTIINFECTIVE POLYOXYPROPYLENE/ POLYOXYETHYLENE COPOLYMERS AND METHODS OF USE

CROSS-REFERENCE TO RELATED APPLICATIONS

This patent application is a continuation-in-part of pending U.S. patent application Ser. No. 08/292,803, filed on Aug. 9, 1994, which is a continuation-in-part of pending U.S. patent application Ser. No. 08/087,136, filed on Jul. 2, 1993, allowed, which is a continuation of U.S. patent application Ser. No. 07/847,874, filed on Mar. 13, 1992, now abandoned, which is a continuation-in-part of U.S. patent application Ser. No. 07/673,289, filed Mar. 19, 1991, now abandoned.

This application is also a continuation-in-part of related U.S. patent application Ser. No. 08/457,808 filed Jun. 1, 1995 which is a file wrapper continuation of U.S. patent application Ser. No. 08/161,551, filed on Dec. 2, 1993, now abandoned which is a continuation-in-part of U.S. patent application Ser. No. 08/081,006, filed Jun. 22, 1993, now abandoned, which is a continuation of U.S. patent application Ser. No. 07/760,808 filed Sep. 16, 1991, now abandoned, which is a continuation of U.S. patent application Ser. No. 07/419,016 filed Oct. 10, 1989, now abandoned, which is a continuation-in-part application of U.S. patent application Ser. No. 07/150,731 filed on Feb. 16, 1988, now abandoned, which is a continuation-in-part of U.S. patent application Ser. No. 07/141,668 filed on Jan. 7, 1988, now abandoned, which is a continuation of U.S. patent application Ser. No. 07/017,330, filed on Feb. 20, 1987, now abandoned.

All of the above-mentioned prior-related patent applications are hereby incorporated by reference in their entirety.

TECHNICAL FIELD

The present invention relates to antiinfective compounds and more particularly to compounds and methods that kill or suppress the growth of intracellular pathogens such as bacteria, viruses, fungi and protozoa. The compounds and methods of the present invention are effective in treating infections caused by intracellular pathogens. The present invention relates to a preparation of polyoxypropylene/polyoxyethylene copolymer which has an improved activity and toxicity profile. The compounds of the present invention include purified polyoxypropylene/polyoxyethylene block copolymers with substantially no unsaturation, substantially free of low molecular weight molecules and a narrowed polydispersity value.

BACKGROUND OF THE INVENTION

Certain polyoxypropylene/polyoxyethylene copolymers have been found to have beneficial biological effects when administered to a human or animal. A group of polyoxypropylene/polyoxyethylene copolymers have been found to inhibit the growth of microoorgansims, such as bacteria, yeasts and viruses. For example, these surface-active copolymers have been shown to inhibit human immunodeficiency virus (HIV), *Mycobacteria species* and *Toxoplasma gondii*.

The antiinfective activity of the surface active copolymers and the use of the surface active copolymers as therapeutic delivery agents are described in detail in copending U.S. patent applications Ser. Nos. 08/161,551 and 08/138,271 both of which are incorporated herein by reference.

Tuberculosis has been a major killing disease of mankind for most of recorded history. The incidence of the disease declined in parallel with advancing standards of living since at least the mid-nineteenth century. However, in spite of the efforts of numerous health organizations worldwide, the eradication of tuberculosis (TB) has never been achieved, nor is it imminent. Nearly half of the world's population is infected with *M. tuberculosis*, with approximately 8 million new cases and there million deaths attributable to TB yearly.

After decades of decline, TB is on the rise, even in the United States where up to 10 million individuals are believed to be infected. Almost 28,000 new cases were reported in 1990, a 9.4 percent increase over 1989. A sixteen percent increase was observed from 1985 to 1990. TB is acquired by the respiratory route; actively infected individuals spread this infection efficiently by coughing or sneezing "droplet nuclei" which contain viable bacilli. Overcrowded living conditions and shared air spaces are especially conducive to the spread of TB, underlying the increase in instances that have been observed in the U.S. in prison inmates and among the homeless in larger cities.

Alarmingly, outbreaks of TB cases resistant to at least two of the most effective anti-TB drugs (rifampin [RFP] and isoniazide [INH]) are being reported in hospitals and correctional facilities with evidence of transmission to human immunodeficiency virus (HIV) negative individuals. Approximately half the patients with acquired immune deficiency syndrome (AIDS) will acquire a mycobacterial infection, with TB being an especially devastating complication. AIDS patients are at higher risks of developing clinical TB and anti-TB treatment seems to be less effective. Consequently, the infection often progresses to a fatal disseminated disease.

Presently an extremely disturbing phenomenon is the emergence of drug resistant *M. tuberculosis*. The rate of new TB cases proven resistant to at least one standard drug increased from 10 percent in the early 1980's to 23 percent in 1991. Currently, seven percent of all cases of TB are resistant to at least one drug, over double the number from the early 1980.

Additionally, mycobacterial other than *M. tuberculosis* are also becoming increasingly problematic as elements in the list of opportunistic infections that plague the AIDS patient. Organisms from the *Avium-intracellulare* complex (MAC), especially sero types four and eight, account for 68% of the mycobacterial isolates from AIDS patients. Enormous numbers of MAC are found (up to $10^{10}$ acid-fast bacilli per gram of tissue) and, consequently the prognosis for the infected AIDS patient is poor.

Mycobacteria, including *Mycobacterium avium*, are intracellular parasites that are capable of growth within cells in the host such as macrophages. The mycobacteria grow slowly, produce no endotoxin and are not motile. They multiply within the macrophages, kill the macrophage and are taken up by new macrophages to start the process over. Host resistance depends upon activation of the macrophages. Activated macrophages are able to kill the bacteria that reside within the cell. This activation depends upon specific T-cells which are produced as the result of a cell mediated immune reaction against proteins of the mycobacteria. Mycobacterial infections have been likened to a war of attrition in which there is a delicate balance between the ability of the mycobacteria to survive within the macrophages and the ability of the host to activate macrophages sufficiently to kill them. In the absence of rapidly acting antiinfective compounds, the goal of therapy is to tip the balance in favor of the host.

There is still no clear understanding of the factors which contribute to the virulence of mycobacteria. Many investigators have implicated lipids of the cell wall and bacterial surface as contributors to colony morphology and virulence. Evidence suggests that C-mycosides, on the surface of certain mycobacterial cells, are important in facilitating survival of the organism within macrophages. Trehalose 6,6' dimycolate, a cord factor, has been implicated for other mycobacteria.

*Mycobacterium avium* bacilli occur in several distinct colony forms. Bacilli which grow as transparent or rough colonies on conventional laboratory media are able to multiply within macrophages in tissue culture, are virulent when injected into susceptible mice, and are resistant to antibiotics. Rough or transparent bacilli which are maintained on laboratory culture media often spontaneously assume an opaque colony morphology at which time they fail to grow in macrophages, are avirulent in mice, and are highly susceptible to antibiotics. The differences in colony morphology between the transparent, rough and opaque strains of *Mycobacterium avium* are almost certainly due to the presence of a glycolipid coating on the surface of transparent and rough organisms which acts as a protective capsule. This capsule, or coating, is composed primarily of C-mycosides which apparently shield the virulent *Mycobacterium avium* organisms from lysosomal enzymes and antibiotics. By contrast, the non-virulent opaque forms of *Mycobacterium avium* have very little C-mycoside on their surface. Both resistance to antibiotics and resistance to killing by macrophages have been attributed to the glycolipid barrier on the surface of *Mycobacterium avium*.

Fatty acids have been shown to exert either an inhibitory or enhancing effect on mycobacterial growth depending on the length of the carbon chain, the degree of saturation, and the presence and type of hydrophilic groups. The mechanism of the growth inhibition effect of fatty acids is not understood, but they are known to be surface-active agents which can interact with glycolipids on the surface of the mycobacteria.

Cornforth et al. ("Antituberculosis Effect of Certain Surface-Active Polyoxyethylene Ethers in Mice." *Nature*, 168; 150–153,1951) reported that certain nonionic surface active agents have antituberculosis effects in mice. Effective materials were arylalkyl polyether ethoxylates, Triton WR1339 and Triton A20. These agents are polymerized forms of familiar Triton surfactants. Mice injected intravenously with 15–25 milligrams of the material were protected from lethal challenge with virulent *Mycobacterium tuberculosis* organisms. The material could be injected before, or up to five days after injection of the organisms with mycobacteria. The untreated animals died within three weeks after injection. Over 80% of the treated animals survived at least three weeks with evidence of only minimal tuberculosis lesions.

Triton WR1339 and Triton A20 are mixtures of numerous similar compounds and are generally toxic. Cornforth and his colleagues synthesized a number of similar materials having greater purity, and found that the antituberculosis effect increased with the molecular weight of the hydrophobic portion of the molecules. The most effective pure preparation had four alkylphenol groups attached in a ring configuration. The size of the hydrophilic moiety was also important. Preparations with an average of 15 to 20 polyoxyethylene (POE) moieties per phenolic group were most effective in treating tuberculosis. However, increasing the number of POE moieties to 60 produced a compound which caused infection to progress more rapidly than untreated controls.

Numerous studies were performed to evaluate the mechanisms of the tuberculosis and antituberculosis effects of these compounds. The antituberculosis compounds were found to impede the growth of virulent tuberculosis bacteria in intact animals and in macrophages in tissue culture. However, they had no effect on the growth of the organisms in bacterial culture. Consequently, the agents affected either the host or the host-parasite interactions, but had no direct effect on mycobacteria. The bulk of evidence suggested that the tuberculosis and antituberculosis effects were due to modification of surface lipids of the mycobacteria.

The purified Cornforth compounds were not developed commercially as antimycobacterial agents. The reasons for this decision are not known, but several factors may have contributed. First, none of the preparations were pure. Second, the compounds suppressed the growth of mycobacteria in animals but did not produce cures. Finally, the compounds were found to be significantly toxic, producing disorders such as necrosis of the liver.

It is known that nonionic surfactants, in general, are much less toxic than either anionic or cationic surfactants. The nonionic block copolymers are among the least toxic of known surfactants. Nonionic block copolymer surfactants can be synthesized in forms which span virtually the entire range of physical chemical activities of known nonionic surface active agents. Wetting agents with properties reminiscent of Cornforth's antituberculosis agents can be produced in many molecular configurations. They can be produced in a higher molecular weight and in a purer form than is practically feasible with most other surfactants. Problems with toxicity of inactive contaminants can be minimized. The known effects of the block copolymers on serum lipids suggest that the block copolymers have biologic activities similar to those of the agents studied by Cornforth with less toxic effects.

Consequently, there is an immediate and increasing need for a new, safe and effective compound that will have an appropriate effect on mycobacteria organisms present in macrophages which does not exhibit excessive toxicity.

Acquired Immune Deficiency Syndrome, or AIDS, is a disease thought to be caused by a human retrovirus, the Human T Lymphotropic Virus III (HTLV-III) which is also called human immunodeficiency virus or HIV. Like other retroviruses, HIV has ribonucleic acid, or RNA, as its genetic material. When the virus enters the host cell, a viral enzyme called reverse transcriptase exploits the viral RNA as a template to assemble a corresponding molecule of DNA. The DNA travels through the cell nucleus and inserts itself among the host chromosomes, where it provides the basis for viral replication.

In the case of HIV, the host cell is often a T4 lymphocyte, a white blood cell that has a central and regulatory role in the immune system. Once it is inside a T4 cell, the virus may remain latent until the lymphocyte is immunologically stimulated by a secondary infection. Then the virus reproducing itself rapidly killing or rendering ineffective the host cell. The resulting depletion of the T4 cells, and loss of activity leaves the patient vulnerable to "opportunistic" infections by an agent that would not normally harm a healthy person. The virus damages the host by many other mechanisms as well.

Many therapies against AIDS infection that are currently being investigated. Several of these therapies under investigation are based on interrupting the reverse transcriptase as it assembles the viral DNA destined to become the virus. The drugs used for this purpose are chemical analogs of the nucleic acids that form the subunits of DNA. When the analog is supplied to an infected cell, reverse transcriptase will incorporate it into a growing DNA chain. Because the analog lacks the correct attachment point for the next subunit, however, the chain is terminated. The truncated DNA cannot integrate itself into the host chromosomes or provide the basis for viral replication, and so the spread of the infection is halted. One of the compounds that is thought to act by mimicking a nucleotide is azidothymidine, or AZT. However, AZT is known to have serious side effects and its efficacy in mitigating the AIDS disease has been questioned. The macrophage is now known to be an additional reservoir of the AIDS virus in the body.

Consequently, there is an immediate need for a compound that will suppress or halt the replication and infection of cells by the viruses such as the HIV virus. There is also a need for a compound with antiviral activity which can localize in macrophages. Further, what is needed is a composition that not only has an cidal effect on a wide variety of microorganisms, but can also facilitate the delivery of drugs or other agents into the cell.

The surface-active copolymers are effective in treating a viral infection in a human or animal including infections caused by the HIV or related viruses. The present invention provides a composition that can be administered to patients who are infected with HIV or similar viruses. The surface-active copolymer is effective in inhibiting or suppressing the replication of the HIV and related virus strains in cells.

The surface-active copolymers are useful for treating infections caused by microorganisms when used alone or with a conventional antibiotic. Several conventional antibiotics that can be used with the surface-active copolymer include, but are not limited to, rifampin, isoniazid, ethambutol, gentamicin, clindamycin, pyrimethamine, tetracycline, and erythromycin.

The surface active copolymers can be used to deliver therapeutic drugs to a human or animal for treating disease states such as, but not limited to, bacterial infection and infections caused by HIV and other DNA and RNA viruses. The methods relate particularly to compositions and methods for treating infectious diseases and genetic disorders through gene therapy and intracellular delivery of antisense oligonucleotides or other nucleic acid sequences.

The surface active copolymers are effective for treating a disease state comprising an administerable admixture of an effective amount of a therapeutic compound capable of altering nucleic acid sequence function and an effective amount of the surface active nonionic block copolymer The surface active copolymers can be used in an admixture of a compound capable of altering gene expression and/or protein translation, such as an antisense oligonucleotide, a triplex DNA compound, a ribozyme or other compound capable of altering nucleic acid sequence function, and the surface active copolymer.

Because the commercially available sources of the polyoxypropylene/polyoxyethylene copolymers have been reported to contain components that exhibit toxicity as well as variation in biological activity, what is needed is a preparation of polyoxypropylene/polyoxyethylene copolymers which retain the therapeutic activities of the commercial preparations but are free from their other biological activities such as toxicity. It is well known in the art that the unsaturation is produced during the polymerization of the polypropylene hydrophobe and unsaturation results in reduced functonality and reduced stability. The reduced functionality results in the formation of impurities with diblock type structure upon subsequent polymerization of the hydrophobe with ethylene oxide. Therefore what is needed is a composition with less unsaturation and less diblock type impurities. In addition, what is needed is a preparation of polyoxypropylene/polyoxyethylene copolymers which is less polydisperse in molecular weight, more stable, is less cardiotoxic, and is more efficacious.

SUMMARY OF THE INVENTION

In accordance with the present invention, a composition and method is provided that is effective in treating infections caused by intracellular pathogens and microorganisms such as bacteria, fungi, viruses, and protozoa. The present invention is effective in inhibiting the growth of microorganisms such as the protozoa *Toxoplasma gondii; Trypanosoma cruzi, Leishmania donovani*, malarial plasmodia; fungi such as *Cryptococcus neoformans*, yeast forms of *Histoplasma capsulatum* and *Candida albicans*; bacteria such as *Mycobacterium species* including, but not limited to, *Mycobacterium avium-intracellulare* complex, and *M. tuberculosis*; and also infections due to HIV and human herpes viruses.

The present invention comprises novel preparations of polyoxypropylene/polyoxyethylene copolymers which are effective as antiinfective agents, but are free from the undesirable effects, such as cardiotoxicity, which are inherent in the prior art preparations. The polyoxypropylene/polyoxyethylene copolymers which comprise the present invention (1) are a less polydisperse population of molecules which results in better and more predictable pharmacologic activity, (2) is comprised of a population of molecules that are less cardiotoxic compared to the copolymers of the prior art, (3) are substantially free of unsaturated molecules and low molecular weight by products. The polyoxypropylene/polyoxyethylene copolymers have greater product stability and shelf life than the poyoxyethylene/polyoxypropylene copolymers of the prior art.

The antiinfective composition of the present invention comprises a surface active copolymer. The surface active copolymer can be an ethylene oxide-propylene oxide condensation product with the following general formula:

wherein "a" is an integer such that the polypropyleneoxide hydrophobe represented by ($C_3H_6O$) has a molecular weight of approximately 1,200 to approximately 15,000, preferably between approximately 1,500 and approximately 5300, more preferably between approximately 1750 Daltons and approximately 4500 Daltons, still more preferably between approximately 2250 Daltons to approximately 4000 Daltons, and "b" is an integer such that the polyethyleneoxide hydrophile portion represented by ($C_2H_4O$) constitutes approximately 1% to approximately 50% by weight of the copolymer compound, preferably approximately 5% to approximately 45% by weight of the copolymer compound, more preferably approximately 10% to approximately 30%, and still more preferably approximately 15% to approximately 20%. The copolymer of the present invention has a polydispersity value of less than approximately 1.17.

The present invention includes polyoxypropylene/polyoxyethylene block copolymers with polydispersity values of less than 1.17. Commercially available poloxamers, for example poloxamer 331, has a polydispersity value as high as approximately 1.41. The purification of the polyoxypropylene polymer can be performed by gel permeation chromatography or other procedures that are well known to those of ordinary skill in the art. The present invention also includes a novel separation process of supercritical fluid extraction using carbon dioxide to purify polyoxypropylene/polyoxyethylene block copolymers to reduce the polydispersity values less than 1.17. In addition, the present invention incudes poyoxyethylene/polyoxypropylene copolymers with polydispersity values less than 1.17 that have been synthesized by a process described in copending patent application Ser. No. 08/292,814.

Accordingly, it is an object of the present invention to provide a surface-active copolymer with antiinfective activities with substantially no unsaturation, with fewer toxic side effects and with substantially no low molecular weight impurities, including diblock type impurities.

The composition of the present invention can be administered by a number of routes including, but not limited to injection, topical, transdermal, inhalation, trans-mucosal, oral ingestion, and a combination of a plurality of modes of administration. Additionally, the therapeutic drug may be administered separately from the block copolymers of the present invention, by the same or different route of administration, either simultaneously or at different times. The present invention provides a composition that can be administered to patients who are infected with intracellular pathogens such as *Mycobacterium species*. The surface active copolymer is effective in inhibiting the growth of *Mycobacterium species* and also causes the bacterium to be more susceptible to conventional antibiotics.

Accordingly, it is an object of the present invention to provide a compound which can be used to treat persons with diseases caused by intracellular pathogens.

Accordingly, it is an object of the present invention to provide a compound which can be used to treat persons with infectious diseases.

Yet another object of the present invention is to provide a method of treating viral infections in humans or animals.

Another object of the present invention is a compound and method that is effective in inhibiting the replication of viruses in both animals and humans.

Another object of the present invention is to provide a compound and method that is effective in inhibiting the replication of HIV and other RNA and DNA viruses.

Yet another object of the present invention is to provide a method of treating bacterial infections in humans or animals.

Another object of the present invention is to provide a surfactant compound that can be used to treat mycobacterial infections in persons with AIDS.

Another object of the present invention is to provide a compound effective against protozoa and protozoal infections.

Another object of the present invention is to provide a compound and method that is effective in inhibiting fungal infections.

It is another object of the present invention to inactivate virus in a blood product prior to infusion into a person or animal.

Another object of the present invention is to provide a surfactant compound that can be used to prevent the development of tuberculosis in immunocompromised persons such as the elderly.

A further object of the present invention is to provide a surfactant compound that will inhibit the growth of *Mycobacterium avium* intracellulare complex.

Another object of the present invention is to provide an antibiotic surfactant compound that is non-toxic for humans.

Yet another object of the present invention is to provide a surfactant compound that causes the *Mycobacterium species* to be more susceptible to conventional antibiotics.

Another object of the present invention is to provide a composition that is effective against protozoa such as toxoplasma.

Yet another object of the present invention is to provide a method of treating viral infections in humans or animals.

Another object of the present invention is a compound and method that is effective in inhibiting the replication of viruses in both animals and humans.

It is another object of the present invention to provide a more homogeneous polyoxypropylene/polyoxyethylene copolymer relative to the molecular weight range.

It is another object of the present invention to provide a preparation of polyoxyethylene/polyoxypropylene block copolymer with a polydispersity value of less than 1.17.

It is another object of the present invention to provide a preparation of polyoxyethylene/polyoxypropylene block copolymer with substantially no unsaturation and reaction by-products.

It is yet another object of the present invention to provide a surface-active copolymer which has less cardiotoxicity and less detergent-like activity.

It is yet another object of the present invention to provide a surface-active copolymer that can be used safely in both humans and animals as an antimicrobial agent.

Another object of the present invention is to provide a method for the therapeutic treatment of diseases caused by intracellular pathogens.

It is yet another object of the present invention to provide a surface-active copolymer that has a better therapeutic index than commercially available surface-active copolymers in both humans and animals when used as an antibacterial, an antiviral, an antifungal and an antiprotozoal agent.

These and other objects, features and advantages of the present invention will become apparent after a review of the following detailed description of the disclosed embodiments and the appended claims.

BRIEF DESCRIPTION OF THE DRAWINGS

FIGS. 1A through 1C are gel permeation chromatograms of native and GPC fractions of fractionated poloxamer 331.

FIG. 25 is a graphical representation of the activity of CRL-8131 plus pyrimethamine in mice infected intraperitoneally with tachyzoites of strain RH of *T. gondii*.

FIG. 26 is a graphical representation of the activity of CRL-8131 plus sulfadiazine in mice infected intraperitoneally with tachyzoites of strain RH of *T. gondii*.

FIG. 27 is a graphical representation of the activity of CRL-8131 plus clindamycin in mice infected intraperitoneally with tachyzoites of strain RH of *T. gondii*.

FIG. 28 is a graphical representation of the activity of CRL-8131 plus pyrimethamine in mice infected orally with cysts of the C56 strain of *T. gondii*.

FIG. 31 is a graphical representation of the activity of CRL-8142 plus sulfadiazine in mice infected intraperitoneally with tachyzoites of strain RH of *T. gondii*.

FIG. 32 is a graphical representation of the activity of CRL-8142 plus clindamycin in mice infected intraperitoneally with tachyzoites of strain RH of *T. gondii*.

FIG. 33 is a graphical representation of the activity of CRL-8142 plus pyrimethamine in mice infected orally with cysts of the C56 strain of *T. gondii*.

FIG. 34 is a graphical representation of the activity of CRL-8142 plus sulfadiazine in mice infected orally with cysts of the C56 strain of *T. gondii*.

DETAILED DESCRIPTION

Figure 1A:
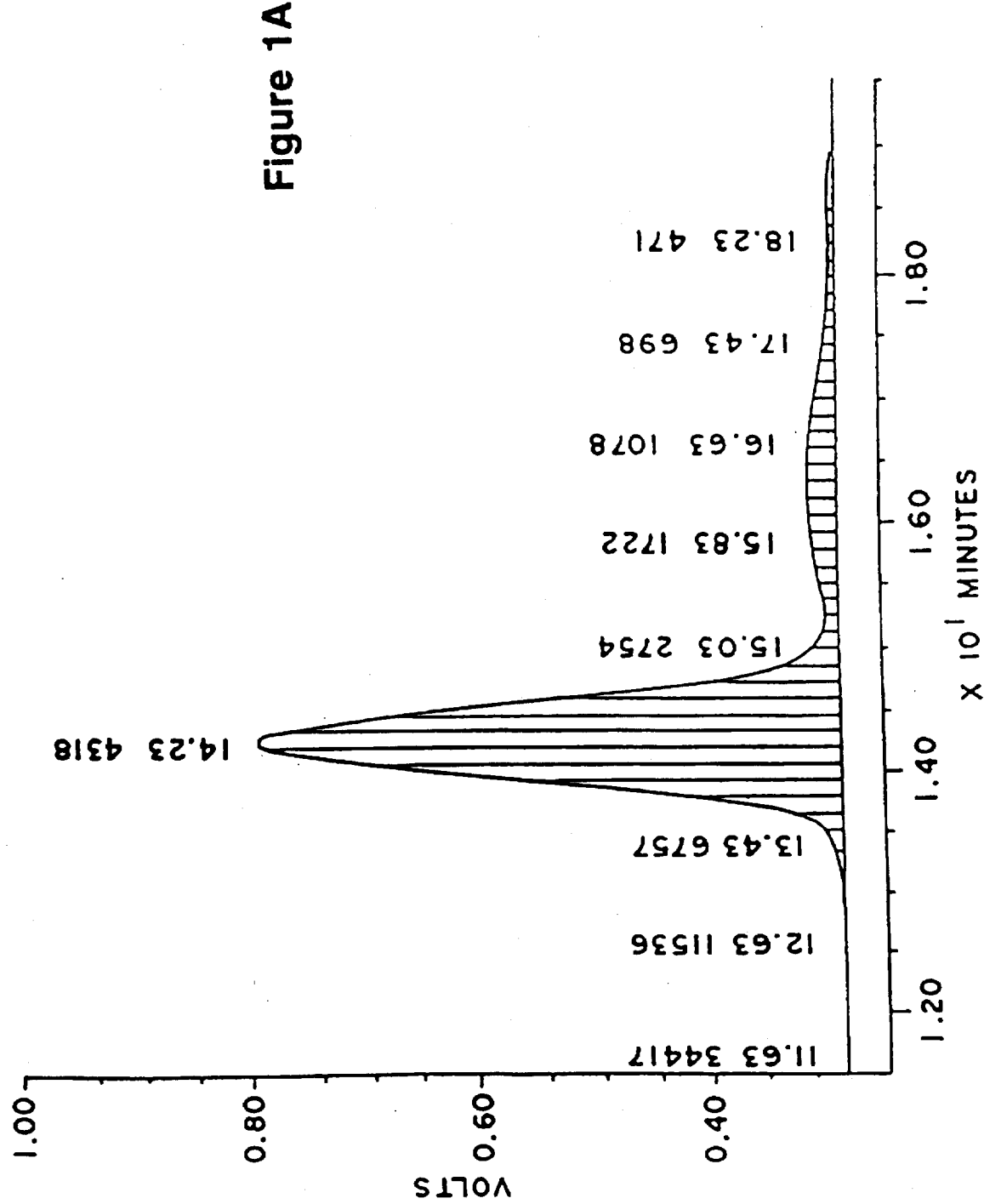

The present invention comprises therapeutic compositions and methods which kill or inhibit the growth of microorganisms. An example of the bacteria that the present invention is effective against is mycobacteria species, such as *Mycobacterium tuberculosis*, *Mycobacterium avium*, and *Mycobacterium leprae*. Other microorganisms that the invention is effective against include, but are not limited to, *Chlamydia trachomatis*, *Chlamydia pneumoniae*, *Chlamydia psittaei* *Listeria monocytogenes*, *Candida albicans*, *Cryptococcus neoformans*, yeast forms of *Histoplasma capsulatum*; *Toxoplasma gondii*, *Trypanosoma cruzi*, *Leishmania donovani*, malarial plasmodia, *Salmonella typhosa*, *Brucella abortus*, *Pneumocystis carinii*, Herpes simplex virus type 1, Cytomegalovirus, influenza virus type A and B, and respiratory syncytial virus.

The present invention also includes therapeutic compositions and methods for treating DNA viruses and RNA viruses, and infections and infectious diseases caused by such viruses in a human or animal, including infections caused by HIV or herpes (such as HSV-1) or antigenically-related strains thereof. Antigenically-related strains are strains that cross react with antibodies specific for HIV. One skilled in the art can readily determine viral strains that are antigenically-related to HIV by conducting standard immunoassay tests using anti-HIV antibodies and the viral strain to be analyzed, and looking for positive cross-reactivity.

The surface active copolymers disclosed herein are effective in inhibiting or suppressing the replication of such viruses in cells.

The present invention also includes a therapeutic composition useful for delivering antimicrobial drugs and treating disease states comprising an admixture of a nonionic block copolymer and an antibiotic or therapeutic drug. Drugs that can be used with the nonionic copolymers of the present invention include, but are not limited to, rifampin, isoniazid, ethambutol, gentamicin, tetracycline, erythromycin, pyrazinamide, streptomycin, clofazimine, rifabutin, fluoroquinolones such as ofloxacin and sparfloxacin, azithromycin, clarithromycin, dapsone, doxycyline, ciprofloxacin, ampicillin, amphotericin B, fluconazole, ketoconazole, fluconazole, pyrimethamine, sulfadiazine, clindamycin, azithromycin, paromycin, diclazaril, clarithromycin, atovaquone, pentamidine, acyclovir, trifluorouridine, AZT, DDI, DDC, and other antiviral nucleoside analogs, foscornat, ganciclovir, viral protease inhibitors, antisense and other modified oligonucleotides, and ribavirin.

Preferred drugs to use for various infectious microorganisms are listed in Table I.

TABLE I

| Organism | Drugs |
|---|---|
| Bacteria | |
| Mycobacterium tuberculosis | Isoniazid, rifampin, ethambutol, pyrazinamide, streptomycin, clofazimine, rifabutin, fluoroquinolones such as ofloxacin, and sparfloxacin |
| Mycobacterium avium | Rifabutin, rifampin, azithromycin, clarithromycin, fluoroquinolones |
| Mycobacterium leprae | Dapsone |
| Chlamydia trachomatis | Tetracycline, doxycyline, erythromycin, ciprofloxacin |
| Chlamydia pneumoniae | Doxycycline, erythromycin |
| Listeria monocytogenes | Ampicillin |
| Fungi | |
| Candida albicans | Amphotericin B, ketoconazole, fluconazole |
| Cryptococcus neoformans | Amphotericin B, ketoconazole, fluconazole |
| Protozoa | |
| Toxoplasma gondii | Pyrimethamine, sulfadiazine, clindamycin, azithromycin, clarithromycin, atovaquone |
| Pneumocystis carinii | Pentamidine, atovaquone |
| Cryptosporidium sp. | Paromomycin, diclazaril |
| Virus | |
| Herpes simplex virus type 1 | Acyclovir, trifluorouridine and other and type 2 antiviral nucleoside analogs, foscarnat, antisense oligonucleotides, and triplex-specific DNA sequences |
| Cytomegalovirus | Foscarnet, ganciclovir |
| HIV | AZT, DDI, DDC, foscarnat, viral protease inhibitors, peptides, antisense oligonucleotides, triplex and other nucleic acid sequences |
| Influenza virus type A and B | Ribavirin |
| Respiratory syncytial virus | Ribavirin |
| Varizella zoster virus | Acyclovir |

Optionally, surfactants and low molecular weight alcohols are added to the therapeutic admixture of antimicrobial drug and nonionic block copolymer. Examples of surfactants useful in the present invention include Tween 80 and emulsions with fatty acids such as phospholipids, cholate and amino acids. The preferred surfactant is Tween 80 (polyoxyethylene sorbitan monooleate). Surfactants are added to the admixture at a concentration ranging from approximately 0.1% to approximately 5% v/v. The preferred surfactant concentration is approximately 2%. The term "approximately" as it applies to concentrations expressed herein means the stated concentration plus or minus ten percent. The term "low molecular weight alcohols" means alcohols having two to eight carbons. An example of a low molecular weight alcohols useful in the present invention is ethanol, which is the preferred low molecular weight alcohol. Low molecular weight alcohols are added to the admixture at a concentration ranging from approximately 0.5% to approximately 5% v/v. The preferred low molecular weight alcohol concentration is between approximately 1% and approximately 3%.

Although the prior art preparations of polyoxypropylene/polyoxyethylene block copolymers may have been suitable for industrial uses, it has been determined that the newly discovered uses for the copolymers as therapeutic agents require less polydisperse populations of molecules in the preparations. It is important that the molecules that are to be used to treat humans or animals have less toxicity and less unsaturation than the prior an preparations of the polyoxypropylene/polyoxyethylene block copolymers.

The present invention comprises polyoxypropylene/polyoxyethylene copolymers that have a polydispersity value of less than 1.17. The novel copolymers can be prepared by removing disparate molecules from the prior art preparation or by synthesizing the copolymer according to the method disclosed in copending patent application Ser. No. 08/292,814, which is incorporated herein by reference. The method of preparation of the copolymers of the present invention also includes the purification of the polyoxypropylene block of the polyoxypropylene/polyoxyethylene copolymer before the polyoxyethylene blocks are added to the molecule. In this way, the partially polymerized polyoxypropylene polymers, including those containing monofunctional unsaturated polymers, are removed before the addition of polyoxyethylene polymers to the molecule. This results in a polyoxypropylene/polyoxyethylene block copolymer that is within the physical parameters which are contemplated as the present invention.

The antiinfective composition of the present invention comprises a surface active copolymer. The surface active copolymer can be an ethylene oxide-propylene oxide condensation product with the following general formula:

wherein "a" is an integer such that the polypropyleneoxide hydrophobe represented by $(C_3H_6O)$ has a molecular weight of approximately 1,200 to approximately 15,000, preferably between approximately 1,500 and approximately 5300, more preferably between approximately 1750 Daltons and approximately 4500 Daltons, still more preferably between approximately 2250 Daltons to approximately 4000 Daltons, and "b" is an integer such that the polyethyleneoxide hydrophile portion represented by $(C_2H_4O)$ constitutes approximately 1% to approximately 50% by weight of the copolymer compound, preferably approximately 5% to approximately 45% by weight of the copolymer compound, more preferably approximately 10% to approximately 30%, and still more preferably approximately 15% to approximately 20%. The copolymer of the present invention has a polydispersity value of less than approximately 1.17.

The present invention includes polyoxypropylene/polyoxyethylene block copolymers with polydispersity values of less than 1.17. Commercially available poloxamer 331 (PLURONIC® L101, BASF, Parsipanny, N.J.) has a typical polydispersity value as high as approximately 1.41. The purification of the polyoxypropylene polymer can be performed by gel permeation chromatography, or other procedures that are well known to those of ordinary skill in the art. It can also be purified by supercritical fluid extraction process. Alternatively, these polymers with significantly reduced polydispersity values can be synthesized using novel synthetic processes. These synthetic processes are described in copending U.S. patent application Ser. No. 08/292,814.

A preferred ethylene oxide-propylene oxide copolymer for use in the antiinfective composition of the present invention is a copolymer having the following formula:

wherein "a" is an integer such that the polypropyleneoxide hydrophobe represented by $(C_3H_6O)$ has a molecular weight of about 1,750 to 4,500 Daltons and "b" is an integer such that the polyethyleneoxide hydrophile portion represented by $(C_2H_4O)$ constitutes approximately 10% to 40% by weight of the copolymer compound.

Another especially preferred embodiment of the antiinfective compound of the present invention is the compound with the following general formula:

wherein the mean aggregate molecular weight of the hydrophobic portion of the triblock copolymer, consisting of polyoxypropylene (POP) is approximately 2500 to 3500 Daltons; the hydrophile portion represented by polyoxyethylene (POE) constitutes approximately 10% to 40% of the total weight of the copolymer compound.

Another especially preferred embodiment of the antiinfective compound of the present invention is the compound with the following general formula:

wherein the mean aggregate molecular weight of the hydrophobic portion of the triblock copolymer, consisting of polyoxypropylene (POP) is approximately 3100 Daltons; the hydrophile portion represented by polyoxyethylene (POE) constitutes approximately 15% of the total weight of the copolymer compound.

Ethylene oxide-propylene oxide condensation products which may be employed in the present invention are summarized in Table II. The polypropyleneoxide hydrophobe (polyoxypropylene) molecular weights are given as approximate midpoints of molecular weight ranges. It is to be understood that these compounds are merely representative of the compounds that can be used to practice the present invention and do not include all possible compounds that could be used to practice the present invention. The high molecular weight copolymers listed in Table II that do not have a BASF tradename are novel compositions that have never been synthesized before. These novel compounds are available from CytRx Corporation, Norcross, Ga. Actual weight percentage may not match with the values reported by the manufacturer

TABLE II

| CRL# | Poloxamer | BASF Trade Name | Molecular Weight of POP | % POE |
|---|---|---|---|---|
|  | 122 | L42 | ≈1200 | ≈20% |
| CRL85171 | 181 | L61 | ≈1750 | ≈10% |
| CRL85172 | 182 | L62 | ≈1750 | ≈20% |
| CRL85173 | 183 | L63 | ≈1750 | ≈30% |
| CRL85174 | 184 | L64 | ≈1750 | ≈40% |
| CRL85175 | 185 | P65 | ≈1750 | ≈50% |
| CRL85178 | 188 | F68 | ≈1750 | ≈80% |
| CRL85202 | 212 | L72 | ≈2050 | ≈20% |
| CRL85221 | 231 | L81 | ≈2250 | ≈10% |
| CRL8122 | 282 | L92 | ≈2750 | ≈20% |
| CRL8131 | 331 | L101 | ≈3250 | ≈10% |
| CRL8133 | 333 | P103 | ≈3250 | ≈30% |
| CRL8135 | 335 | P105 | ≈3250 | ≈50% |
| CRL9038 | 338 | F108 | ≈3250 | ≈80% |
| CRL8141 | 401 | L121 | ≈4000 | ≈10% |
| CRL8142 | 402 | L122 | ≈4000 | ≈20% |
| CRL8143 | 403 | P123 | ≈4000 | ≈30% |
| CRL8941 | 441 | L141 | ≈4400 | ≈10% |
| CRL8950 | — | — | ≈9000 | ≈5% |
| CRL1235 | — | — | ≈7500 | ≈5% |
| CRL1190 | — | — | ≈10,000 | ≈5% |
| CRL1183 | — | — | ≈3750 | ≈10% |
| CRL1122 | — | — | ≈5900 | ≈12% |
| CRL3362 | — | — | ≈3900 | ≈11% |
| CRL3632 | — | — | ≈4740 | ≈11% |
| CRL9352 | — | — | ~7750 | ≈15% |
| CRL-1018 | — | — | ≈3100 | ≈15% |
| CRL1187 | — | — | ≈750 | ≈25% |

Although molecular weight averages are important and useful when characterizing polymers in general, it is important to know the molecular weight distribution of a polymer.

Some processing and end-use characteristics (melt flow, flex life, tensile strength, etc.) are often predicted or understood by observing the values and/or changes occurring in specific molecular weight averages and polydispersity values. A list of the processing characteristics follows.

| Molecular Weight Averages | Processing Characteristics |
|---|---|
| Mz | Flex life/stiffness |
| Mn | Brittleness, flow |
| Mw | Tensile strength |

These molecular weight values can also be correlated with the biological properties of polyoxypropylene/polyoxyethylene copolymers. The breadth of the distribution is known as the polydispersity (D) and is usually defined as Mw/Mn. A monodisperse sample is defined as one in which all molecules are identical. In such a case, the polydispersity (Mw/Mn) is 1.0. Narrow molecular weight standards have a value of D near 1 and a typical polymer has a range of 2 to 5. Some polymers have a polydispersity in excess of 20.

The equations for expressing various average molecular weights and polydispersity (from GPC chromatography) are as follows:

$$\overline{M}_n = \text{Number Average} = \frac{\Sigma Area_i}{\Sigma Area_i/M_i}$$

$$\overline{M}_w = \text{Wt. Average} = \frac{\Sigma[(Area_i)(M_i)]}{\Sigma(Area_i)}$$

$$\overline{M}_z = \text{Z Average} = \frac{\Sigma[(Area_i)(M_i)^2]}{\Sigma[(Area_i)(M_i)]}$$

$$\overline{M}_{z+1} = Z+1 \text{ average} = \frac{\Sigma[(Area_i)(M_i)^3]}{\Sigma[(Area_i)(M_i)^2]}$$

$$\text{Polydispersity}(D) = \frac{\overline{M}_w}{\overline{M}_n}$$

where:

$Area_i$ = area of the ith slice $M_i$ = molecular weight of the ith slice

Thus, by calculating the parameters listed above, one can specify a certain polydispersity that is acceptable for a pharmaceutical preparation. A high polydispersity value indicates a wide variation in size for the population of molecules in a given preparation while a lower polydispersity value indicates less variation. Because molecular size is an important determinant of biological activity, it is important to restrict the dispersity of the molecules in the preparation in order to achieve a more predictable and homogeneous biological effect. Thus, the polydispersity measurement can be used to measure the dispersity of molecules in a preparation and correlates to that compound's potential for variation in biological activity.

It is to be understood that the polydispersity values that are described herein were determined from GPC chromatograms which were obtained using a Model 600E Powerline chromatographic system equipped with a column heater module, a Model 410 refractive index detector, Maxim 820 software package (all from Waters, Milford, Mass.), two LiChrogel PS-40 columns and a LiChrogel PS-20 column in series (EM Science, Gibbstown, N.J.), or Ultra styragel GPC columns (by Waters, Milford, Mass.) and polyethylene glycol molecular weight standards (Polymer Laboratories, Inc., Amherst, Mass.). Polydispersity values obtained using this system are relative to the chromatographic conditions, the molecular weight standards and the size exclusion characteristics of the gel permeation columns. Polydispersity measurements using different separation principles may give absolute polydispersity values which are different from those described herein. However, one of ordinary skill in the art can easily convert any polydispersity value that is obtained using a different separation method to the values described herein simply by running a single sample on both systems and then comparing the polydispersity values from each chromatogram.

In accordance with the present invention, a composition is provided that is a polyoxypropylene/polyoxyethylene triblock copolymer that has a polydispersity value of less than 1.17. Preferably, the polydispersity value is less than approximately 1.10, with a most preferred polydispersity value of 1.05. It is to be understood that the present invention includes, but is not limited to, poloxamer compounds.

Another method of describing one of the preferred embodiments of the present invention is to describe the copolymer in terms of the percent of the unfractionated or native copolymer that is purified. For example the preferred embodiment is at least a substantially pure block copolymer having the formula

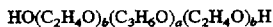

$HO(C_2H_4O)_b(C_3H_6O)_a(C_2H_4O)_bH$ wherein the molecular weight of the polypropyleneoxide hydrophobe ($C_3H_6O$) is approximately 3100 Daltons and the average molecular weight of the compound is approximately 3700 Daltons, and wherein the block copolymer comprises at least 85 percent by weight of high molecular weight fraction, and not more than 15 percent by weight of a low molecular weight impurity when fractionated by gel permeation chromatography or supercritical fractionation.

The surface-active copolymers of the present invention can be prepared in a number of ways. The polydispersity value of the commercially available compounds can be reduced by subjecting commercially available compounds to well known fractionation procedures such as gel permeation chromatography or supercritical fluid extraction. In addition, the compounds can be subjected to molecular sieving techniques that are known to those of ordinary skill in the art.

The surface-active copolymers of the present invention have been shown to be effective with only one administration to the patient. However, in most cases, subsequent administrations will be necessary to achieve maximum efficiency. The mode of administration can be topical, transdermal, transmucosal, oral, inhalation, subcutaneous, intramuscular or intravenous. The preferred mode of injection is intravenous. The optimum amount of the antiinfective compound of the present invention in a dose varies with the weight of the patient being treated. The effective dose range generally includes dosages of 0.1 mg/Kg/day to 50 mg/Kg/day. A preferred dosage range is 0.5 mg/Kg/day to 25 mg/Kg/day. A more preferred dosage range is 1 mg/Kg/day to 10 mg/Kg/day. It has been surprisingly found that effective therapy is provided even when the block copolymer and the therapeutic drug are administered separately, either by the same or different routes of administration, and either simultaneously or at different times.

The antiinfective compound of the present invention is effective in suppressing the growth of *Mycobacterium avium*, *Mycobacterium tuberculosis*, *Herpes simplex* virus type 1 and type 2, *Toxoplasmi gondii* and other microorganisms affecting humans and animals causing a variety of health disorders. The disorders in which the antiinfective compound of the present invention are effective include, but are not limited to bacterial infections, fungal infections, protozoal infection and viral infections. Examples of specific diseases include tuberculosis, toxoplasmosis, and AIDS. Other diseases caused by microorganisms will be obvious to one of skill in the art.

The surface-active copolymers form micelles above their critical micelle concentration. The non-ionic copolymers have negative thermal coefficients of solubility. In the cold, the kinetic energy of water molecules is reduced and they form weak hydrogen bonds with the oxygen of the POP blocks. This hydration of the hydrophobe promotes solubility at low temperatures. As the temperature rises, the "cloud point" is reached; the increased kinetic energy of the water breaks the hydrogen bonds, the polymer becomes insoluble and micelles form.

Thus, the surface-active copolymers can form physical structures that can be combined or loaded with an additional, distinct therapeutic agent. Consequently, the nonionic block copolymers of the present invention can be used as therapeutic drug delivery vehicles. Admixtures of therapeutic drugs with non-ionic block copolymers have the advantage of synergistic activity of two therapeutic agents. Further, surface-active copolymers having specific characteristics can be selected for use with particular therapeutic drugs. For example, CRL8131, which is hydrophobic, is an excellent carrier for hydrophobic antibiotics such as rifampin. However, other agents which are not distinctly hydrophobic can be used according to the present invention.

A therapeutic delivery composition is prepared using any of the surface-active copolymers of the present invention in combination with any of a variety of antimicrobial agents. In a preferred embodiment CRL8131 is used in a concentration of approximately 3% to approximately 5% to construct a therapeutic delivery vehicle. Therapeutic delivery vehicles made using copolymers that are more hydrophilic than CRL8131 normally require a higher concentration (approximately 5% to approximately 10%) of the copolymer.

Using copolymer-based micelles as a therapeutic drug delivery vehicles is particularly desirable because the micelles are accumulated readily and are present for an extended period of time, in macrophages, the site of HIV and other viral infections and a major target for viral therapy. Examples of such therapeutic copolymer-based therapeutic compositions include, but are not limited to, CRL8131 combined with 2% Tween 80 and 1% ethanol. Other pharmaceutically acceptable vehicles may be used in effectively delivering the surface-active copolymers.

Alternatively, nonionic block copolymers of the present invention and therapeutic drugs may be administered to a human or animal separately, either simultaneously or at different times. For example, copolymers such as CRL8131 or CRL8142 are administered by injection, followed by administration of the therapeutic drug. Administration of the drug may be by any normal route such as, injection, topical or transdermal application, trans-mucosal absorption, inhalation or oral ingestion.

The following specific examples illustrate various aspects of the invention, such as in vitro suppression of the growth of colonies of *Mycobacterium avium* and HIV virus in vitro isolated from humans. Several of the examples also illustrate the invention as it applies to the suppression of growth of *Mycobacterium avium* and *Toxoplasma gondii* in macrophages. Still other examples illustrate the compositions and methods of the invention useful for gene therapy, and compositions and methods of the invention useful for gene-mediated immunization. It will be appreciated that other embodiments and uses will be apparent to those skilled in the art and that the invention is not limited to these specific illustrative examples.

It should be understood that the molecular weight range that is described as the optimum range for the copolymer is to be considered the outside range and that any population of molecules that fall within that range are considered as embodiments of the present invention.

EXAMPLE I

Poloxamer 331 (Pluronic® L101, BASF Corporation, Parsippany, N.J.) was fractionated as follows: Poloxamer 331 (BASF Corporation, Parsippany N.J.) is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the commercially prepared poloxamer 760.5 copolymer. The chromatographic system is equipped with Ultrastyragel $10^3$ A and 500 A in series (Waters, Div. of Millipore, Milford, Mass.). Column size is 7.8 mm internal diameter by 30 cm. Precolumn filters #A-315 with removable 2 µm frits (Upchurch Scientific, Oak Harbor, Wash.) were used for protection of the columns. 200 µL (4 mg) of the poloxamer 760.5 in tetrahydrofuran is added to the column and the sample is run with the columns at 40° C. and the detector at 45° C. The chromatographs for native poloxamer 331, an early eluting fraction and a late eluting fraction are shown in FIGS. 1A through 1C respectively. All proton NMR analyses were performed in accordance with the NF procedure "Weight Percent Oxyethylene" on a Bruker 300 MHz instrument. The results of these spectra and chromatograms are summarized in Table III.

TABLE III

| Fraction | % POE[a] | MW[b] | Unsaturation[c] |
|---|---|---|---|
| Native | 17 | 4045 | Yes |
| HMW Purified Fraction | 15 | 4452 | No |
| LMW Impurity | 31 | 1466 | Yes | a. As measured by NMR
b. As measured by gel permeation chromatography
c. As measured by NMR When the poloxamer number for each fraction is calculated based on the empirical data collected, it is seen that the low molecular weight impurities are very different in structure when compared to the native preparation. In addition, the unsaturated population of molecules have been substantially removed by the fractionation procedure.

EXAMPLE II

CRL8131 was fractionated by supercritical fluid extraction. About 2350 grams of CRL8131 was mixed with 1604 grams of Hydromatrix (Varian) and loaded into an extraction vessel. A process development unit (PDU) with $CO_2$ recycling capability was used. Supercritical $CO_2$ was continuously passed through the extraction cell with an upward flow. The extraction cell was maintained at 40° C. Several fractions were collected by varying the pressure of supercritical $CO_2$. The extraction conditions and the amount of each fraction collected are given in Table IV along with the characterization results.

The fractions were characterized by Gel Permeation Chromatography using PEG standards, NMR, residual ethylene glycol and propylene glycol and unsaturation. Gel Permeation Chromatography provided different weight average molecular weights. Percentage of ethylene oxide units was determined from NMR. Unsaturation was measured by wetchemistry and provided amount of —CH=CH— groups present in the end groups.

EXAMPLE III

As shown in Table IV, fractions 159-21-1 through 159-21-6 were collected with supercritical $CO_2$ pressure at 2200 psi, fractions 159-21-7 through 159-21-11 were collected at 3400 psi, and fractions 159-21-12 through 159-21-17 were collected at 4400 psi. Fraction 159-21-18 is the component that is soluble in liquid $CO_2$. Fraction 159-21-19 is what is left in the extraction after the extraction process (material that was not extractable during the fractionation). Fraction 159-21-20 is the starting material before extraction.

TABLE IV

Characterization of CRL8131 Fractions (Obtained by Supercritical Fluid Extraction)

| Fractions Lot # | Amount Collected gm | Mn | Mw | Mp | PD | EG/PG ppm | % EO | Unsaturation mEq/gm | Moles of Unsaturation per Mole of Polymer |
|---|---|---|---|---|---|---|---|---|---|
| 159-21-1* | 2.5 | 934 | 1101 | 1051 | 1.18 | None/None | — | 0.7166 | 0.67 |
| 159-21-2* | 12.1 | 806 | 945 | 895 | 1.17 | 36.1/60.2 | 31.7 | 0.752 | 0.61 |
| 159-21-3 | 15.5 | 758 | 882 | 822 | 1.16 | 62.4/82.6 | — | — | — |
| 159-21-4 | 35.9 | 782 | 941 | 850 | 1.2 | — | 32 | — | — |
| 159-21-5 | 21.3 | 826 | 980 | 934 | 1.19 | — | — | 0.7638 | 0.63 |
| 159-21-6 | 17.8 | 879 | 1040 | 1016 | 1.18 | 84.0/83.2 | 33.9 | 0.7746 | 0.68 |
| 159-21-7 | 38.9 | 1059 | 1270 | 1154 | 1.2 | — | — | — | — |
| 159-21-8 | 36 | 1231 | 1507 | 1312 | 1.22 | — | 31.6 | 0.7049 | 0.87 |
| 159-21-9 | 17.5 | 1327 | 1645 | 1369 | 1.24 | — | — | — | — |
| 159-21-10 | 24.4 | 1484 | 1877 | 1429 | 1.26 | — | 29.5 | 0.5026 | 0.75 |
| 159-21-11 | 14.2 | 1611 | 2121 | 1505 | 1.32 | 67.9/59.8 | — | 0.4634 | 0.75 |
| 159-21-12 | 29.5 | 2007 | 2510 | 3487 | 1.25 | — | 22.7 | 0.3273 | 0.66 |
| 159-21-13 | 30.7 | 2349 | 2862 | 3664 | 1.22 | — | — | — | — |
| 159-21-14 | 27.5 | 2625 | 3064 | 3487 | 1.17 | — | — | — | — |

TABLE IV-continued

Characterization of CRL8131 Fractions (Obtained by Supercritical Fluid Extraction.

| Fractions Lot # | Amount Collected gm | Mn | Mw | Mp | PD | EG/PG ppm | % EO | Unsaturation mEq/gm | Moles of Unsaturation per Mole of Polymer |
|---|---|---|---|---|---|---|---|---|---|
| 159-21-15 | 23.8 | 2825 | 3198 | 3487 | 1.13 | — | — | 0.1271 | 0.36 |
| 159-21-16 | 22.7 | 2970 | 3296 | 3487 | 1.11 | — | — | — | — |
| 159-21-17 | 21.9 | 3110 | 3378 | 3487 | 1.09 | — | 11.1 | — | — |
| 159-21-18* | ** | 1075 | 2734 | 3700 | 2.54 | 2686.2/351.2 | 11.9 | 0.7779 | 0.84 |
| 159-21-19 | *** | 4112 | 4266 | 4091 | 1.04 | (304.6)/None | 14.7 | 0.0013 | 0.0053 |
| 159-21-20 | **** | 3219 | 3988 | 4305 | 1.24 | — | 15.8 | 0.1064 | 0.34 |

Supercritical Fluid Extraction Conditions:
Carbon Dioxide Flow rate = 1400 mL/min, Temperature = 40 C.
Fractions 1 through 6 collected at 2200 psi
Fractions 7 through 11 collected at 3400 psi
Fractions 12 through 17 collected at 4400 psi
* — Slightly Yellow
** — Evaporated the carbon dioxide solution at the separator (liquid carbon dioxide soluble fraction)
*** — Left behind at the extractor
**** — Starting CRL8131, mixed with hydromat

EXAMPLE IV

Figure 2:
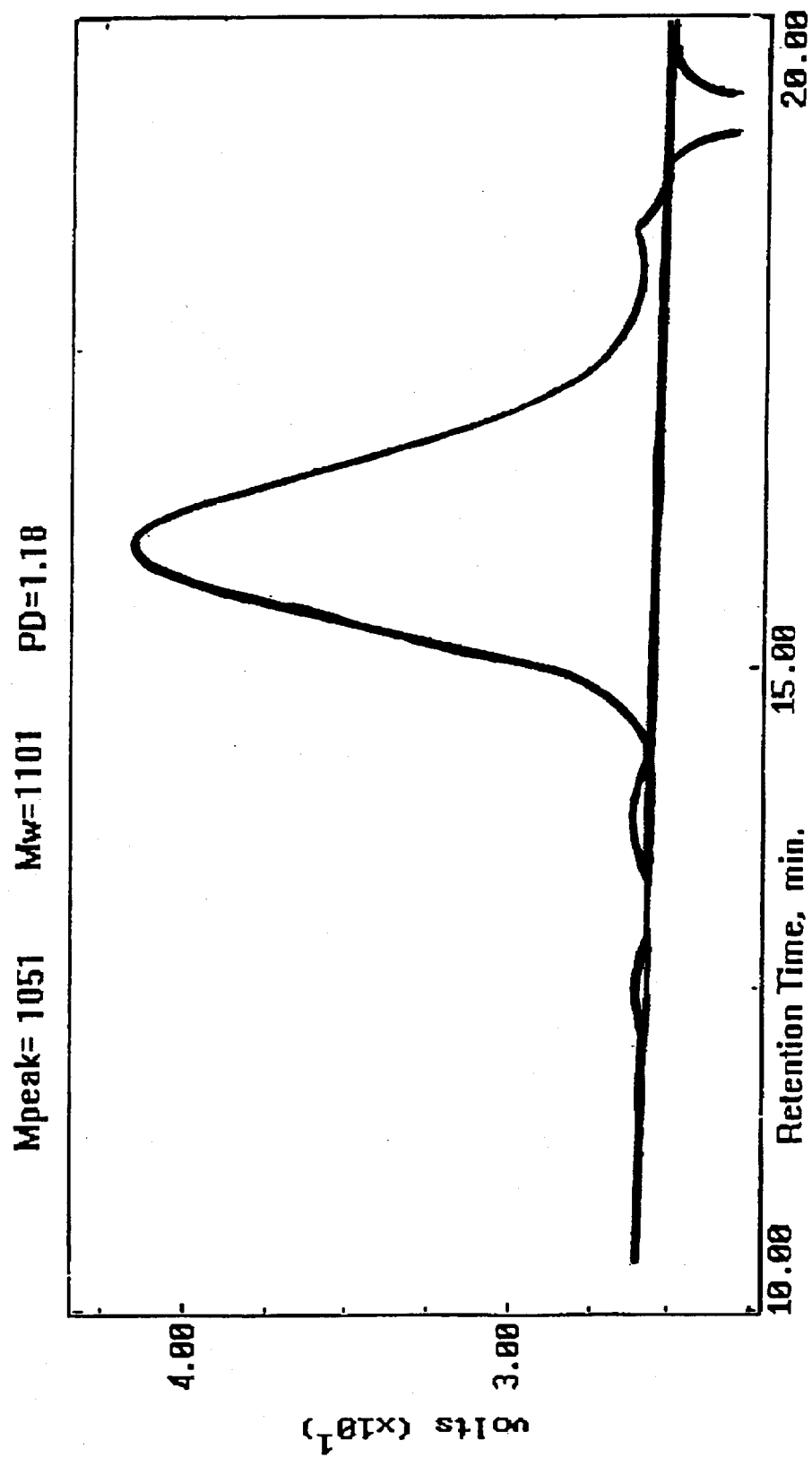
FIG. 2 is a gel permeation chromatogram of the low molecular weight impurity from a supercritical fluid extraction at a $CO_2$ pressure of 2200 psi of CRL8131.
Figure 3:
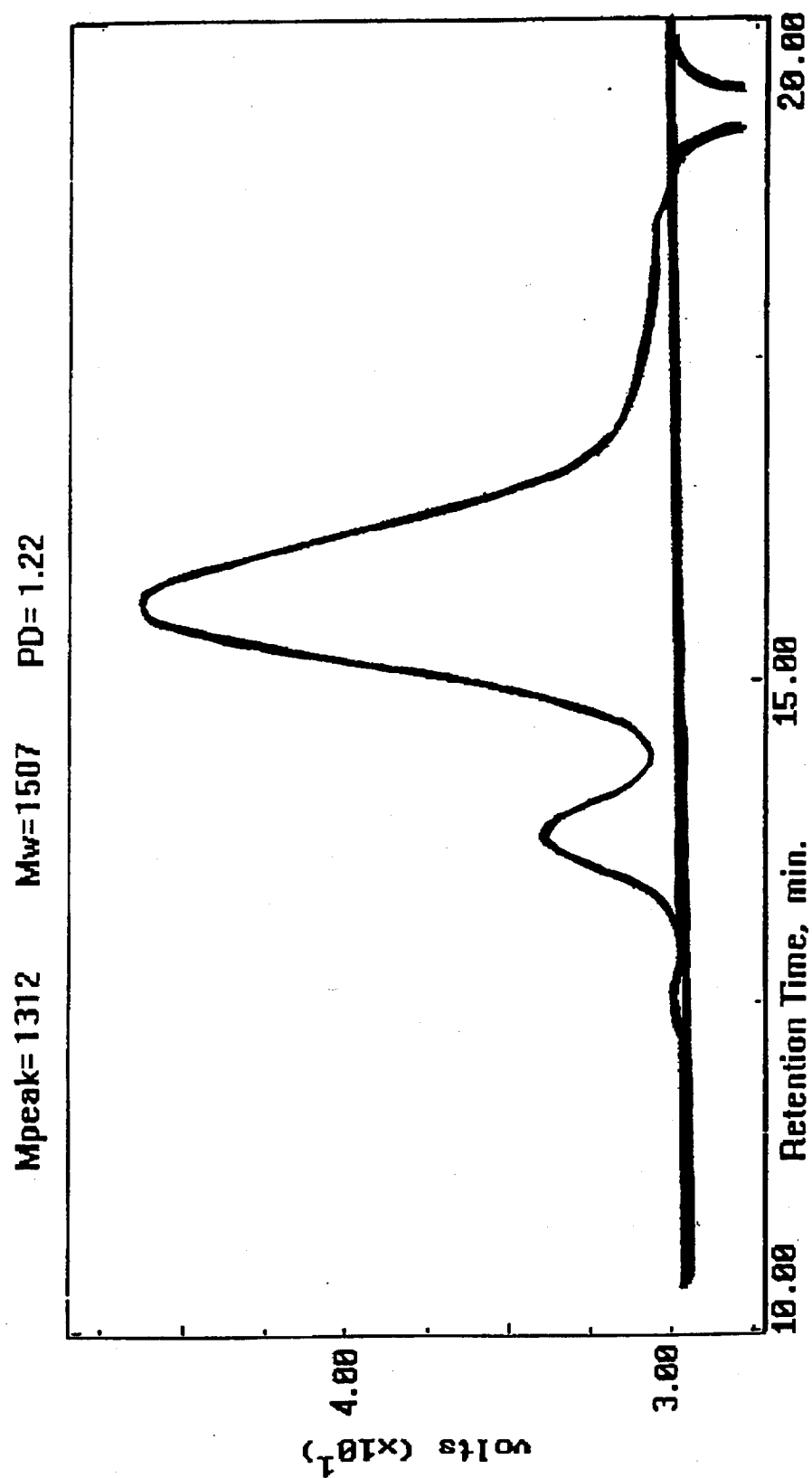
FIG. 3 is a gel permeation chromatogram of the low molecular weight impurity from a supercritical fluid extraction at a $CO_2$ pressure of 3300 psi of CRL8131.
Figure 4:
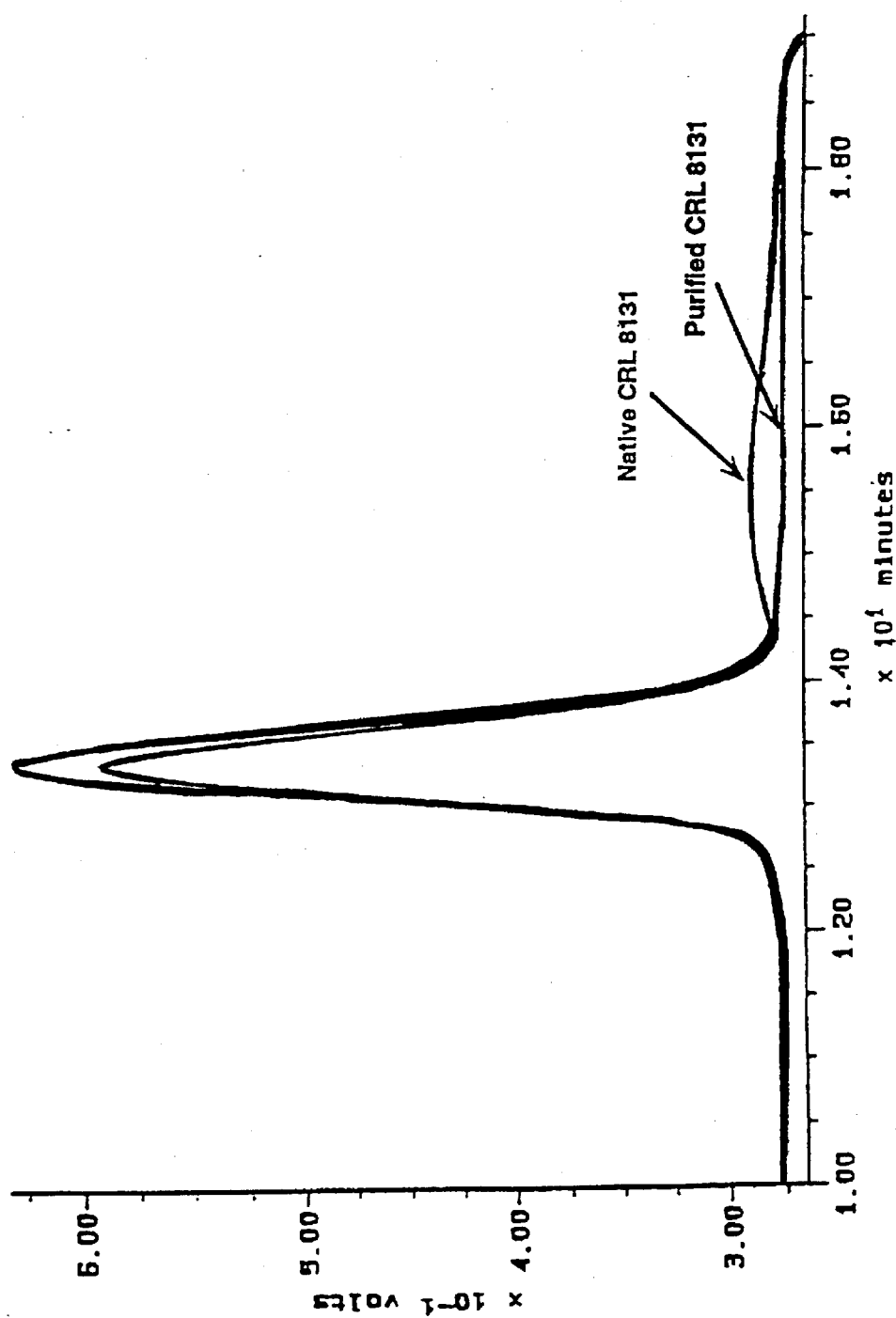
FIG. 4 are gel permeation chromatograms comparing the native CRL8131 and a purified CRL8131 obtained by supercritical fluid extraction of native CRL8131.

From GPC analyses, it is shown that most of the low molecular weight impurity was removed by the supercritical $CO_2$ at 2200 psi. At this pressure range, the extracted material primarily had a single broad peak (FIG. 2) with the peak average molecular weight ranging from 800 to 1000 Daltons. Supercritical $CO_2$ (at 3400 psi) extracted mostly low molecular weight (FIG. 3) but with a small fraction of high molecular weight component. Higher pressure (4400 psi) supercritical $CO_2$ extracted relatively higher molecular weight fractions. The important observation is that the material remaining in the extractor after fractionation (fraction 159-21-19) did not have any low molecular weight components in GPC. It has a single, narrow peak (FIG. 4) with peak average molecular weight of 4091 and polydispersity of 1.04 vs. 1.24 for the starting material.

The fraction 159-21-18 had the accumulation of liquid $CO_2$ soluble fraction of the starting material collected through out the extraction. This fraction had the largest polydispersity of 2.54 with several small peaks in the very low molecular weight region. This fraction also had the highest amount of ethylene glycol (2686 ppm) and propylene glycol (351 ppm). This observation indicates that the starting material can be purified from very low molecular weight components such as ethylene glycol and propylene glycol just by washing with liquid $CO_2$.

EXAMPLE V

The percentage of ethylene oxide as measured from NMR spectra of certain fractions, were higher for supercritical $CO_2$ extractable fractions. The low molecular weight component of CRL8131 has relatively higher ethylene oxide content than the high molecular weight component. It is believed that the fractionation was driven by higher ethylene oxide content in combination with the lower molecular weight. Consequently, the high molecular weight component remaining in the extractor had slightly lower ethylene oxide than the starting material.

The supercritical $CO_2$ extractable, low molecular weight component has relatively higher amount of unsaturation than the high molecular weight component. The unsaturation is probably the result of the side reactions during the polymerization of propylene oxide. These side reactions caused the formation of low molecular weight, unsaturated component.

The high molecular weight component has the least amount of unsaturation. On per mole basis, in supercritical $CO_2$ extractable low molecular weight impurities, approximately 60 to 85 percent of the molecules are unsaturated on one end of the chain. This indicates that approximately 60 to 85 percent of the molecules have AB (di) block structure where the high molecular weight fraction has mostly ABA (tri) block structure.

The fractions were also analyzed by FT-IR. We observed that $CO_2$ extractable, low molecular weight impurities have small absorption peaks around 1650 characteristic of unsaturation; whereas, the high molecular weight fraction that remained in the extractor did not have such peaks.

EXAMPLE VI

Figure 7:
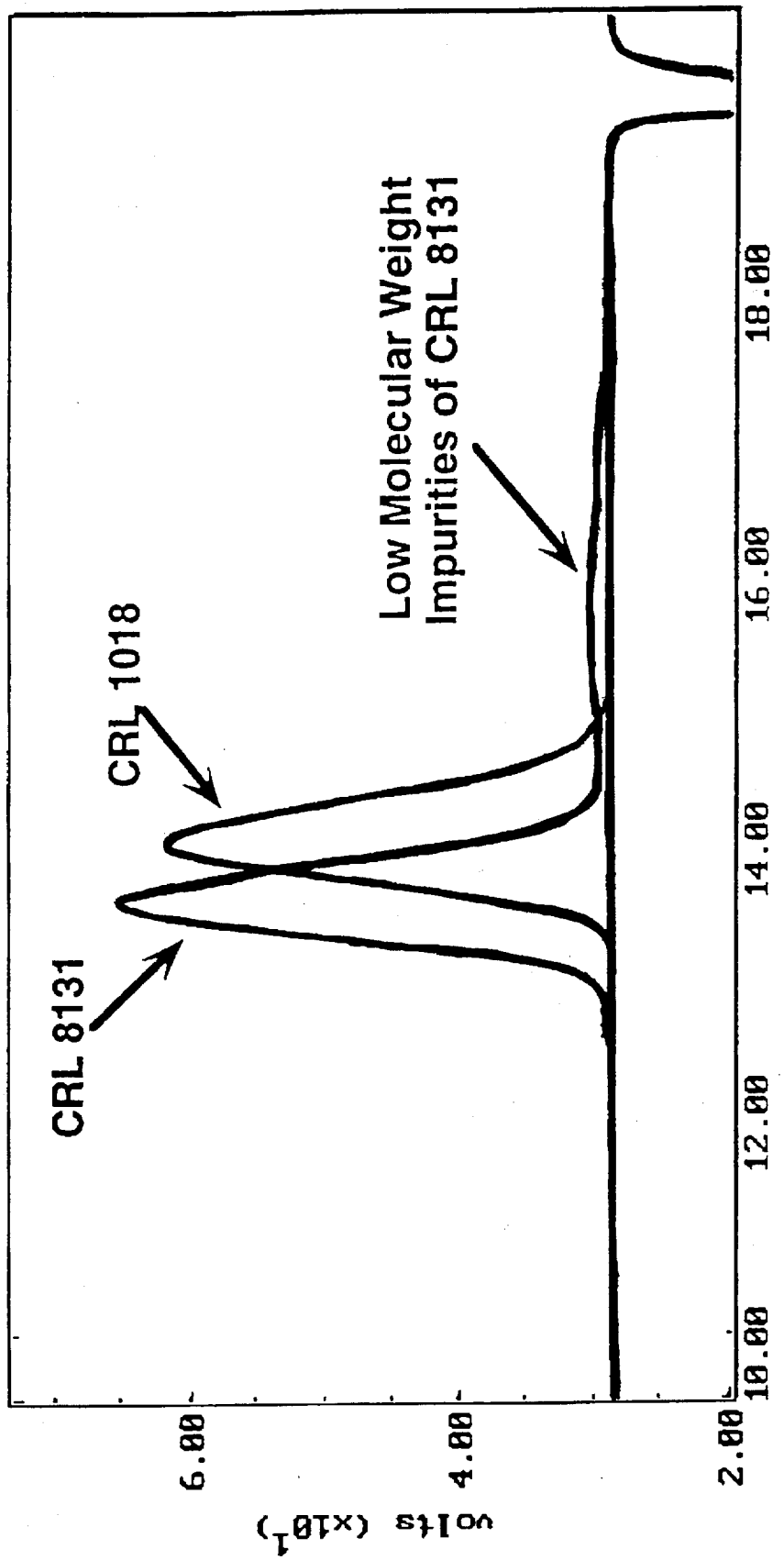
FIG. 7 is the gel permeation chromatograms of a synthetically prepared poloxamer that has significantly low amounts of unsaturation and low molecular weight impurities with low polydispersity compared with a similar commercially available poloxamer CRL8131.

Synthetic preparation of low polydisperse poloxamer CRL1018:

CRL1018 is similar to purified high molecular weight fraction of CRL8131 with regard to lack of low molecular weight impurities and polydispersity. The peak molecular wieght of 1018 is slighly lower than the purified high molecular weight fraction of CRL8131. The CRL1018 is considered part of the present invention. About 0.058 g of Cesium hydroxide monohydrate which was used as a catalyst was mixed with 0.152 g of propylene glycol (initiator) in a reactor. About 7.625 g of propylene oxide was added slowly while heating the reactor at 100° C. Then the polymerization was continued with the addition of about 1.36 g of ethylene oxide at 100° C. After the reaction, the catalyst was removed by heating the reaction product with magnesium silicate and filtered. The weight of the final product is 6.8 grams. The GPC analysis of this polymer showed a single peak with the peak molecular weight of 3675 daltons, weight average molecular weight of 3584 daltons, and polydispersity of 1.043. The peak comprised molecules ranging from 2000 to 6000 daltons. A gel permeation chromatogram of the CRL1018 is shown in FIG. 7

EXAMPLE VII

Additional supercritical fractionation experiments were performed on CRL8131, similar to the method described Example IV. The physical characteristics of the fractions collected during these additional fractionation experiments are described in Table V.

TABLE V

Additional supercritical extraction experiments:

| Fraction ID | Peak Mwt | Wt Avg. Mwt. | Poly-dispersity | Comments |
|---|---|---|---|---|
| Sample: CRL8131 Lot# 120-1; | | | | |
| CRL8131 | 4225 | 3978 | 1.22 | Starting Material |
| 8131-2-1 | 1144 | 1843 | 1.73 | Low Mol. Wt. impurity |
| 8131-2-2 | 3705 | 2469 | 1.54 | Mixture of high and low mol. wt. fractions |
| 8131-2-3 | 3561 | 2558 | 1.40 | Mixture of high and low mol. wt. fractions |
| 8131-2-4 | 3632 | 3269 | 1.49 | Mixture of high and low mol. wt. fractions |
| 8131-2-5 | 3742 | 3711 | 1.09 | High Mol. Wt. fraction |
| 8131-2-6 | 3818 | 3999 | 1.05 | High Mol. Wt. fraction |
| 8131-2-7 | 4015 | 4130 | 1.06 | High Mol. Wt. fraction |
| 8131-2-8 | 4225 | 4221 | 1.07 | High Mol. Wt. fraction |
| 8131-2-9 | 4541 | 4537 | 1.08 | High Mol. Wt. fraction |
| 8131-2-10 | 4785 | 5266 | 1.10 | High Mol. Wt. fraction |
| Sample: CRL8131 Lot# 120-3; | | | | |
| CRL8131 | 4270 | 3953 | 1.27 | Starting Material |
| 8131-3-1 | 1050 | 1450 | 1.43 | Low Mol. Wt. fraction |
| 8131-3-2 | 4060 | 3860 | 1.12 | Mixture of high and low mol. wt. fractions |
| 8131-3-3 | 4310 | 4390 | 1.02 | High Mol. Wt. fraction |
| 8131-3-4 | 4540 | 4600 | 1.02 | High Mol. Wt. fraction |
| 8131-3-5 | 4700 | 5060 | 1.03 | High Mol. Wt. fraction |
| Sample: CRL8131 Lot# 120-2; | | | | |
| CRL8131 | 4350 | 4030 | 1.30 | Starting Material |
| 8131-4-1 | 1030 | 1860 | 1.67 | Low Mol. Wt. fraction |
| 8131-4-2 | 3950 | 2970 | 1.40 | Mixture of high and low mol. wt. fractions |
| 8131-4-3 | 4130 | 3740 | 1.16 | Mixture of high and low mol. wt. fractions |
| 8131-4-4 | 4350 | 4330 | 1.06 | High Mol. Wt. fraction |
| 8131-4-5 | 4700 | 5130 | 1.06 | High Mol. Wt. fraction |

XXX

As described in Table V, the first fraction collected during supercritical extraction was primarily low molecular weight component, and the later fractions were high molecular weight components.

Figure 5:
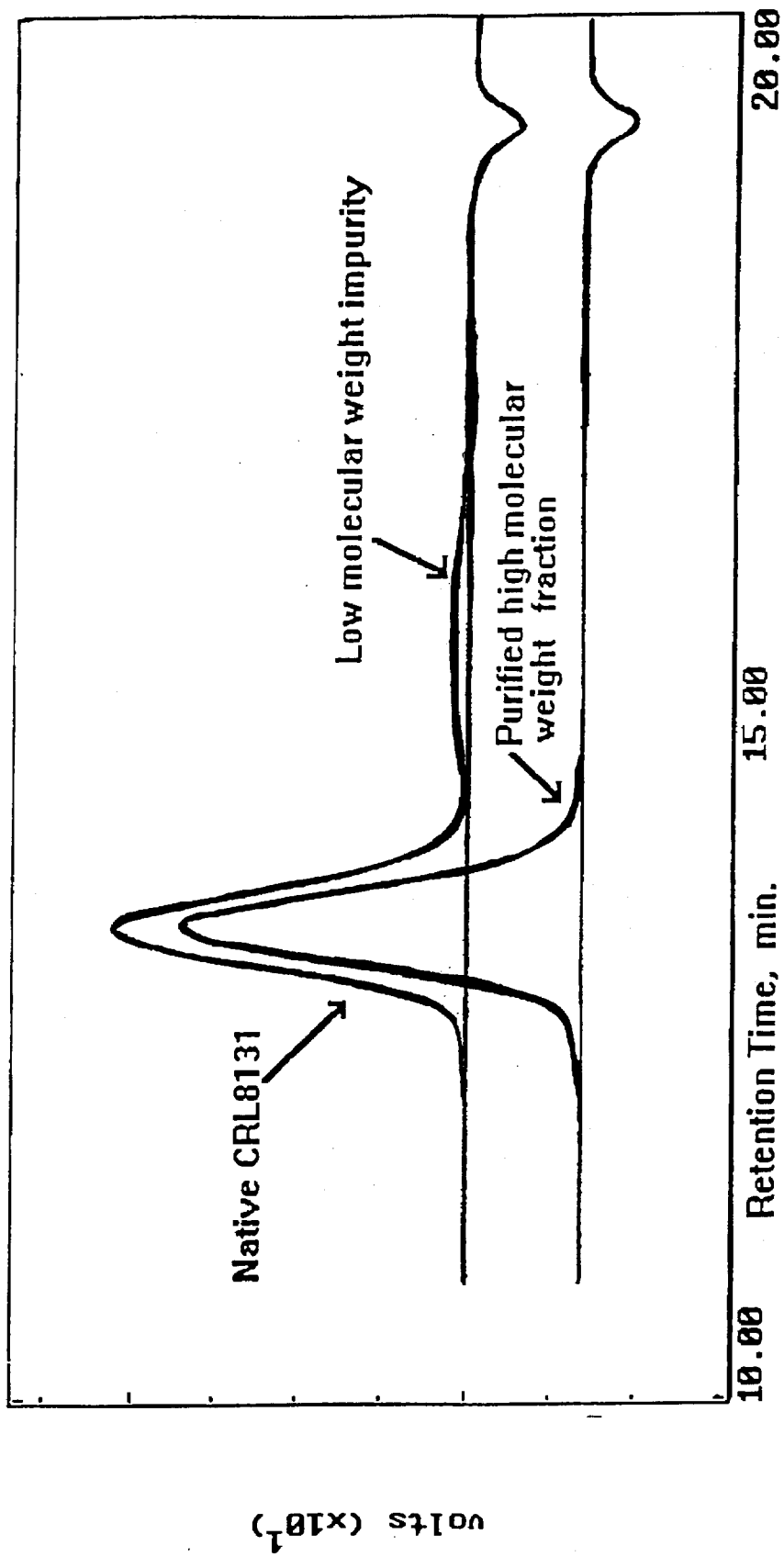
FIG. 5 is a gel permeation chromatogram of the native CRL8131.
Figure 6A:
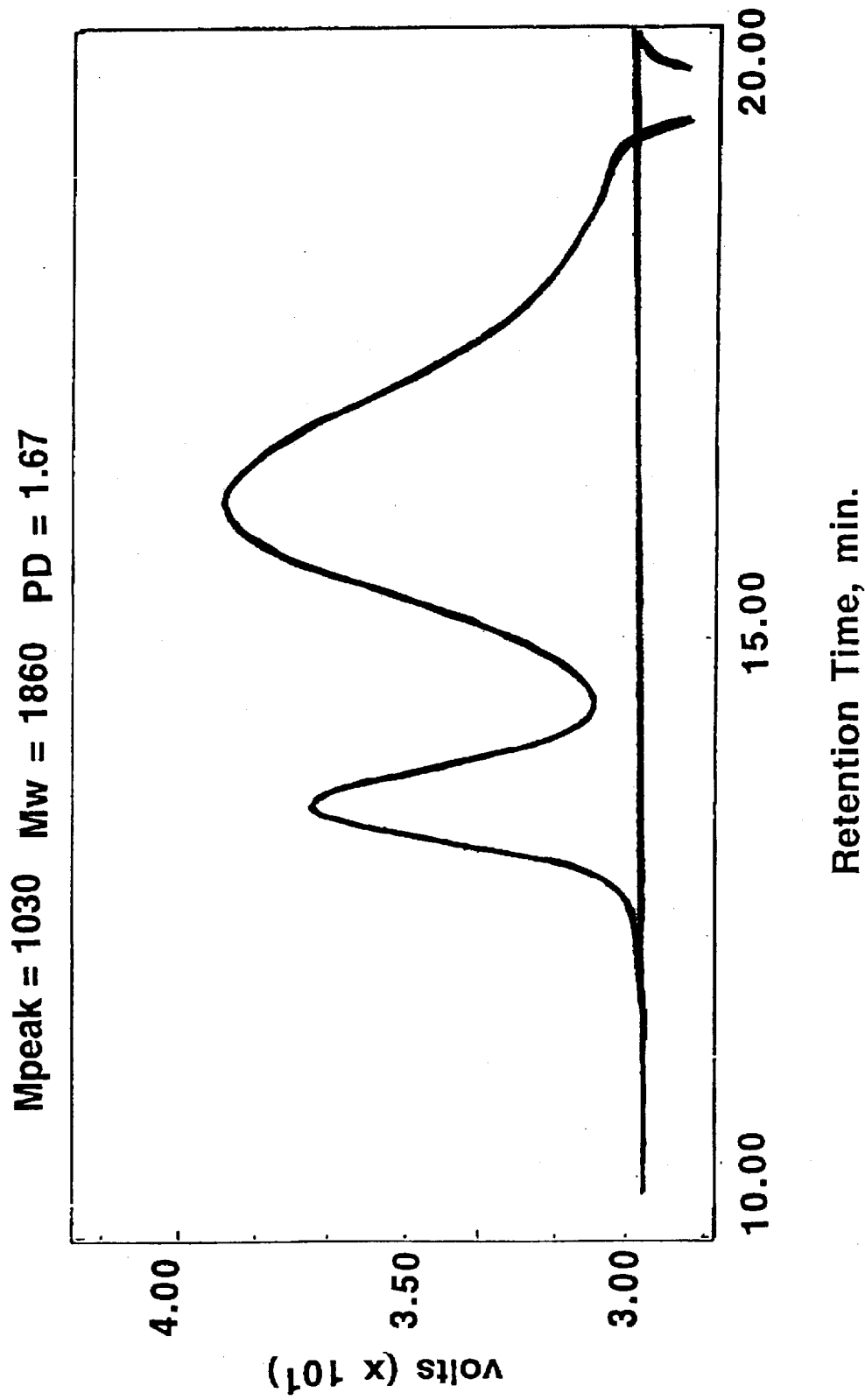
FIG. 6A is a chromatogram of the low molecular weight impurities from super critical fractionation of CRL8131.
Figure 6B:
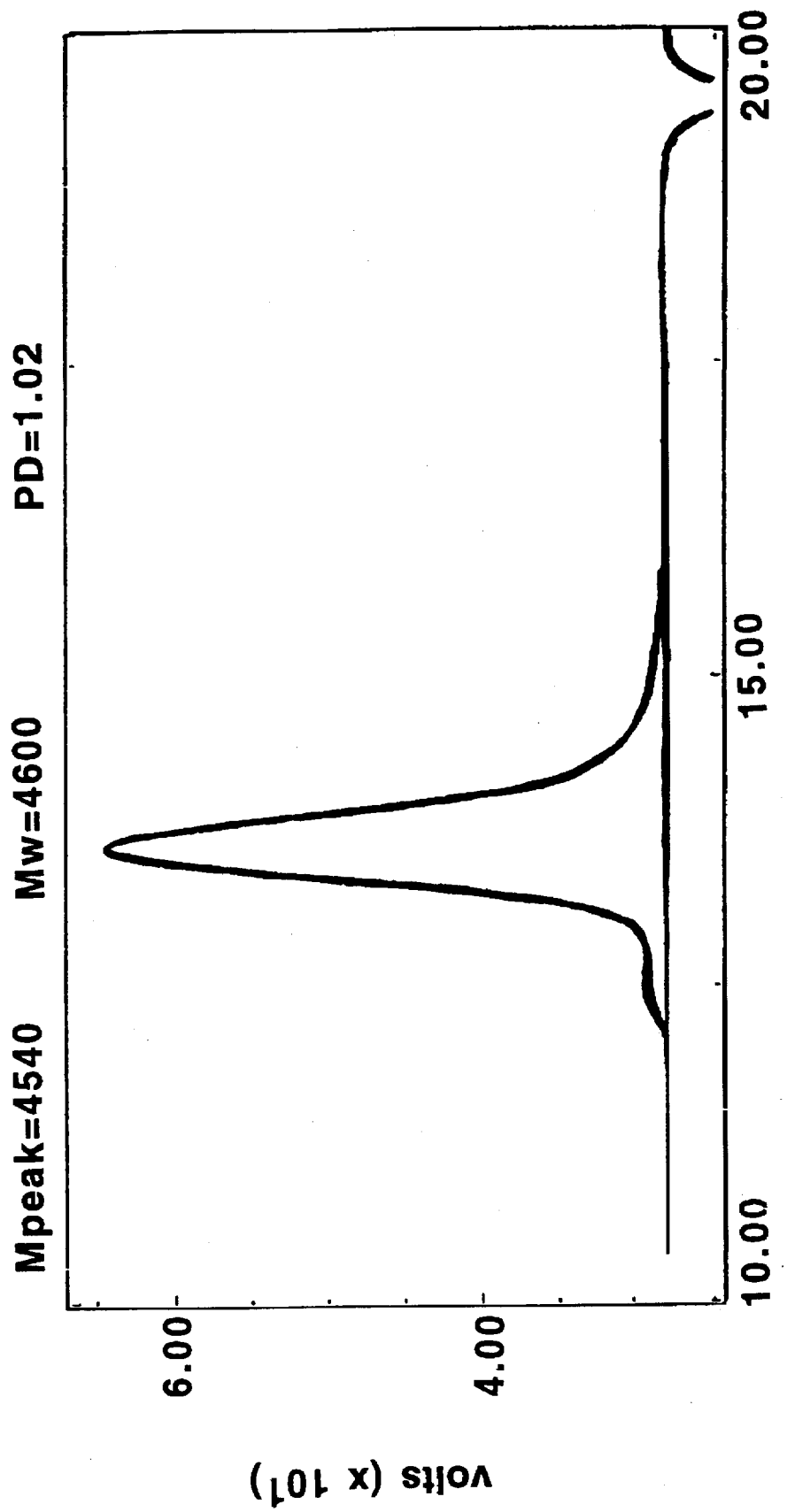
FIG. 6B is the high molecular weight purified fraction from super critical fractionation of CRL8131.

GPC chromatograms for these fractions are shown in FIG. 5 for the native CRL8131, FIG. 6A for a typical low molecular weight impurity and FIG. 6B for a typical purified high molecular weight fraction. This low molecular weight impurity accounted for between 10% and 12% of the total native CRL8131. The low molecular weight impurity in CRL8131 can be defined to contain molecules below 2500 daltons. As shown in FIG. 6A, the low molecular weight fraction obtained by supercritical fluid extraction contained mostly low molecular weight impurities although a small amount of higher molecular weight material was also extracted in this fraction. The typical purified high molecular weight shown in FIG. 6B showed a single peak with a peak molecular weight of approximately 4500, containing molecules ranging from 2500 to 6500 Daltons. The high molecular weight fraction has significantly low polydispersity compared to the native polymer.

EXAMPLE VIII

An experiment comparing the toxicity of low molecular weight impurities, the purified copolymer CRL8131 of the present invention and the native copolymer was conducted as follows:

The test system used was the isovolumetric, Langendorff-perfused rabbit heart. New Zealand White rabbits weighing approximately 3 kg were anesthetized with ketamine (20 mg/kg) and xylazine (4 mg/kg) injected intramuscularly. The blood was heparinized (250 units/kg intravenously) and via a thoracotomy, the heart was excised and placed in cold (4° C.) Krebs-Henseleit solution. After cannulation of the aorta, the heart was immediately flushed with a Krebs solution and suspended within the perfusion system. The time elapsed between the excision of the heart and the beginning of perfusion was 3 minutes.

A modified Langendorff isolated heart system was used in this study. The perfusate was pumped from a reservoir through a blood transfusion filter to the perfusion column. The heart was perfused via the cannulated aorta with a coronary perfusion pressure of (PP) approximately 60 mm Hg. This required a flow (Q) of 25 ml/min. Coronary vascular resistance was estimated as PP/Q. To obtain isovolumetric contractions, a latex balloon filled with fluid (2 to 5 ml) was inserted in the left ventricular cavity via an opening in the left atrium. A fluid filled catheter attached to the monitor was used to measure the left ventricular pressure (LVP). Left ventricular pressure and its electronically obtained first derivative (LV dP/dt) was continuously recorded. Heart rate was monitored via a cardiotachometer triggered by the LVP. The hearts were maintained at 37° C. and were not paced during the perfusion. They were allowed to recover for 35 to 40 minutes before the control measurements. The Krebs Henseleit buffer used for perfusing had the following composition in mM:

| | |
|---|---|
| Na | 155 |
| K | 5.6 |
| Cl | 138 |
| Ca | 2.16 |
| $PO_4$ | 1.19 |
| $HCO_3$ | 2.5 |
| Mg | 0.56 |
| Glucose | 11 |

The buffer was equilibrated with 95% $O_2$ and 5% $CO_2$, and maintained a pH of 7.4 before and during the experiment.

An equilibrium period of 50 minutes was observed to allow LVP, coronary perfusion pressure and heart rate to attain stable levels. Values of the variables were taken at −20 and −10 minutes. At time 0, the poloxamer or vehicle was infused (Harvard infusion pump) into the aortic cannula via a needle in a rubber cuff (2 ml/min). Changes that developed in LVP, heart rate and coronary perfusion were monitored at 5, 10, 15, 20, 30, 45, 60, and 90 minutes.

EXAMPLE IX

Figure 8:
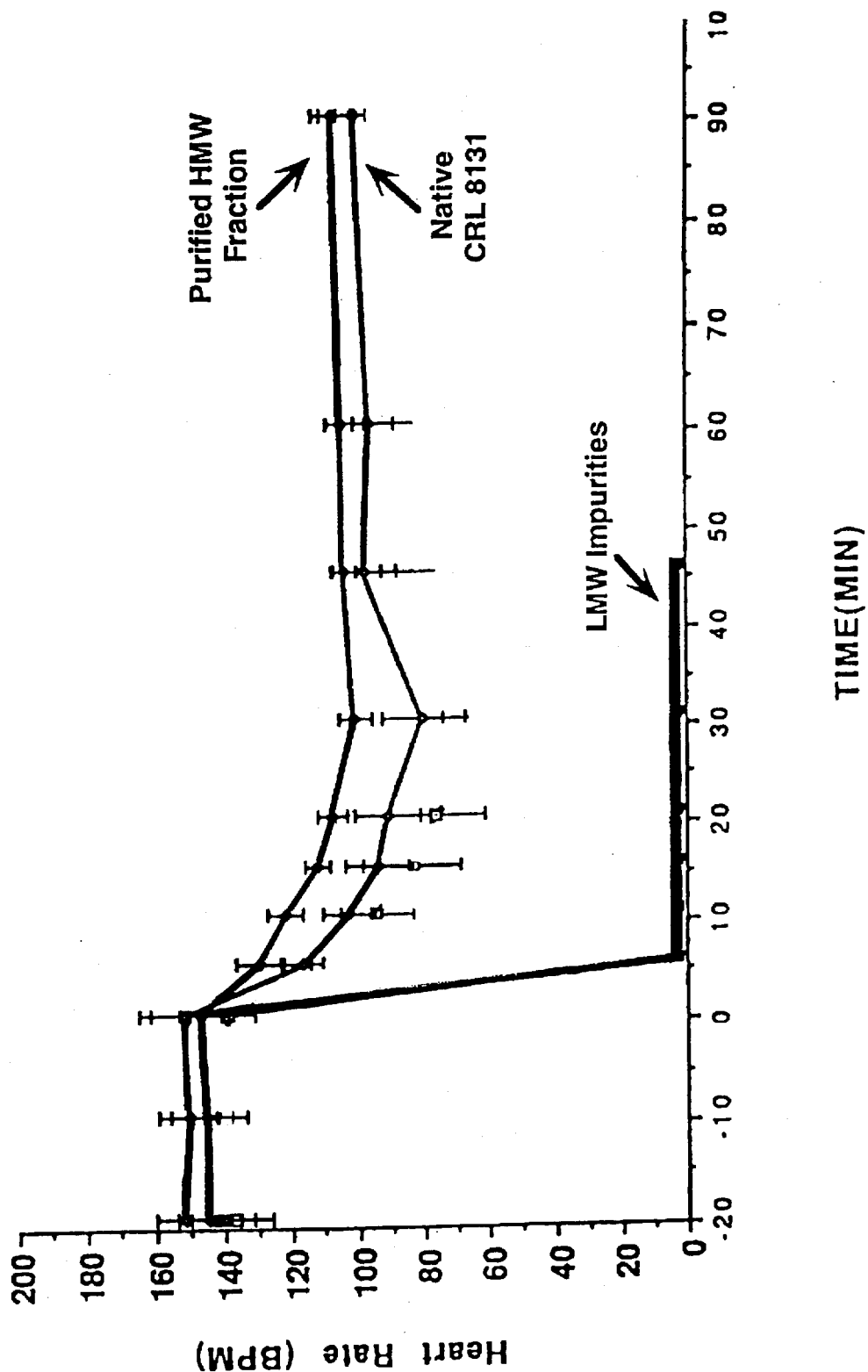
FIG. 8 compares mean heart rate in rabbits that have been treated with a native CRL8131, a fraction containing the low molecular weight impurities of native CRL8131 and purified CRL8131.

As shown in FIG. 8, the mean heart rate for the low molecular weight impurity is depressed to 0 beats per minute (BPM) after infusion of the fraction. Infusion of native CRL8131 showed a marked depression in heart rate. However, the infusion of high molecular weight fraction only showed a modest depression in heart rate.

Figure 9:
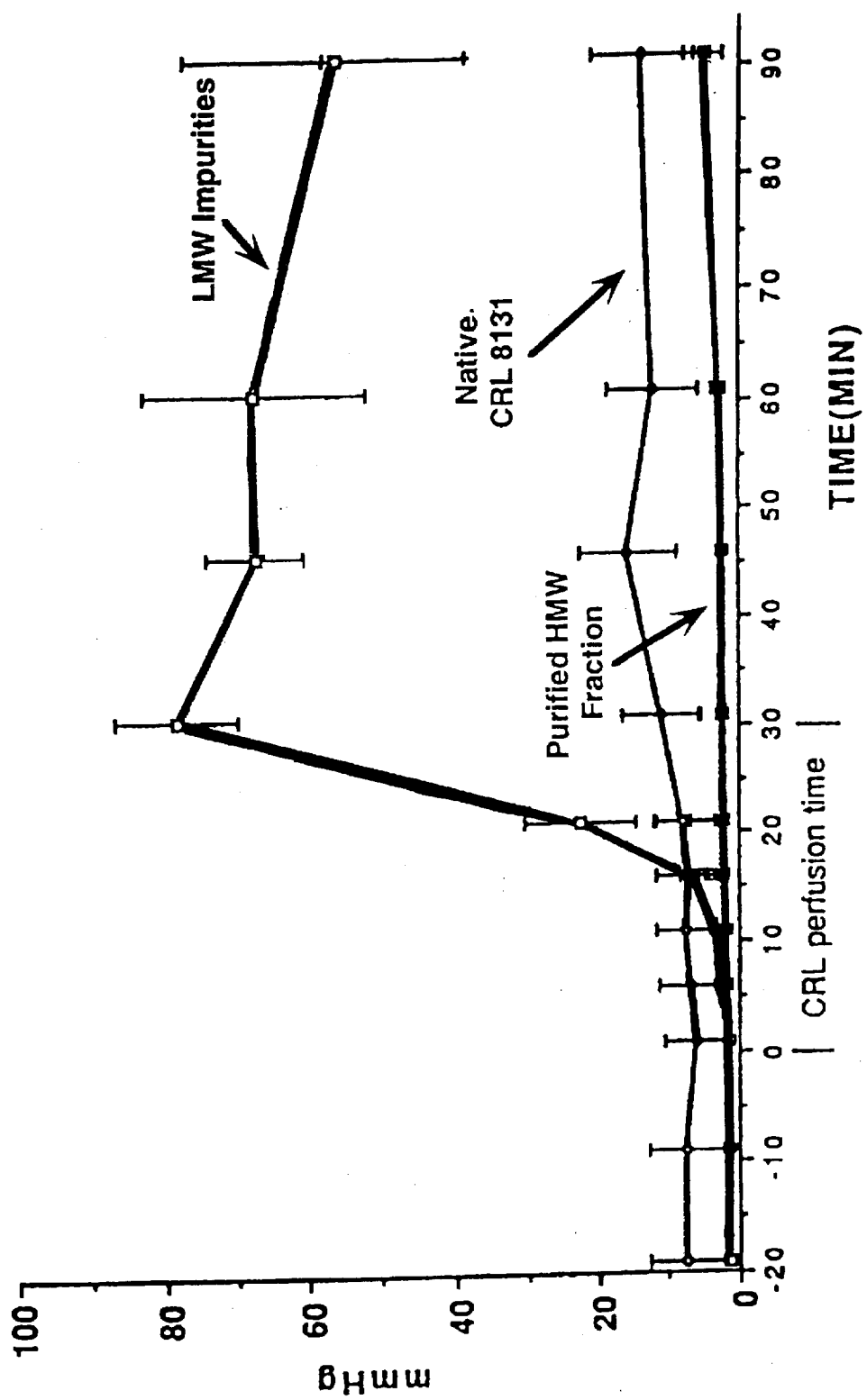
FIG. 9 compares left ventricular diastolic pressure of rabbit hearts that have been treated with a native CRL8131, a fraction containing the low molecular weight impuries of native CRL8131 and purified CRL8131.

The left ventricular diastolic pressure was measured after treatment with the three preparations. The results of these experiments are shown in FIG. 9. The purified high molecular weight fraction had no effect on left ventricular diastolic pressure. However, the low molecular weight impurity drastically increased left ventricular diastolic pressure from just over 0 to nearly 80 mmHg. The native CRL8131 caused a modest increase in left ventricular diastolic pressure.

Figure 10:
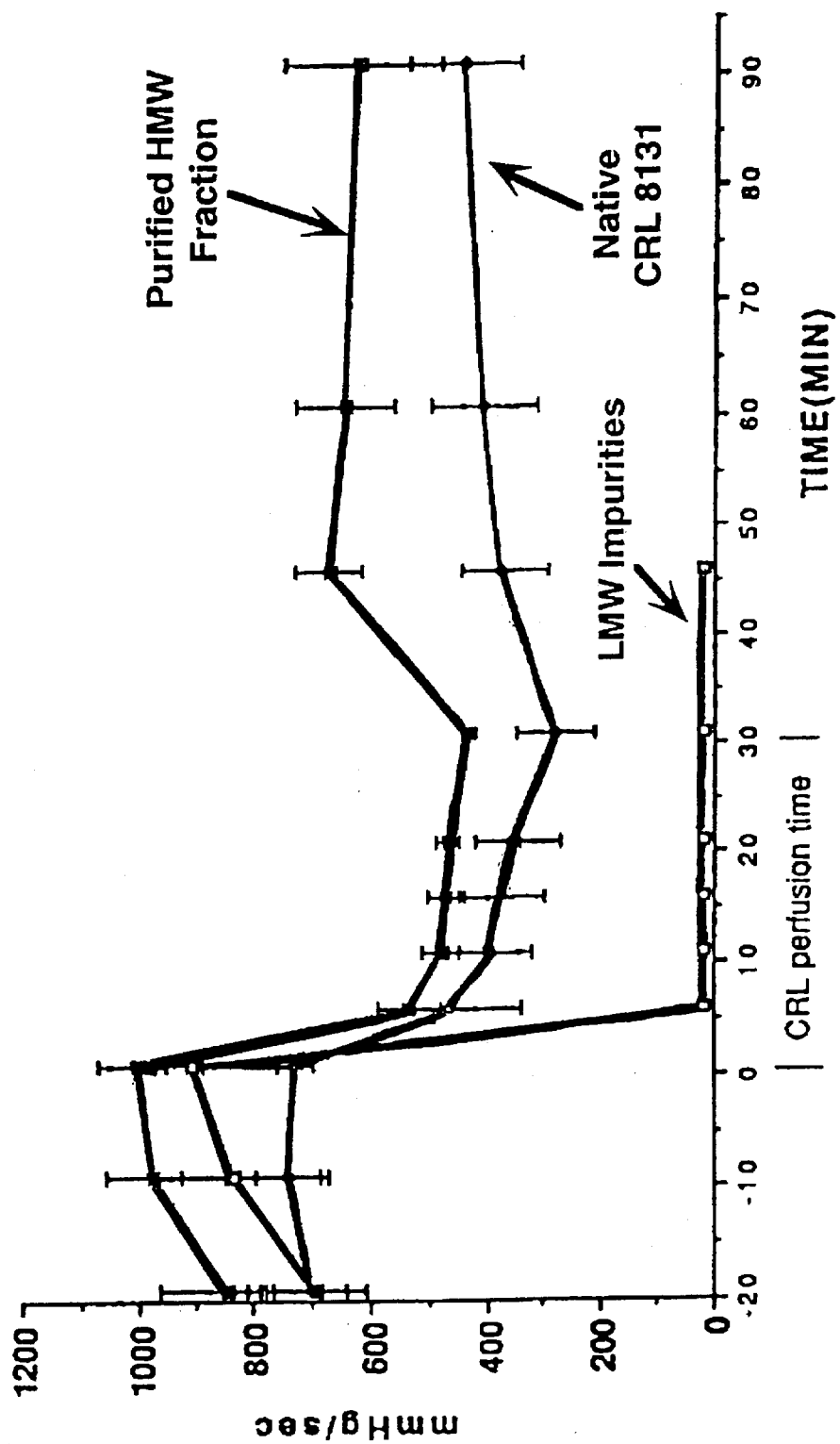
FIG. 10 compares the mean dP/dt of rabbit hearts that have been treated with a native CRL8131, a fraction containing the low molecular weight impurities of native CRL8131 and purified CRL8131.

Next, mean dP/dt was measured in the presence of each of the CRL8131 fractions (FIG. 10). Again, when low molecular weight impurity was administered to the animal, dP/dt initially increased slightly and then fell sharply to 0. The native CRL8131 also caused a decrease in mean dP/dt. The high molecular weight fraction caused a lesser decrease in the dP/dt.

As can be seen from these experiments, the low molecular weight impurity is quite toxic in all of the measurements made. The purified high molecular weight fraction shows the least toxicity when compared to low molecular weight impurity or to native CRL8131.

EXAMPLE X

Effect of CRL8131 fractions on *T. gondii* infection of macrophages

Macrophage monolayers were pretreated with the indicated copolymers for 18 hours. The macrophages were then infected with *Toxoplasma gondii* at a concentration of approximately two *T. gondii* organisms per macrophage. After one hour, nonphagocytized organisms were removed by washing and the medium plus the copolymer was replenished. Monolayers were fixed and enumerated at 24 hours after challenge. As a positive control, interferon-g, IFN-gamma, (murine recombinant at 200 U/ml) was added to macrophage monolayers 18 hours before challenge with Toxoplasma. These macrophages are activated by the IFN-gamma and readily kill Toxoplasma.

µg/ml for 0 to 24 hours as opposed to only 42% for the low molecular weight fractions.

EXAMPLE XI

Experiments were conducted to examine the in vivo activity against *Toxoplasma gondii* of the purified high molecular weight fraction and the low molecular weight impurity of CRL8131. Both fractions were formulated at 3% drug substance in a vehicle of two percent Tween 80 and 1 percent ethanol and appropriately diluted prior to administrated. A series of experiments were conducted with mice infected by intraperitoneal (IP) injection of tachyzoites of the R. H. strain of *T. gondii*.

Mice were Swiss-Webster females weighing 20 grams at the beginning of the experiment. Infection was IP with $10^3$ tachyzoites. Treatment with the fractions of CRL8131 was administered intraperitoneally. Treatment with the fractions of CRL8131 were administered interperitoneally at doses of 25 mg/kg/day. Treatment was initiated 24 hours after infection and continued every day for 10 days. Mice dying during treatment and after its discontinuation were examined for presence of *T. gondii* tachyzoites in intraperitoneal fluid.

Figure 11:
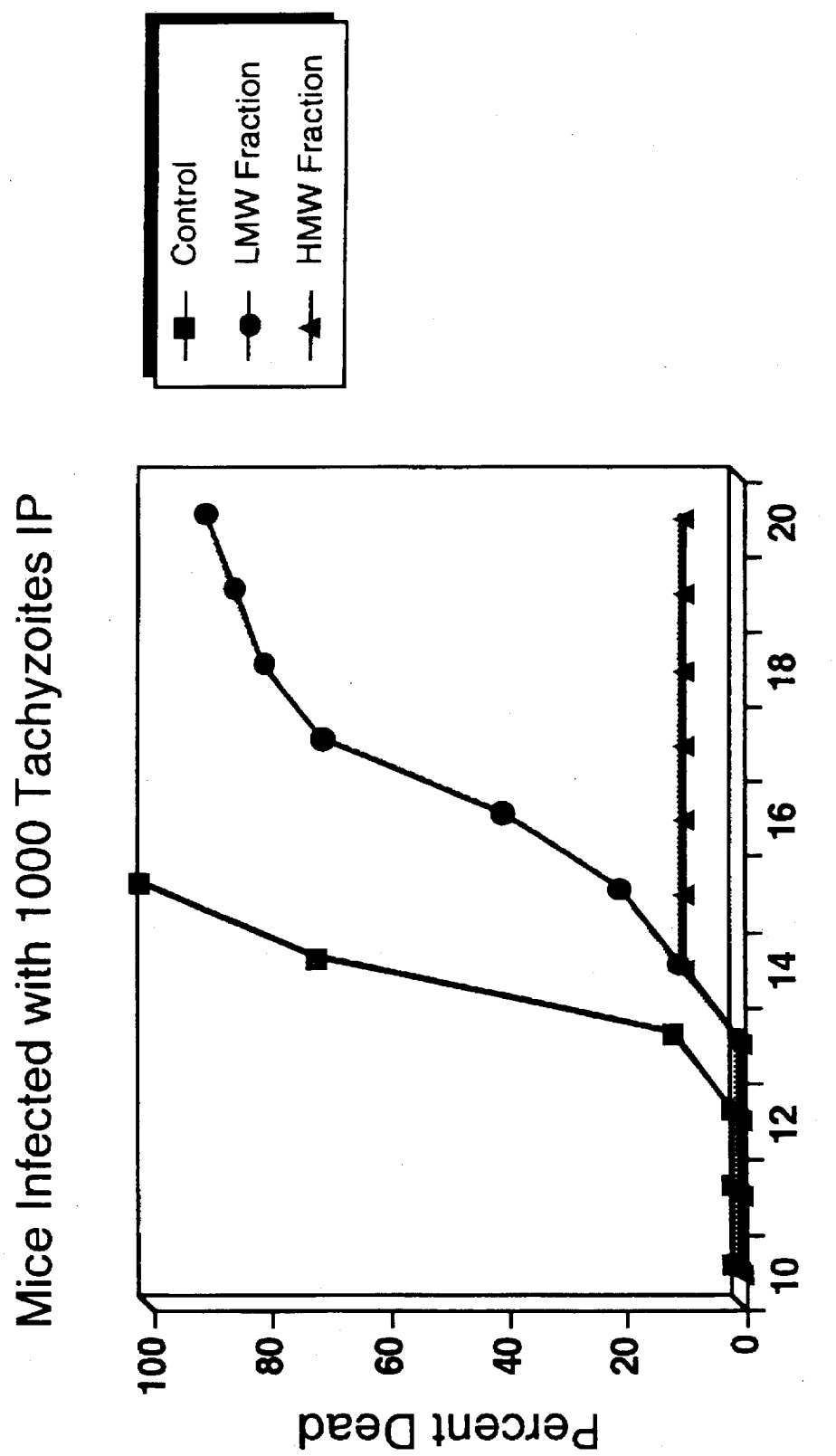
FIG. 11 compares survival of mice infected intraperitoneally with *Toxoplasma gondii* and treated with either purified CRL8131 or the low molecular weight impuries of native CRL8131.
Figure 12:
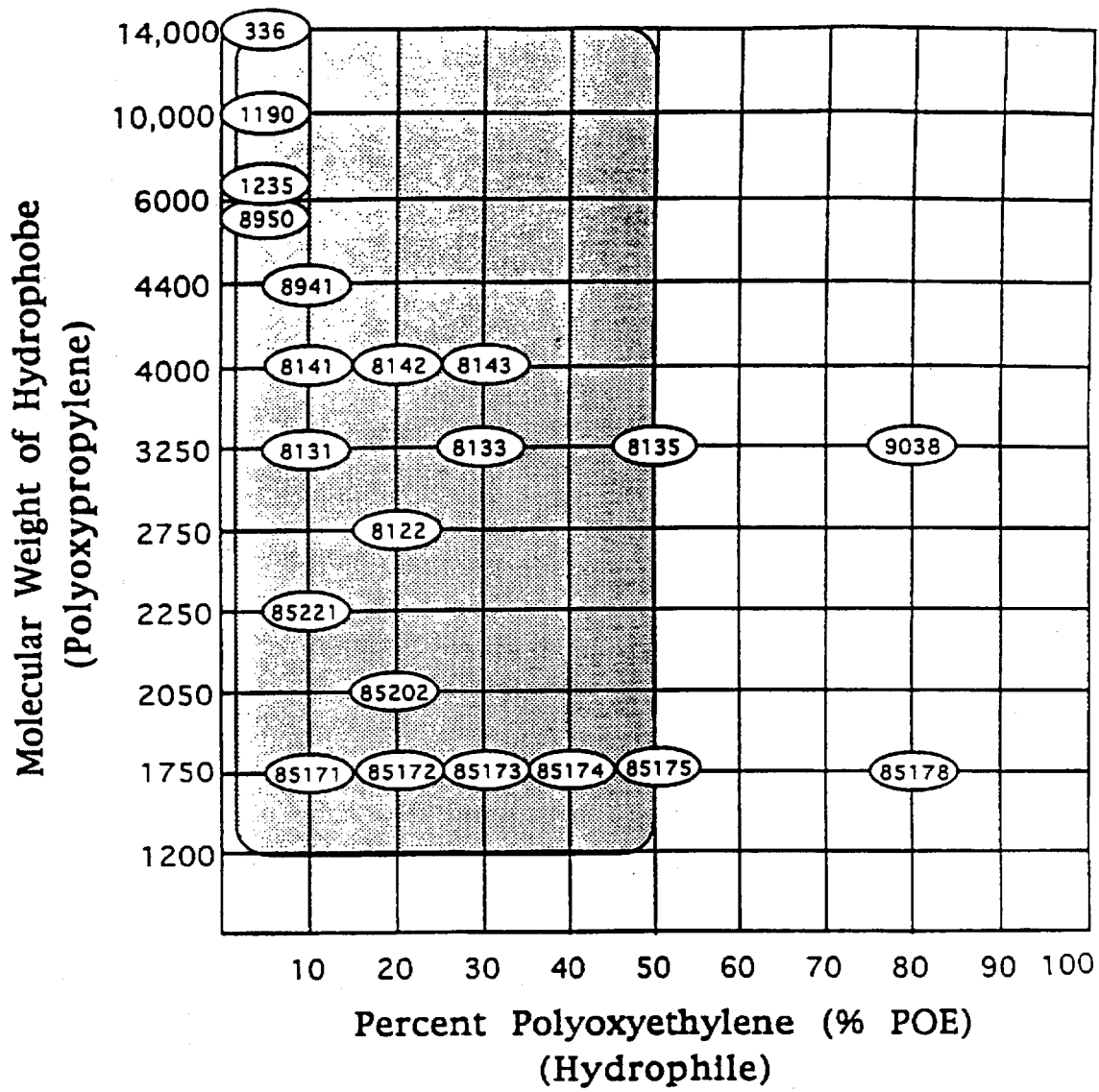
FIG. 12 is a grid illustrating block copolymers by molecular weight of hydrophobe and percent hydrophile.
Figure 13:
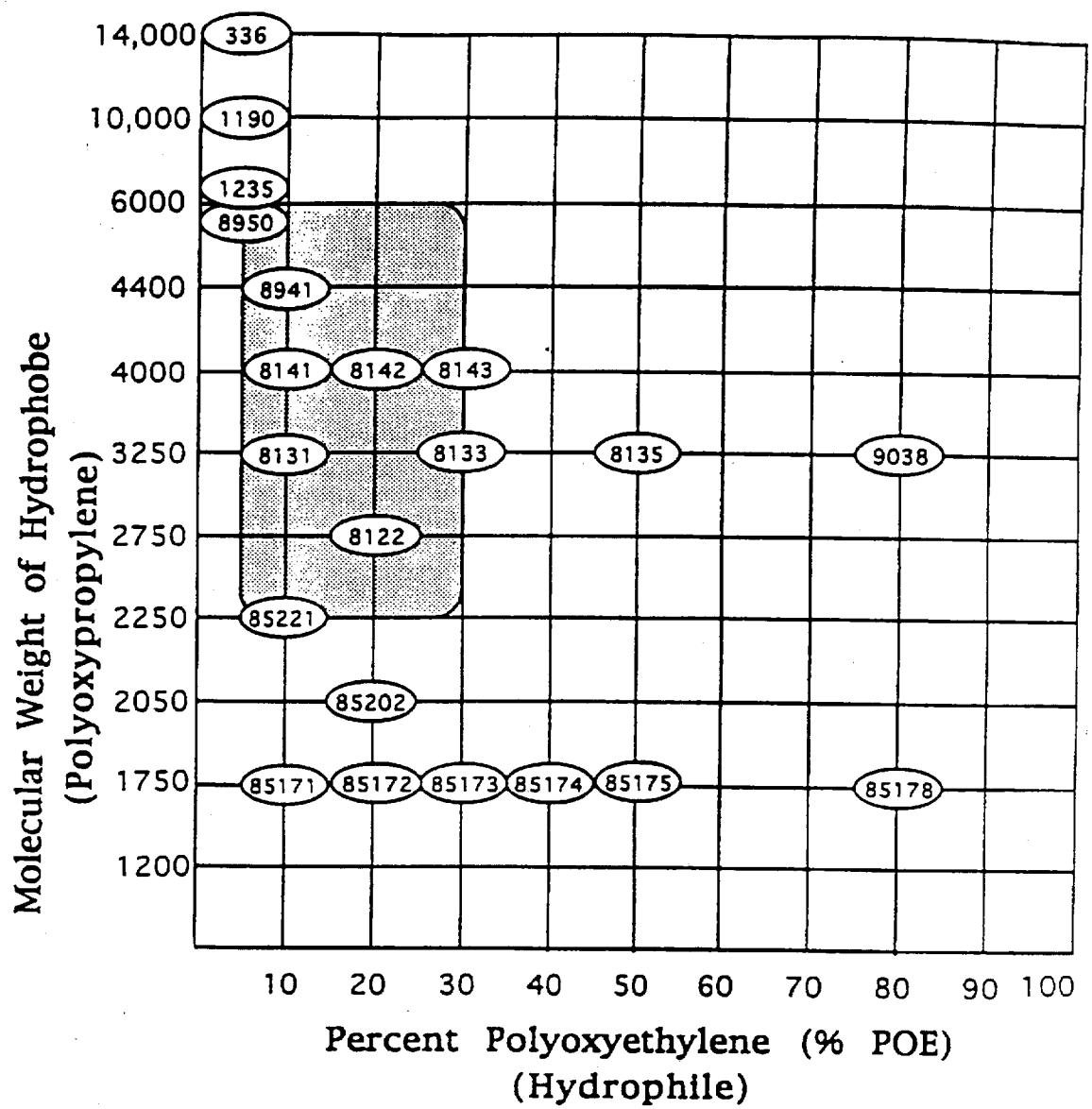
FIG. 13 is a grid illustrating preferred antiinfective block copolymers by molecular weight of hydrophobe and percent hydrophile.
Figure 14:
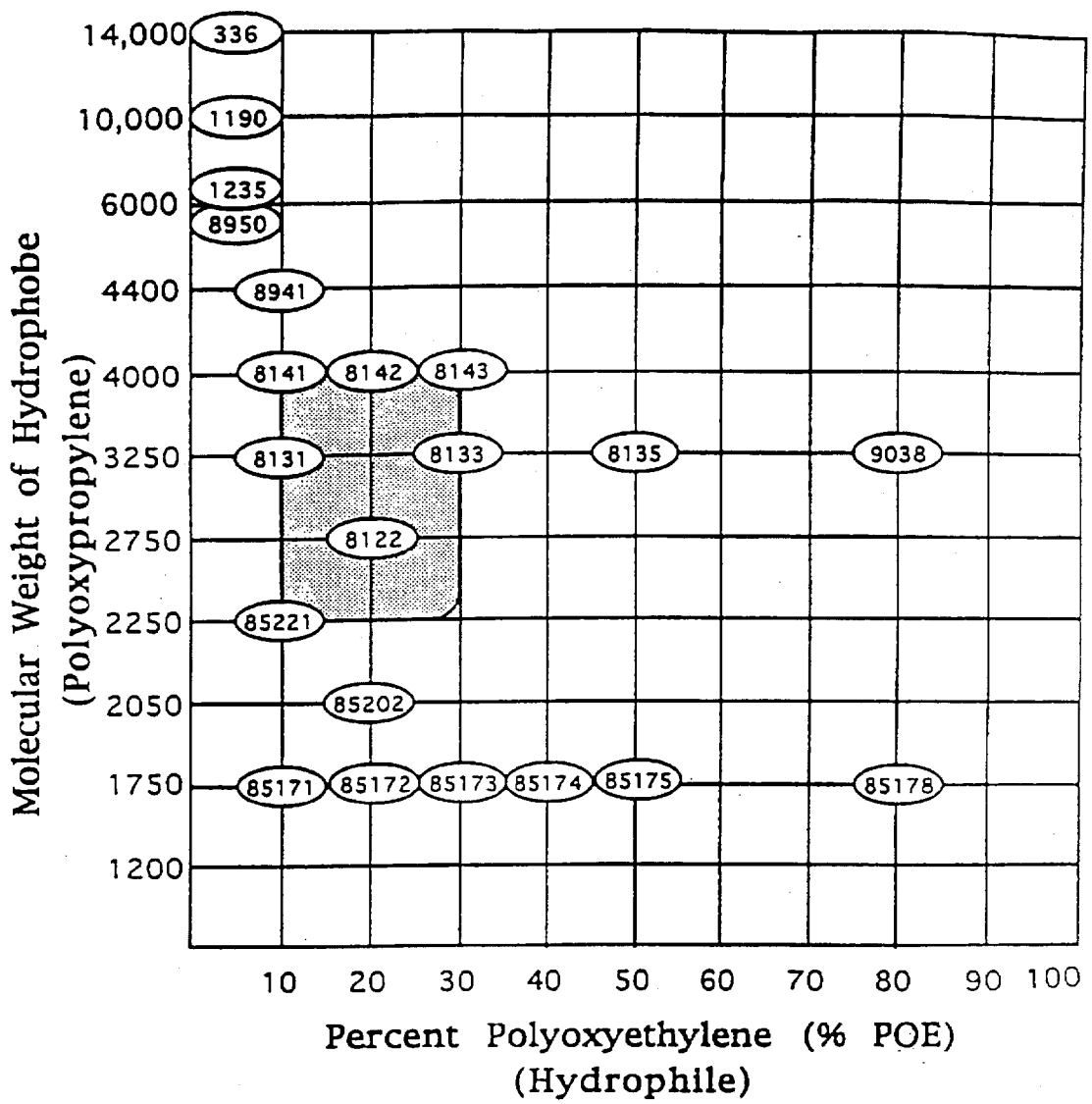
FIG. 14 is a grid illustrating other preferred antiinfective block copolymers by molecular weight of hydrophobe and percent hydrophile.
Figure 15:
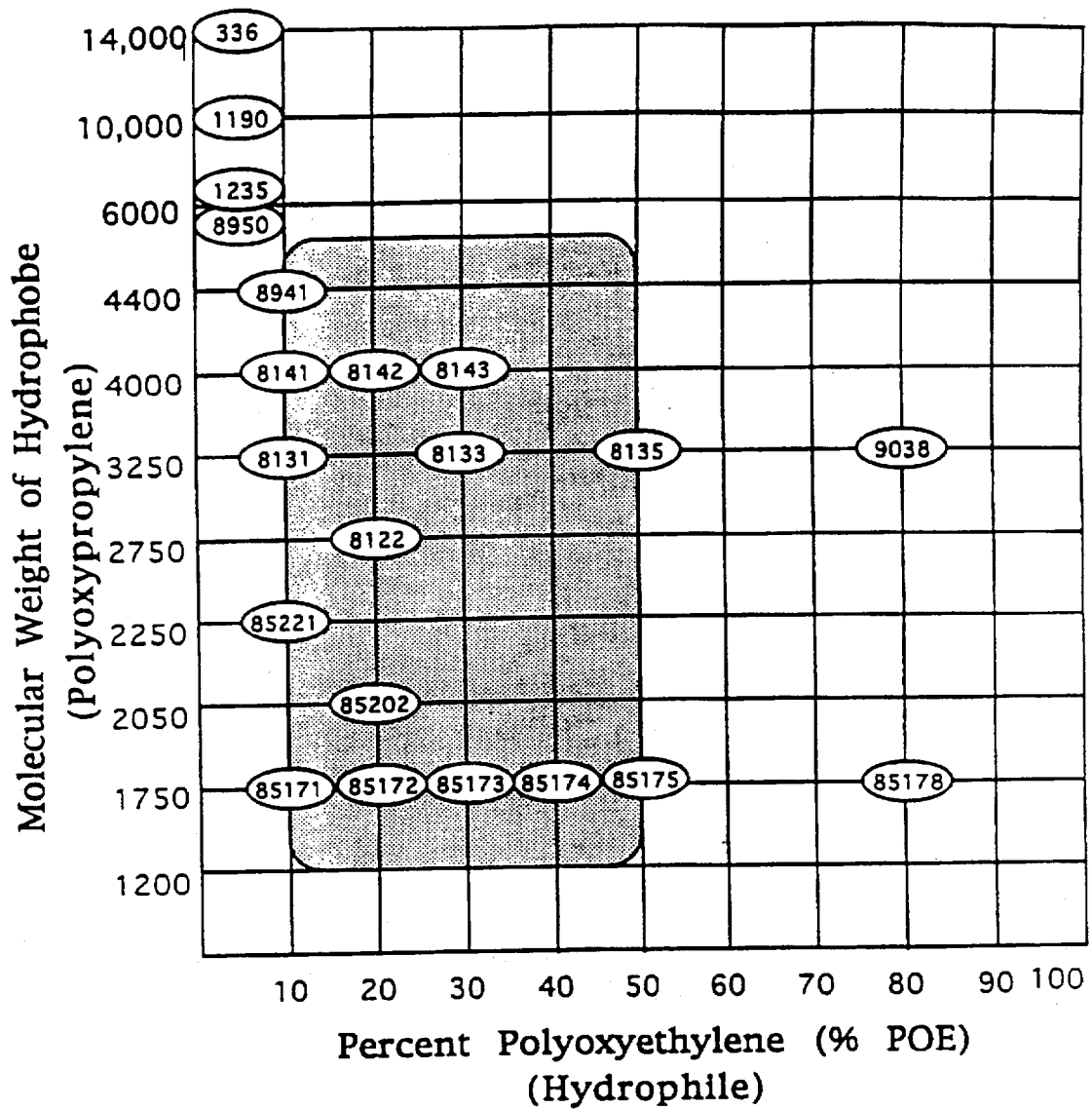
FIG. 15 is a grid illustrating yet other preferred antiinfective block copolymers by molecular weight of hydrophobe and percent hydrophile.
Figure 16:
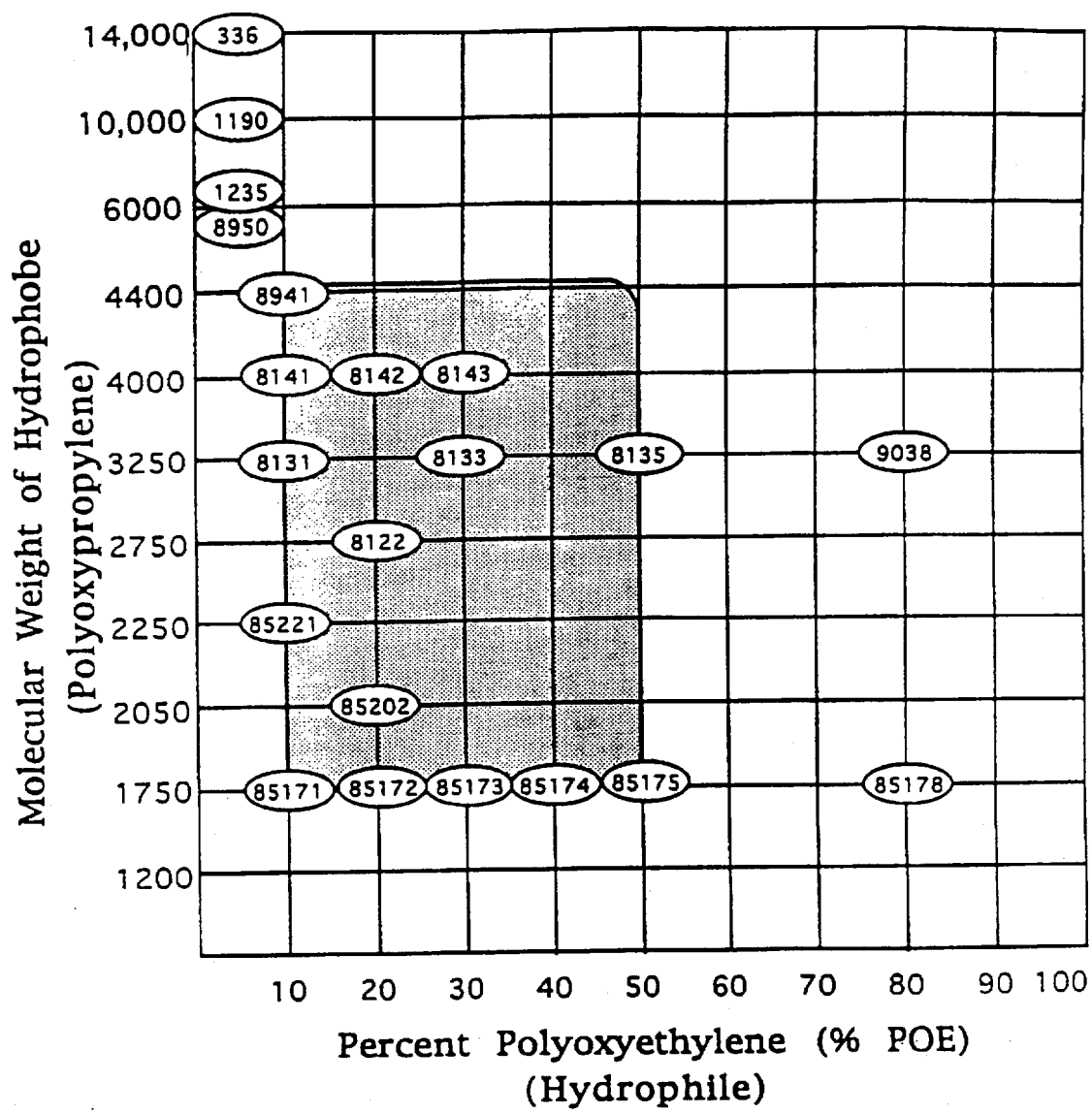
FIG. 16 is a grid illustrating still other preferred antiinfective block copolymers by molecular weight of hydrophobe and percent hydrophile.
Figure 17:
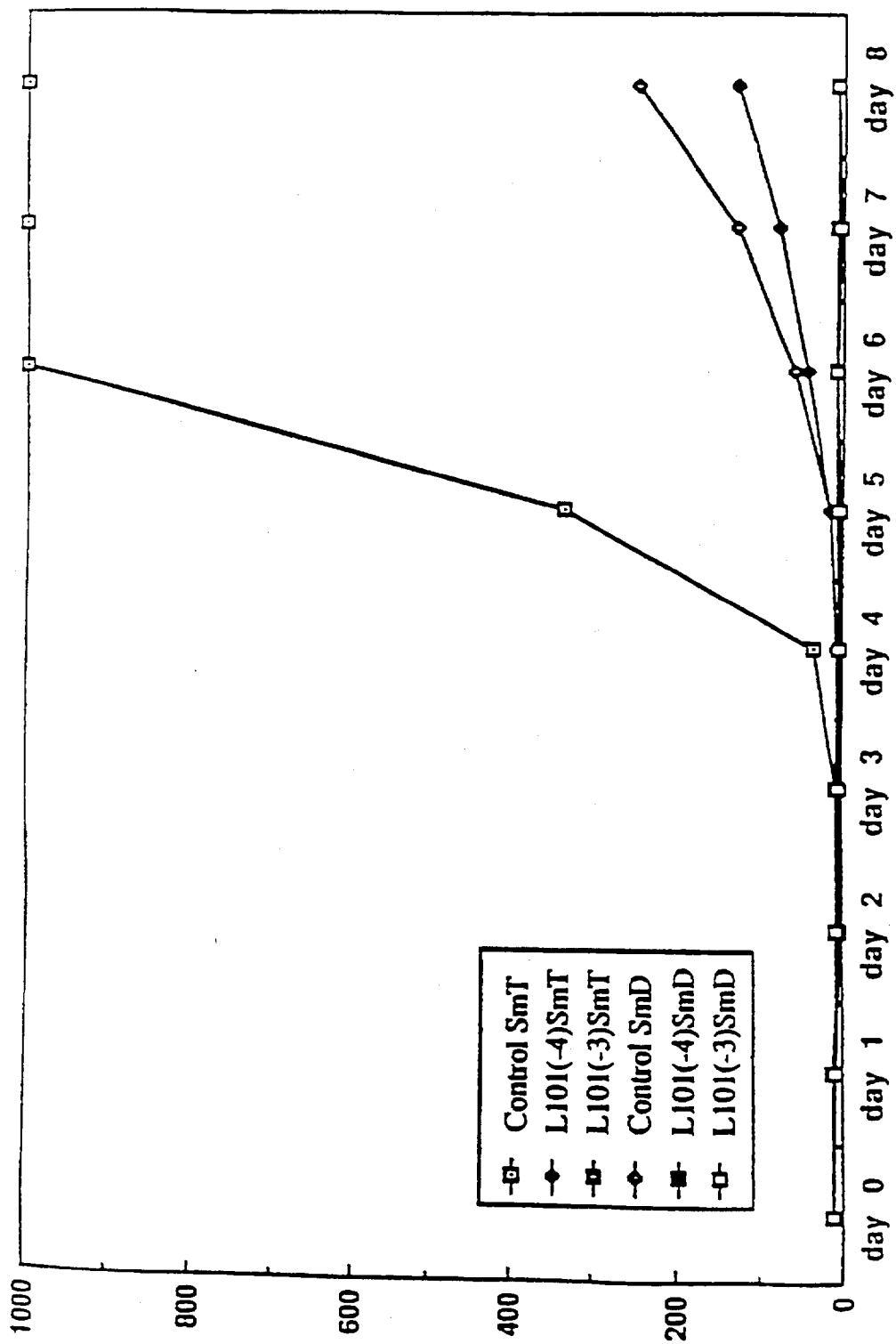
FIG. 17 is a graphical representation of the effect of CRL-8131 on the growth of *Mycobacterium avium*.
Figure 18:
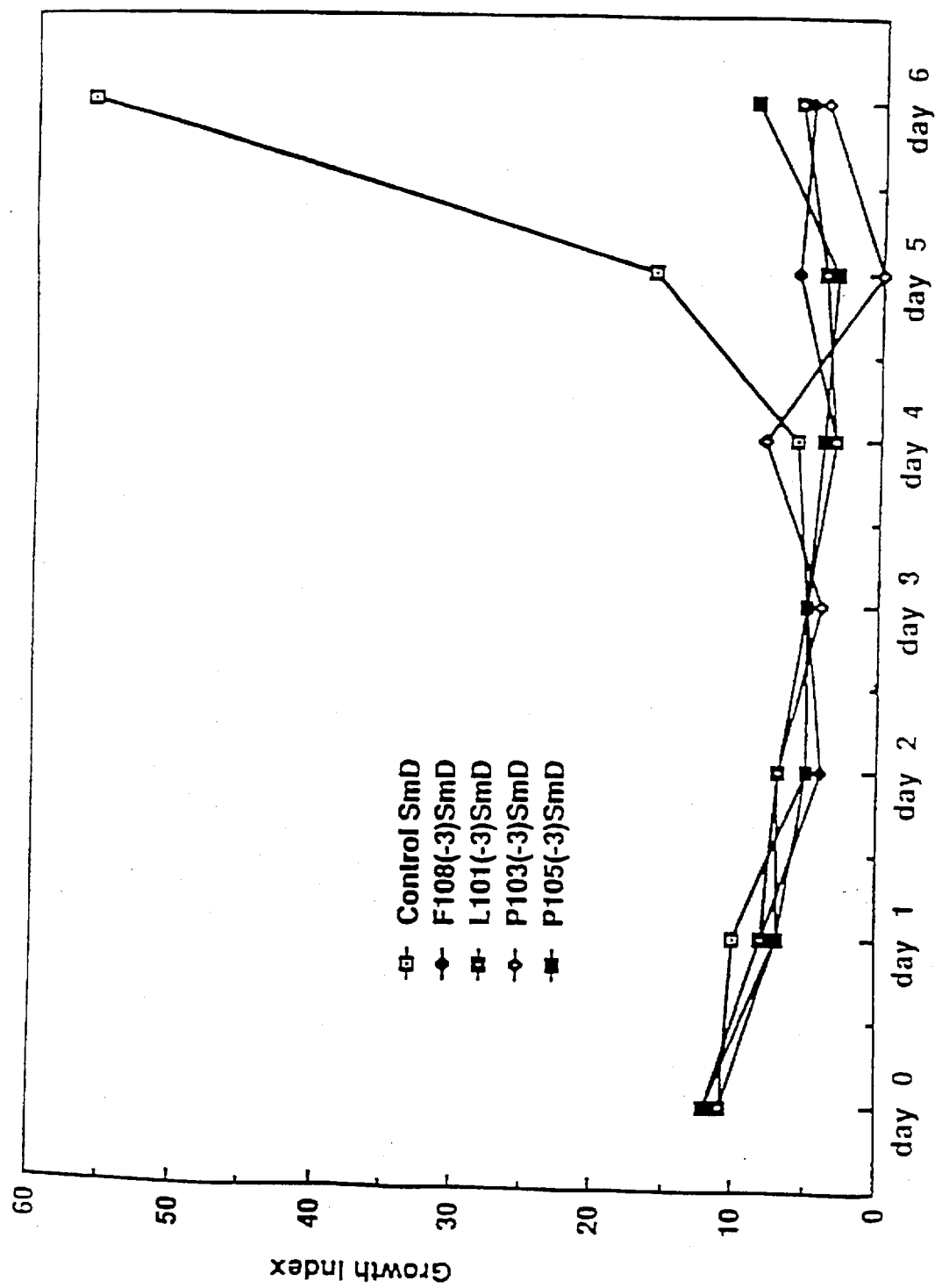
FIG. 18 is a graphical representation of the effect of CRL-9038, CRL-8131, CRL-8133 and CRL-8135 on the growth of *Mycobacterium avium*.
Figure 19:
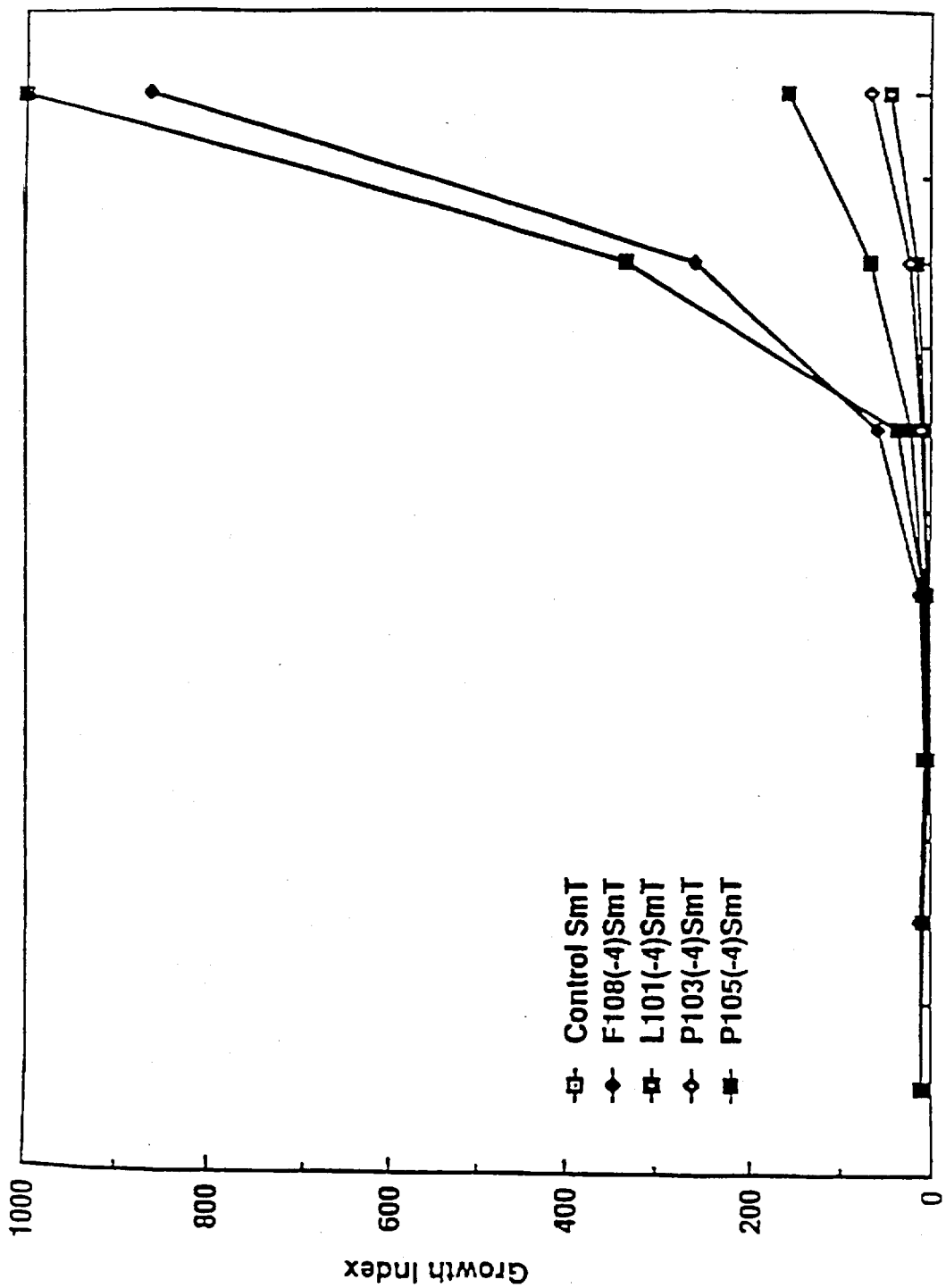
FIG. 19 is a graphical representation of the effect of CRL-8131, CRL-8133, and CRL-8135 on the growth of *Mycobacterium avium*.
Figure 20:
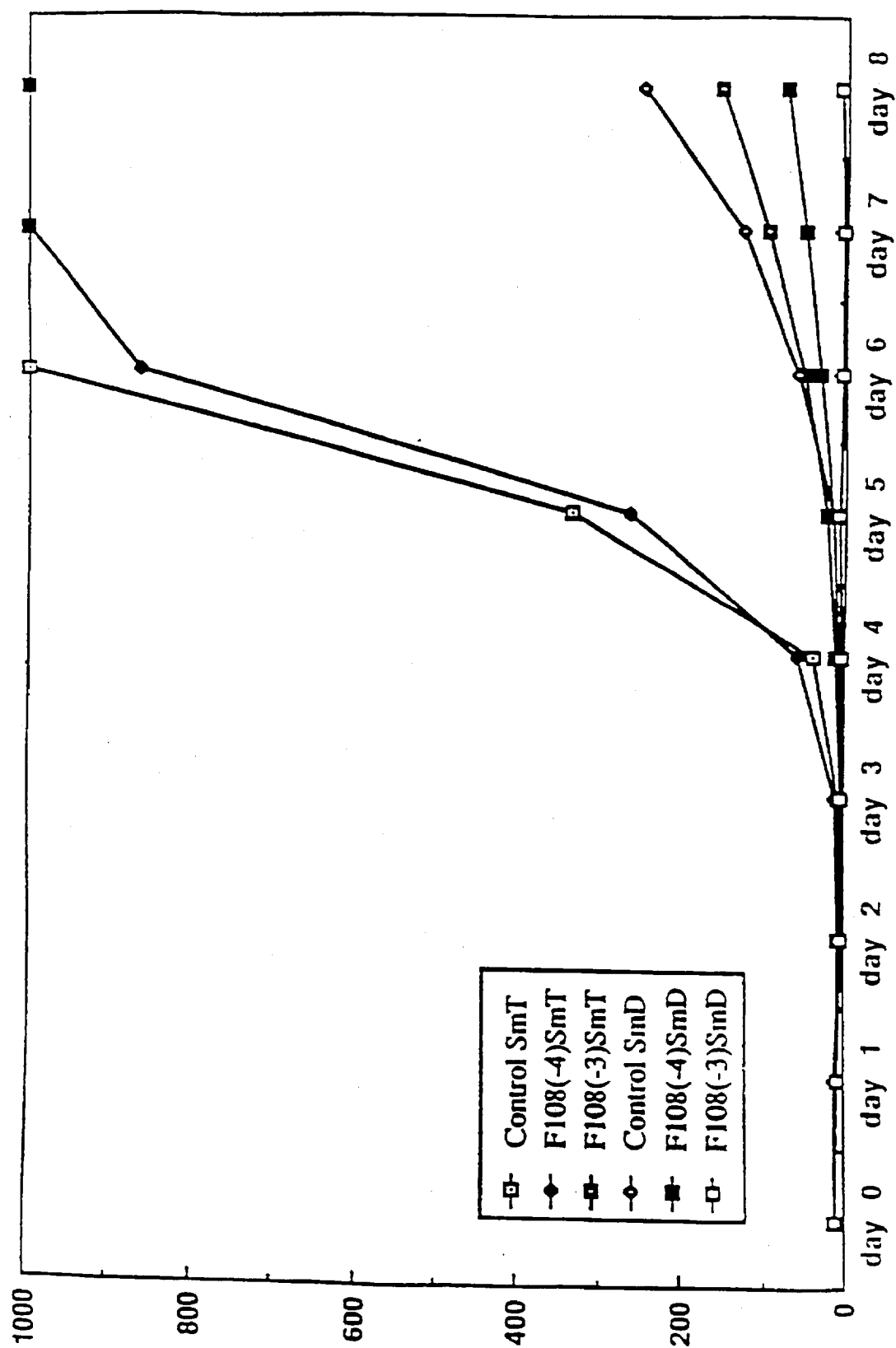
FIG. 20 is a graphical representation of the effect of CRL-9038 on the growth of *Mycobacterium avium*.
Figure 21:
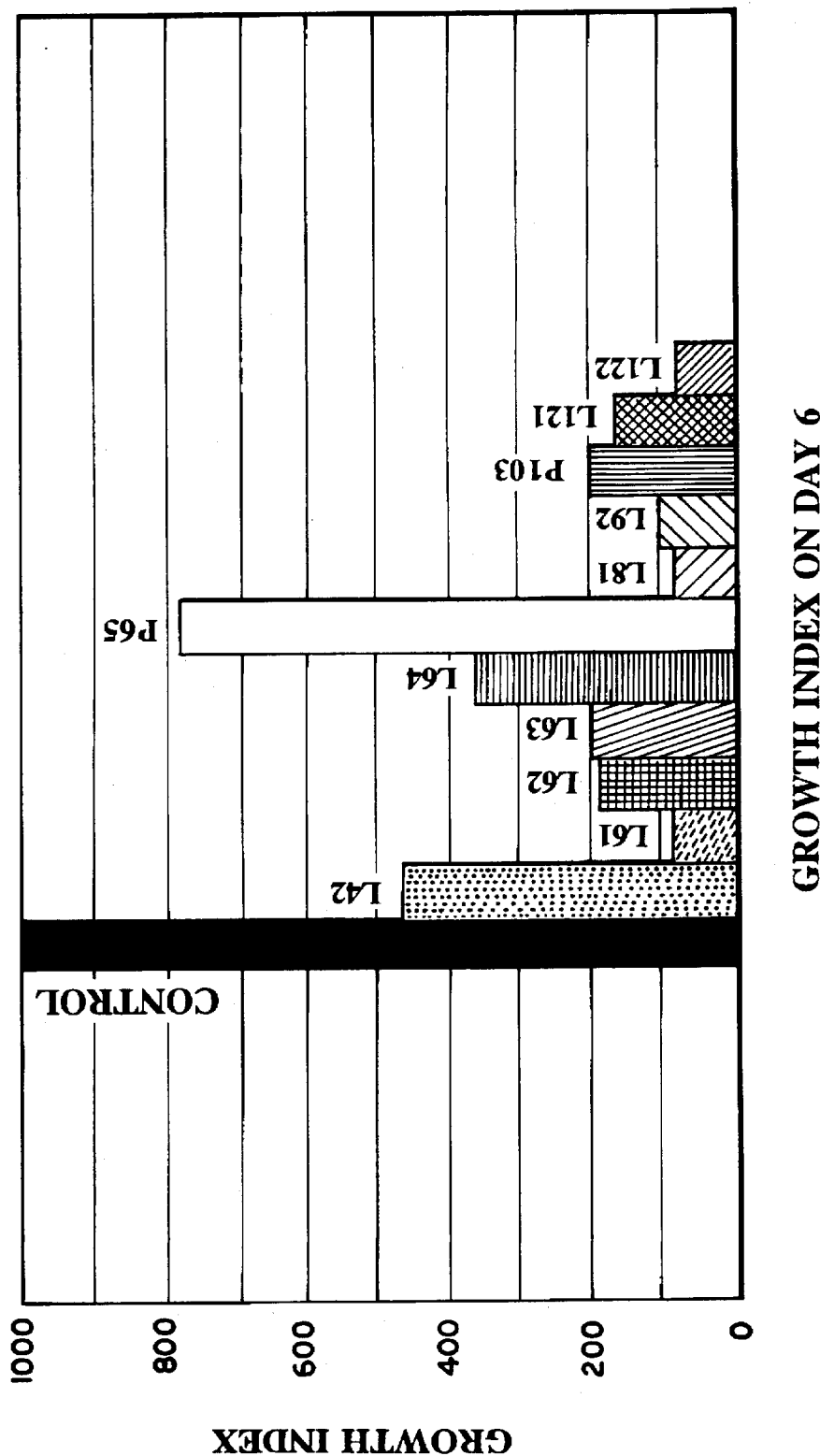
FIG. 21 is a graphical representation of the effect of 11 nonionic copolymers on the growth of *Mycobacterium avium*.
Figure 22:
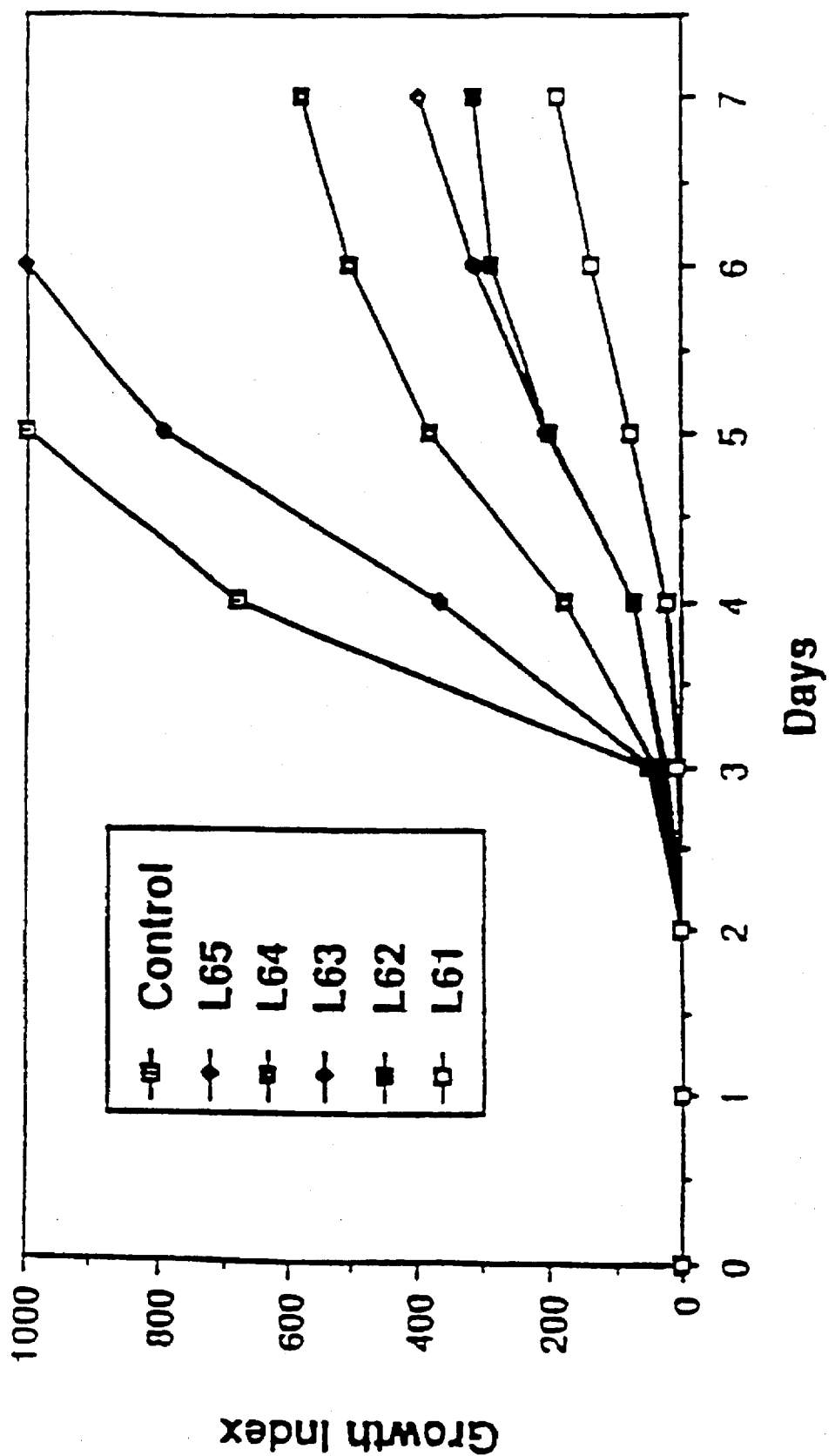
FIG. 22 is a graphical representation of the effect of several non-ionic copolymer on *Mycobacterium avium* growth.
Figure 23:
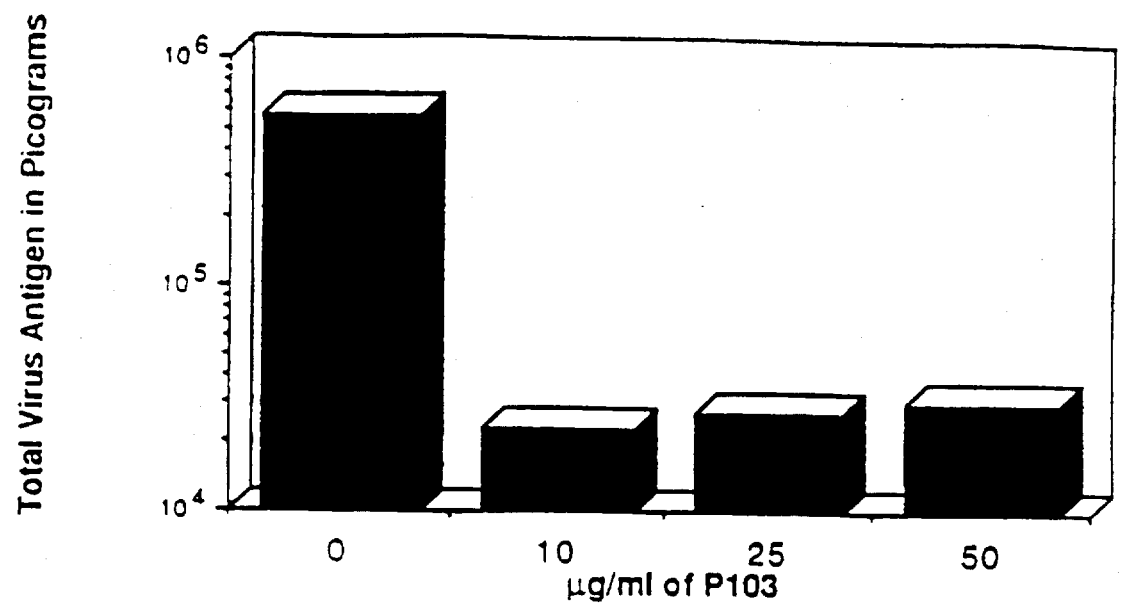
FIG. 23 is a graphical representation of the effect of the CRL-8133 copolymer on HIV infection in H9 cells.

Purified high molecular weight fraction of CRL8131, delivered IP, was clearly superior to the low molecular weight impurities of CRL8131 delivered IP in preventing death. (See FIG. 11). Although not shown, pretreatment of mice in this experiment did not significantly reduce mortality.

EXAMPLE XII

Smooth transparent (virulent) and smooth domed (nonvirulent) colonies of *Mycobacterium avium* derived from the same patient isolate were grown in 7H12 Middlebrook broth (Johnston Laboratories, Cockeysville, Md.). The Bactec 7H12 Middlebrook TB medium is an enriched Middlebrook 7H9 broth base which has been supplemented with bovine serum albumin (fraction V), catalase, casein hydrolysate and $^{14}$C-labeled fatty acids. Mycobacteria metabolize the $^{14}$C-labeled substrates and release $CO_2$ in air, thereby maintaining the recommended atmosphere. In

TABLE VI

| Fractions | Dose µg/ml | Incubation Time | Percent reduction in # of infected macs | Percent reduction in # Toxo/ infected macs | Percent reduction in # Toxo/100 macs |
|---|---|---|---|---|---|
| Control | 0 | n/a | 0 | 0 | 0 |
| Low Mol. Wt. Impurity | 2 | 0–24 hrs | 15 | 42 | 50 |
| Low Mol. Wt. Impurity | 10 | 2–4 hrs | 39 | 25 | 51 |
| Low Mol. Wt. Impurity | 50 | 2–4 hrs | 76 | 78 | 94 |
| High mol. wt. fraction (purified) | 2 | 0–24 hrs | 63 | 84 | 94 |
| High mol. wt. fraction (purified) | 10 | 2–4 hrs | 69 | 71 | 90 |
| High mol. wt. fraction (purified) | 50 | 2–4 hrs | 83 | 75 | 95 |

As shown in Table VI, high molecular weight fractions of CRL-8131 are most active against Toxoplasma. These fractions demonstrated organism reductions of greater than 90% after incubation with infected macrophages at 10 and 50 µg/ml for 2 to four hours. These high molecular weight fractions also demonstrated organism reductions of greater than 84% after incubation with infected macrophages at 2 addition, vials were inoculated with antimycobacterial agents and *M. tuberculosis* so that the evolution of $CO_2$ can be correlated to the susceptibility or resistance of the organism to the drug. When the mycobacteria grow in the medium containing $^{14}$C-labeled fatty acid, they utilize the fatty acid and $CO_2$ is produced. The production of $CO_2$ can be detected quantitatively, reflecting the rate and amount of growth occurring in the vial, and is expressed in terms of the "growth index". If an anti-tuberculosis drug is added to the medium, suppression of growth occurs in the case of susceptible organisms which can be detected by either a decline or a very small increase of the growth index as compared to the control. However, if the organisms are resistant, no suppression occurs in the rate of increase of the growth index on daily testing.

To determine the 1% proportion of resistance, the inoculum in the control vial is one hundred fold less than the inoculum used for drug containing vials. Growth index readings are taken each day after inoculation and the increase in growth index over that of the previous day, is compared for the control vial and the vials containing drugs. If the daily increase in growth index, called delta growth index, in the drug vial is equal to or greater than that in the control vial, the test organisms are considered resistant to the drug. For a susceptible organism, the daily increase in the growth index for the control would be much higher than for the drug vial.

Cultures were incubated at 36° C. and checked daily with a Bactec 460TB (Johnston Laboratories, Cockeysville, Md.) instrument with a self-contained laminar flow hood. A growth index was determined by measuring the amount of $^{14}C$ released into the atmosphere of the container as a result of mycobacterial utilization of $^{14}C$-labeled fatty acids.

*Mycobacterium avium* organisms were treated with one of four nonionic block copolymers, designated CRL-8131, CRL-8133, CRL-8135, and CRL-9038. These copolymers have identical hydrophobic portions and differ only in the length of the polyoxyethylene (hydrophilic) chains. These four molecules range in size from 3,600 to 14,000 daltons and the molecular weight attributable to the polyoxypropylene portion of each molecule is approximately 3,250. The hydrophilic portion of each molecule is 10% for CRL-8131, 30% for CRL-8133, 50% for CRL-8135, and 80% for CRL-9038. Each of the candidate anti-mycobacterial copolymers were mixed with the Middlebrook tuberculosis medium at concentration of $1 \times 10^{-3}M$ and $1 \times 10^{-4}M$.

A grid illustrating the range of copolymers encompassed by the present invention based upon the molecular weight of the hydrophobe portion and the percent hydrophile, and showing selected nonionic block copolymers appears as FIG. 12.

It has been discovered that the copolymers most effective as antiinfectives fall within the indicated regions of the copolymer grid as shown in FIGS. 13, 14, 15, and 16.

As shown in FIGS. 17, 18, and 19, a significant reduction in growth rate of both smooth transparent (SmT) and smooth domed (SmD) colonies treated with CRL-8131, CRL-8133, and CRL-8135 occurred. As shown in FIG. 20, smooth transparent (virulent) colonies treated with CRL-9038 in a concentration of $1\times10^{-4}$M did not inhibit the growth of *Mycobacterium avium*; however, an CRL-9038 concentration of $1\times10^{-3}$M showed some suppression of bacterial growth.

EXAMPLE XIII

Smooth transparent (virulent) and smooth domed (nonvirulent) colonies of *Mycobacterium avium* derived from the same patient isolate were grown in BACTEC 7H12 Middlebrook broth. A growth index was determined by measuring the amount of $^{14}C$ released into the atmosphere of the container as a result of mycobacterial utilization of $^{14}C$-labeled fatty acid as described in Example I.

*Mycobacterium avium* organisms treated with one of fourteen nonionic block copolymers, designated L42, CRL-85171, CRL-85172, CRL-85173, CRL-85174, CRL-85175, CRL-85202, CRL-85221, CRL-8122, CRL-8131, CRL-8133, CRL-8141, CRL-8142, and CRL-8143. Each copolymer has a polyoxyethylene portion ranging from 5% to 50% of the total molecule. The molecular weight of the polyoxypropylene portion of each molecule ranges from approximately 1,200 to approximately 4,000. The physical characteristics of each copolymer are summarized in Table II.

As shown in FIG. 21, there was a significant reduction in growth rate of smooth transparent colonies treated with all the copolymers tested. CRL-85175 and L42 exhibited only moderate inhibition.

EXAMPLE XIV

A correlation between increasing hydrophobicity of the copolymer and inhibition of *M. avium* growth is shown in FIG. 22. The copolymers having a polyoxypropylene molecular weight of 1750 were tested for inhibition of *M. avium*. The copolymers tested are CRL-85171, CRL-85172, CRL-85173, CRL-85174, and CRL-85175.

As shown in FIG. 22, inhibition of mycobacterial growth specifically correlates with the molecular structure of the copolymers. The low molecular weight copolymers which have only a small percentage of hydrophil appear to inhibit *M. avium* growth more than copolymers which are more hydrophilic.

EXAMPLE XV

The effectiveness of P103 copolymer is examined in preventing HIV replication in H9 cells using a high multiplicity of viral infection. The infections are conducted in the following manner: $10^5$ H9 cells in 1 ml medium containing $1.89\times10^{-2}$ picogram T24 viral antigen per cell, and either 0, 10, 25, or 50 μg of CRL-8133, are incubated at 37° C. in 5% $CO_2$ for one hour. After this time, the cells are pelleted at 3,000 rpm and washed to remove access non-adsorbed virus. The cells are plated in medium in dishes containing wells of 1 cm diameter. The cultures and the controls, all done in triplicate, are incubated at 37° C., 5% $CO_2$, and the volume in each well is maintained at a constant volume of 1 ml. The media contains either 10, 25, or 50 μg per ml of CRL-8133. Virus yields in terms of total picogram of T24 HIV antigen and cell counts are determined on day seven of the incubation period. Cell viability is determined by trypan blue exclusion.

As can be seen in FIG. 23, there is at least a one and one/half log reduction in virus yield evident at the low concentration of 10 μg per ml of CRL-8133. Furthermore, the higher concentrations of CRL-8133 did not appear to mediate further reductions in viral replication.

According to these results, the CRL-8133 copolymer is considered an effective inhibitor of HIV application in H9 cells.

EXAMPLE XVI

Compounds

Samples of AZT was synthesized and purified by a modification of the method of Lin and Prusoff (Lin, T. -S, and W. H. Prusoff. 1978. Synthesis and biological activity of several amino analogs of thymidine. *J. Med. Chem.* 21:109–112).

Antiviral studies

Cells:

Human peripheral blood mononuclear cells (PBMC) from healthy HIV-1 seronegative and hepatitis B virus seronegative donors were isolated by Ficoll-Hypaque discontinuous gradient centrifugation at 1,000× g for 30 minutes, washed twice in phosphate-buffered saline (pH 7.2; PBS), and pelleted at 300× g for 10 minutes. Before infection, the cells were stimulated by phytohemagglutinin (PHA) at a concentration of 16.7 µg/ml for three days in RPMI 1640 medium supplemented with 15% heat-inactivated fetal calf serum, 1.5 mM L-glutamine, penicillin (100 U/ml), streptomycin (100 µg/ml), and 4 mM sodium bicarbonate buffer.

Viruses

HIV-1 (strain LAV-1) was obtained from Dr. P. Feorino (Centers for Disease Control, Atlanta, Ga.). The virus was propagated in human PBMC using RPMI 1640 medium, as described previously (McDougal, J. S., S. P. Cort, M. S. Kennedy, C. D. Cabridilla, P. M. Feorino, D. P. Francis, D. Hicks, V. S. Kalyanaramen, and L. S. Martin. 1985. Immunoassay for the detection and quantitation of infectious human retrovirus, lymphadenopathy-associated virus (LAV). *J. Immun. Meth.* 76:171–183) without PHA or fungizone and supplemented with 7% v/v interleukin-2 (Advanced Biotechnologies, Silver Spring, Md.), 7 µg/ml DEAE-dextran (Pharmacia, Uppsala, Sweden), and 370 U/ml anti-human leukocyte (alpha) interferon (ICN, Lisle, IL). Virus obtained from cell-free culture supernatant was titrated and stored in aliquots at −70° C. until use.

Inhibition of virus replication in human PBMC

Uninfected PHA-stimulated human PBMC were uniformly distributed among 25 cm$^2$ flasks to give a 5 ml suspension containing about $2\times10^6$ cells/ml. Suitable dilutions of virus were added to infect the cultures. The mean reverse transcriptase (RT) activity of the inocula was 50,000 dpm/ml corresponding to about 100 TCID$_{50}$, as determined by Groopman et al. (Groopman J. E., P. M. Benz, R. Ferriani, K. Mayer, J. D. Allan, and L. A. Weymouth. 1987. Characterization of serum neutralization response to the human immunodeficiency virus (HIV). *AIDS Res. Human Retro.* 3:71–85). The drugs at twice their final concentrations in 5 ml of RPMI 1640 medium, supplemented as described above, were added to the cultures. Uninfected and untreated PBMC at equivalent cell densities were grown in parallel as controls. The cultures were maintained in a humidified 5% CO$_2$-95% air incubator at 37° C. for six days after infection at which point all cultures were sampled for supernatant RT activity. Previous studies had indicated that maximum RT levels were obtained at that time.

Reverse Transcriptase (RT) activity assay

Six ml supernatant from each culture was clarified from cells at 300× g for 10 minutes. Virus particles were pelleted from 5 ml samples at 40,000 rpm for 30 minutes using a Beckman 70.1 Ti rotor and suspended in 200 µl of virus disrupting buffer (50 mM Tris-HCl, pH 7.8, 800 mM NaCl, 20% glycerol, 0.5 mM phenylmethyl sulfonyl fluoride, and 0.5% Triton X-100).

The RT assay was performed in 96-well microtiter plates, as described by Spira et al. (Spira, T. J., L. H. Bozeman, R. C. Holman, D. T. Warfield, S. K. Phillips, and P. M. Feorino. 1987. Micromethod for assaying the reverse transcriptase of LAV-HTLV-III/lymphadenopathy-associated virus. *J. Clin. Microbiol.* 25:97–99). The reaction mixture, which contained 50 mM Tris-HCl pH 7.8, 9 mM MgCl$_2$, 5 mM dithiothreitol, 4.7 µg/ml (rA)$_n$·(dT)$_{12-18}$, 140 µM dATP, and 0.22 µM [$^3$H]TTP (specific activity 78.0 Ci/mmol, equivalent to 17,300 cpm/pmol; NEN Research Products, Boston, Mass.), was added to each well. The sample (20 µl) was added to the reaction mixture which was then incubated at 37° C. for 2 hours. The reaction was terminated by the addition of 100 µl 10% trichloroacetic acid (TCA) containing 0.45 mM sodium pyrophosphate. The acid-insoluble nucleic acids which precipitated were collected on glass filters using a Skatron semi-automatic harvester (setting 9). The filters were washed with 5% TCA and 70% ethanol, dried, and placed in scintillation vials. Four ml of scintillation fluid (Econofluor, NEN Research Products, Boston, Mass.) were added and the amount of radioactivity in each sample was determined using a Packard Tri-Carb liquid scintillation analyzer (Model 2,000CA). The results were expressed in dpm/ml of original clarified supernatant. The procedures for the anti-HIV-1 assays in PBMC described above have been published recently (see Schinazi, R. F. et al in *Antimicrob. Agents Chemother.* 32:1784–1789, December 1988).

Cytotoxicity studies

Toxicity in Vero (African Green Monkey) cells. Vero cells in growth medium (2.5 ml) were added to 25 cm$^2$ flasks (Falcon) in duplicate at a concentration equivalent to one tenth of cell confluency for each compound under test. After incubation at 37° C. in a 5% CO$_2$-95% air for 24 hr, the test compound (2× final concentration), dissolved in 2.5 ml of the growth medium was added, and two flasks were harvested immediately by decanting the medium, washing once with 3 ml of PBS, and then incubating at 37° C. for 5 minutes with 3 ml of trypsin/EDTA (0.125%/0.02%). The cells dislodged from the flask by the latter procedure are generally in clumps and are dispersed by repeated forceful pipetting of the suspension against the surface of the flask. To 1 ml of the well-dispersed cell suspension, 0.2 ml of trypan blue solution was added, and the number of cells were counted using a hemacytometer. Each day for the next 3 days, two of the remaining flasks were harvested in the manner just described for determination of cell number. (This method has previously been described—see Schinazi, R. F., Peters, J., Williams, C. C., Chance, D., and Nahmias, A. J.: Effect of combination of acyclovir, and vidarabine or its 5'-monophosphate on herpes simplex viruses in cell culture and in mice. *Antimicrob. Agents Chemother.* 22:499–507, 1982).

PBM proliferation assay.

The drugs were evaluated for their potential toxic effects on uninfected PHA-stimulated human PBM cells and also in CEM cells. The cells were cultured with and without drug for 6 days at which time aliquots were counted for cell viability as described above. Results are shown in Table VII.

Median-effect method

EC$_{50}$ and IC$_{50}$ values were obtained by analysis of the data using the median-effect equation (Chou, T. -C., and P. Talalay. 1984. Quantitative analysis of dose-effect relationships: the combined effects of multiple drugs or enzyme inhibitors. *Adv. Enz. Regul.* 22:27–55). Results are shown in Tables VII and VIII.

TABLE VII

Effect of AZT and copolymers on the growth of uninfected mitogen stimulated human peripheral blood mononuclear cells (PBMC) and Vero cells.

| Treatment | Concn. (µM) | % Growth inhibition | |
|---|---|---|---|
| | | PBMC[a] | Vero[b] |
| AZT | 0.1 | −8.9 | −1.8 |
| | 1 | −2.2 | 10.2 |
| | 10 | 5.5 | 20.7 |
| | 50 | 16.8 | 47.4 |
| | 100 | 28.4 | 66.3 |
| CRL-8133 | 1 | −5.1 | 13.7 |

TABLE VII-continued

Effect of AZT and copolymers on the growth of uninfected mitogen stimulated human peripheral blood mononuclear cells (PBMC) and Vero cells.

| Treatment | Concn. (μM) | % Growth inhibition PBMC[a] | Vero[b] |
|---|---|---|---|
|  | 10 | 7.3 | 45.3 |
|  | 100 | 82.2 | 77.5 |
|  | 200 | 88.2 | 87.4 |
| CRL-85221 | 1 | −5.1 | −13.7 |
|  | 10 | 65.1 | 27.7 |
|  | 100 | 72.2 | 100 |
|  | 200 | 88.7 | 100 |
| CRL-8143 | 1 | 1.8 | 29.8 |
|  | 10 | −8.9 | 31.2 |
|  | 100 | 56.4 | 48.1 |
|  | 200 | 73.6 | 48.8 |
| CRL-8141 | 1 | 8.3 | −29.1 |
|  | 10 | −12.4 | 6.0 |
|  | 100 | 78.9 | 59.3 |
|  | 200 | 83.3 | 65.6 |
| CRL-8131 | 1 | −2.8 | 15.1 |
|  | 10 | 16.4 | 17.9 |
|  | 100 | 83.5 | 80.4 |
|  | 200 | 86.6 | 94.4 |

[a]PBMC were counted after drug exposure for 6 days by the trypan blue exclusion method. Untreated cultures had $4.93 \times 10^5$ cells/ml.
[b]Vero cells were counted after drug exposure for 4 days. Untreated cultures had $3.56 \times 10^5$ cells/ml.

TABLE VIII

Summary of antiviral and cytotoxicity studies

| Treatment | Anti-HIV-1 in PBMC: $EC_{50}$ (μM) | Cytotoxicity: $EC_{50}$ (μM) PBMC | Vero |
|---|---|---|---|
| AZT | 0.0056 | >100 | 50.6 |
| CRL-8133 | 5.13 | 65.9 | 14.8 |
| CRL-85221 | 4.34 | 35.9 | 10.8 |
| CRL-8143 | 6.43 | 93.3 | >200 |
| CRL-8141 | 1.53 | 21.7 | 64. |
| CRL-8131 | 2.54 | 34.7 | 33.1 |

EXAMPLE XVII

Copolymers CRL-8131, CRL-8141, L103 and L123 were solubilized at 400 μg/ml in ice cold phosphate buffered saline. The cold solutions were filter sterilized on 0.22 μm filters and stored at 4° C. Each of the four compounds became soluble under these conditions.

The effects of the copolymers on macrophage phagocytosis was measured by uptake of Candida albicans. Monolayers of BALB/c mouse peritoneal macrophages were treated with the indicated copolymer for 18 hours prior to challenge with heat killed Candida albicans at a ratio of 5 yeast cells per macrophage. After one hour, the monolayers were washed to remove extracellular yeasts. The cells were then fixed, stained and the intracellular yeast bodies were counted. These results are summarized in Table IX.

TABLE IX

| Group (40 μg/ml) | % macrophages with Candida | No. Candida per macrophage |
|---|---|---|
| CRL-8131 | 41.1 (4.9) | 1.74 (0.18) |
| CRL-8141 | 41.8 (3.4) | 2.06 (0.25) |
| L103 | 31.4 (0.9) | 2.33 (0.16) |
| L123 | 57.3 (6.4) | 2.30 (0.06) |
| Control | 52.0 (2.1) | 2.09 (0.23) |

The pretreatment of macrophages with copolymers was not toxic as defined the ability of the macrophage to phagocytose particles. Giemsa staining indicated that the morphology of the macrophages was not altered.

EXAMPLE XVIII

Macrophage monolayers were pretreated with the indicated copolymers for 18 hours. The macrophages were then challenged with Toxoplasma gondii at a concentration of two T. gondii organisms per macrophage. After one hour, non-phagocytized organisms were removed by washing and the medium plus the copolymer was replenished. Monolayers were fixed and enumerated at 24 hours after challenge. As a positive control, interferon-g, IFN-g, (murine recombinant at 200 U/ml) was added to macrophage monolayers 18 hours before challenge with Toxoplasma. These macrophages are activated by the IFN-g and readily kill Toxoplasma.

TABLE X

| Group | Growth of Toxoplasma gondii |
|---|---|
| CRL-8131 | + |
| CRL-8141 | + |
| L103 | + |
| L123 | + |
| Control | +++++ |
| IFN-g | +/− |

These results showed that intracellular Toxoplasma not only did not multiply in infected macrophages over a 24 hour period, but were apparently killed and digested by the phagocytes. Although the macrophages were pretreated with the copolymer prior to challenge with the Toxoplasma, it should be noted that during the one hour challenge interval, the macrophages were washed free of the copolymer. Thus, it is unlikely that the copolymer had a direct effect on the parasites while they were extracellular.

EXAMPLE XIX

The experimental protocol is as follows: Cultured human macrophages were infected with M. avium and incubated for 7 days with and without the indicated compound. Samples of the macrophages cultures were taken at 0, 4, and 7 days after infection. The macrophages of the samples were lysed, the lysates diluted, and diluted samples of the lysates cultured on 7H10 agar plates to count viable bacteria (CFU).

The bacteria multiply progressively in unprotected macrophages. Inhibition by drugs is evident by retarded or arrested intra-macrophages bacterial multiplication, or by diminished CFU with time indicating death of intra-macrophages bacteria. In this model, there is no significant extracellular multiplication of the M. avium. Any inhibition of bacteria as measured by effects on CFU counts, thus indicated inhibition of intracellular bacteria.

Two serovars most often found associated with AIDS, and originally isolated from AIDS patients, were used. Serovar 4 strain 7497 was purposely used in mixture of phenotypes smooth-transparent (ST) and round-domed (RD). ST is the virulent phenotype and multiplies progressively in macrophages; RD usually do not multiply and may be killed by the macrophages and thus are the avirulent phenotype. Serovar 8 strain T-138 was a highly virulent, pure, ST phenotype.

Each experiment had a negative control group without drug. Other groups had copolymers added once, immediately after infection, usually at three different concentrations ($10^{-4}$, $10^{-5}$ and $10^{-6}$M). Each experiment also had an Anasamycin ("LSM") positive control at 1 µg/ml to demonstrate effective suppression of the *M. avium* within macrophages, and combinations of LSM and the copolymers were used to look for synergy between the two. Certain experiments had variations of these groups, or other groups. Macrophages used in these experiments were obtained from healthy volunteers.

Figure 24:
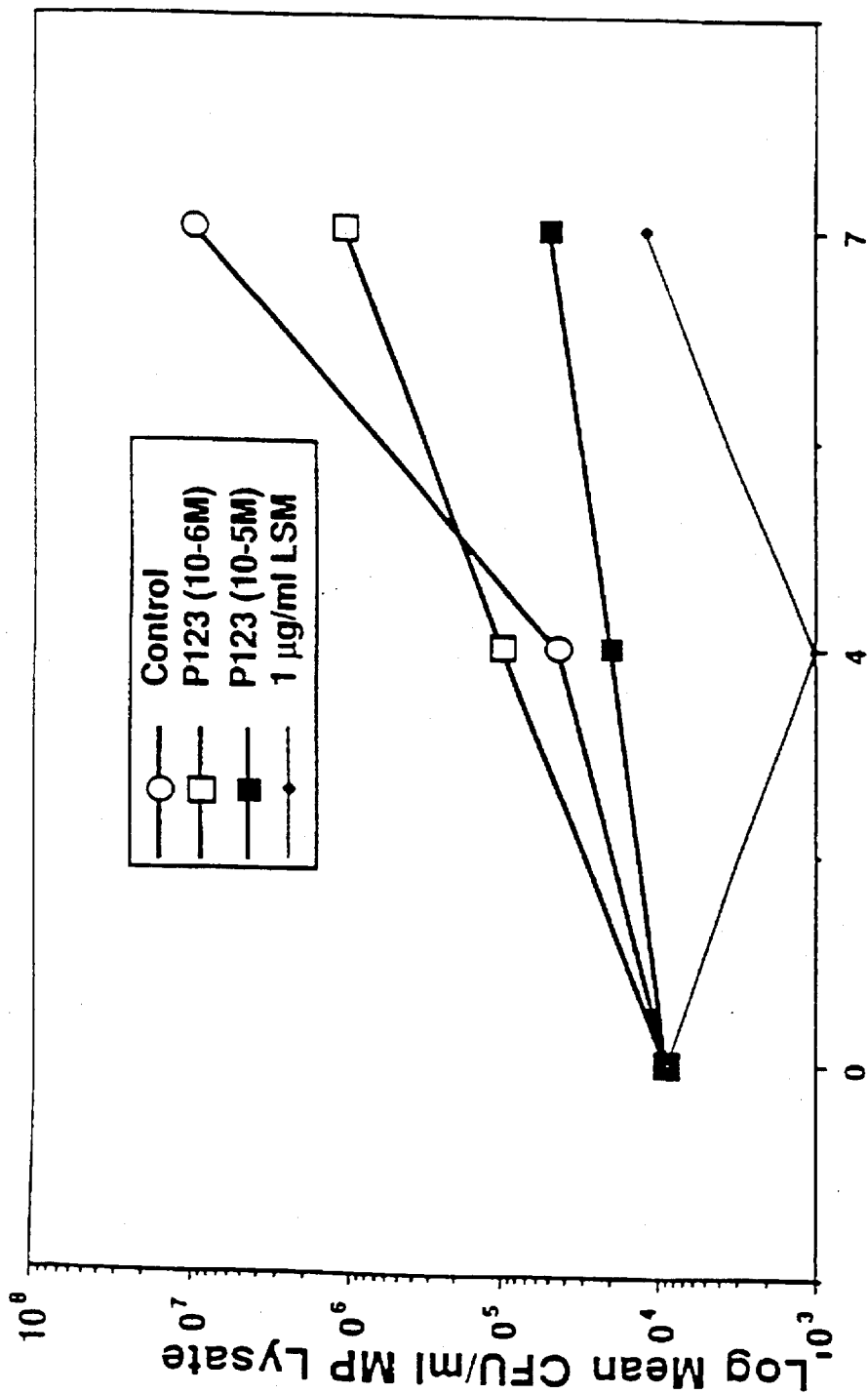
FIG. 24 is a graphical representation of the effect of CRL-8143 copolymer on the viability of intracellular *Mycobacterium avium*.

As shown in FIG. 24, the copolymer CRL-8143 significantly inhibited the growth of mycobacteria designated T-138 at a dose of $1 \times 10^{-5}$M.

EXAMPLE XX

Experiments were conducted to examine the combination of CRL-8131 and CRL-8142 with pyrimethamine, sulfadiazine or clindamycin for in vivo activity against *Toxoplasma gondii*. CRL-8131 was combined with two percent Tween 80 and 1 percent ethanol, and CRL-8142 was combined with one percent Tween 80 and 5 percent ethanol. A series of experiments were conducted with mice infected either by intraperitoneal (IP) injection of tachyzoites of the R. H. strain or orally with cysts of C56 strain.
Methods
Intraperitoneal Infection Mice were Swiss-Webster females weighing 20 grams at the beginning of the experiment. Infection was IP with $10^3$ tachyzoites. Treatment with CRL-8131 or CRL-8142 alone was administered intraperitoneally. Doses of 25 (CRL-8131) or 25 or 50 (CRL-8142) mg/kg/day were used. When these compounds were used in combination with pyrimethamine, sulfadiazine or clindamycin they were administered IP and the antibiotic was administered orally by gavage or in the drinking water. Pyrimethamine was used at 10 mg/kg/day, sulfadiazine at 80 mg/L drinking water and clindamycin at 150 mg/kg/day.

Figure 29:
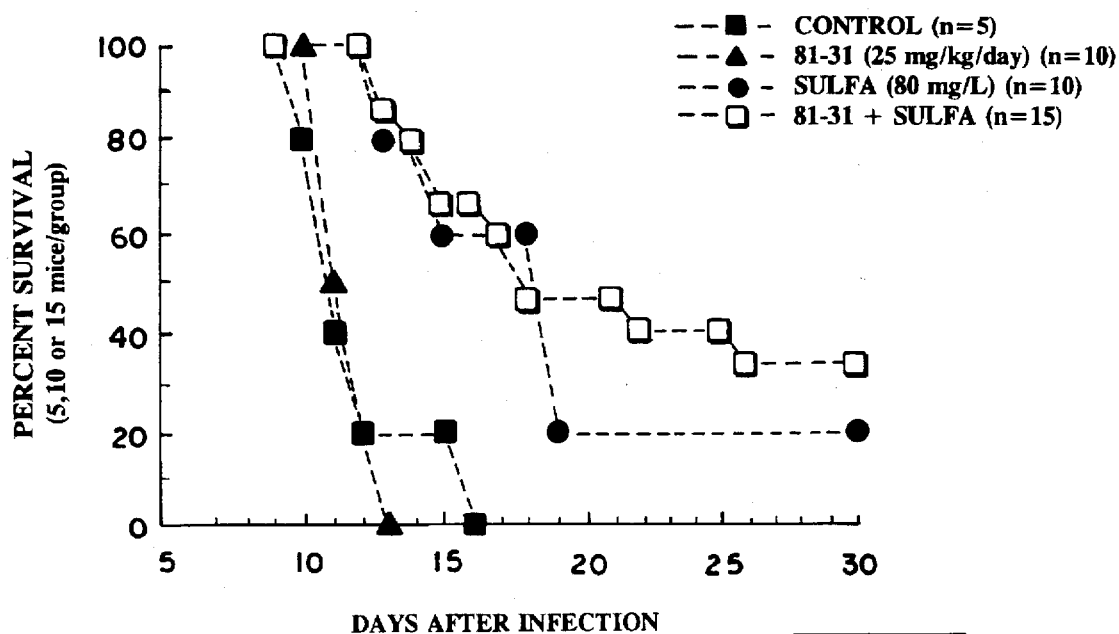
FIG. 29 is a graphical representation of the activity of CRL-8131 plus sulfadiazine in mice infected orally with cysts of the C56 strain of *T. gondii*.
Figure 30:
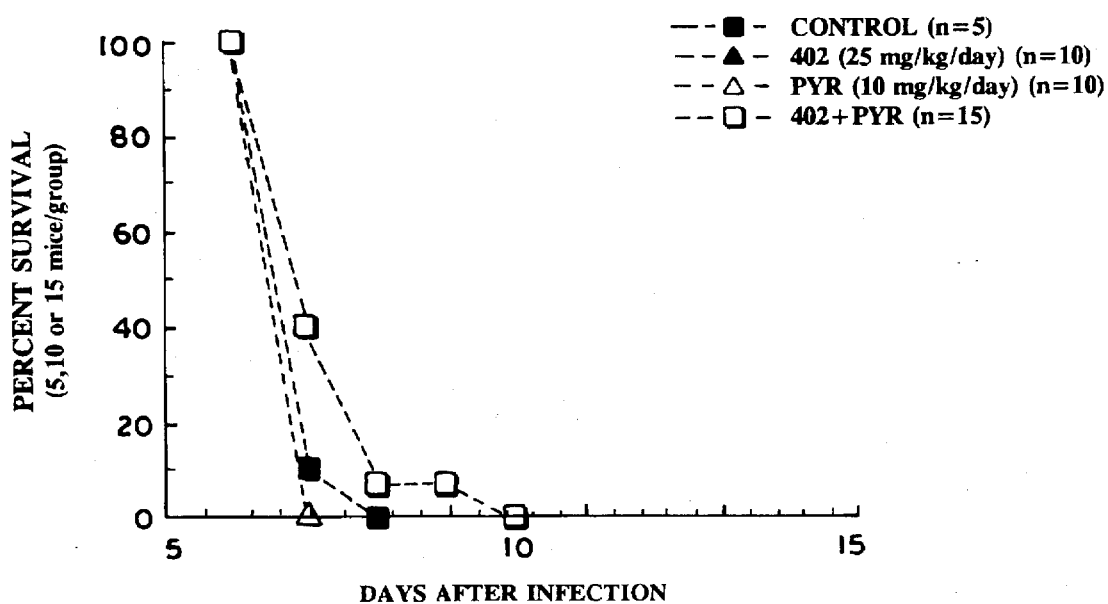
FIG. 30 is a graphical representation of the activity of CRL-8142 plus pyrimethamine in mice infected intraperitoneally with tachyzoites of strain RH of *T. gondii*.

Treatment was initiated 24 hours after infection and continued for 10 days. Mice dying during treatment and after its discontinuation were examined for presence of *T. gondii* tachyzoites in intraperitoneal fluid.
Oral infection Mice were as above and an infection was with 10 cysts of the C56 strain of *T. gondii* administered orally by gavage. Treatment with the copolymers alone was administered IP at the doses described above. When combinations were used the copolymers was administered IP and the other drugs, at the concentrations described above, orally by gavage or in the drinking water. Treatment was initiated three days after infection and continued for ten days. Mice were examined for presence of *T. gondii* as above.
Results Survival in mice infected intraperitoneally with tachyzoites of the RH strain of *T. gondii* was considerably increased following treatment when 25 mg/kg/day of CRL-8131 in combination with each one of the other drugs (FIGS. 25–27). However, in mice infected orally with tissue cysts there was no significant increase in survival (FIGS. 28 and 29). CRL-8142 was not as effective in mice infected intraperitoneally with RH *T. gondii* when used at the same dose as CRL-8131 (FIGS. 30 and 31). However, significant prolongation in time to death was noted when the concentration of CRL-8142 was increased to 50 mg/kg/day (FIG. 32). Unexpectedly, the combination of this concentration of CRL-8142 with clindamycin resulted in 100 percent survival of infected mice (FIG. 32).

Combination of a dose of 25 mg/kg/day of CRL-8142 with each one of the other drugs did not reveal any activity against oral infection with cysts of C56 strain of *T. gondii* (FIGS. 33 and 34).

EXAMPLE XXI

Figure 35:
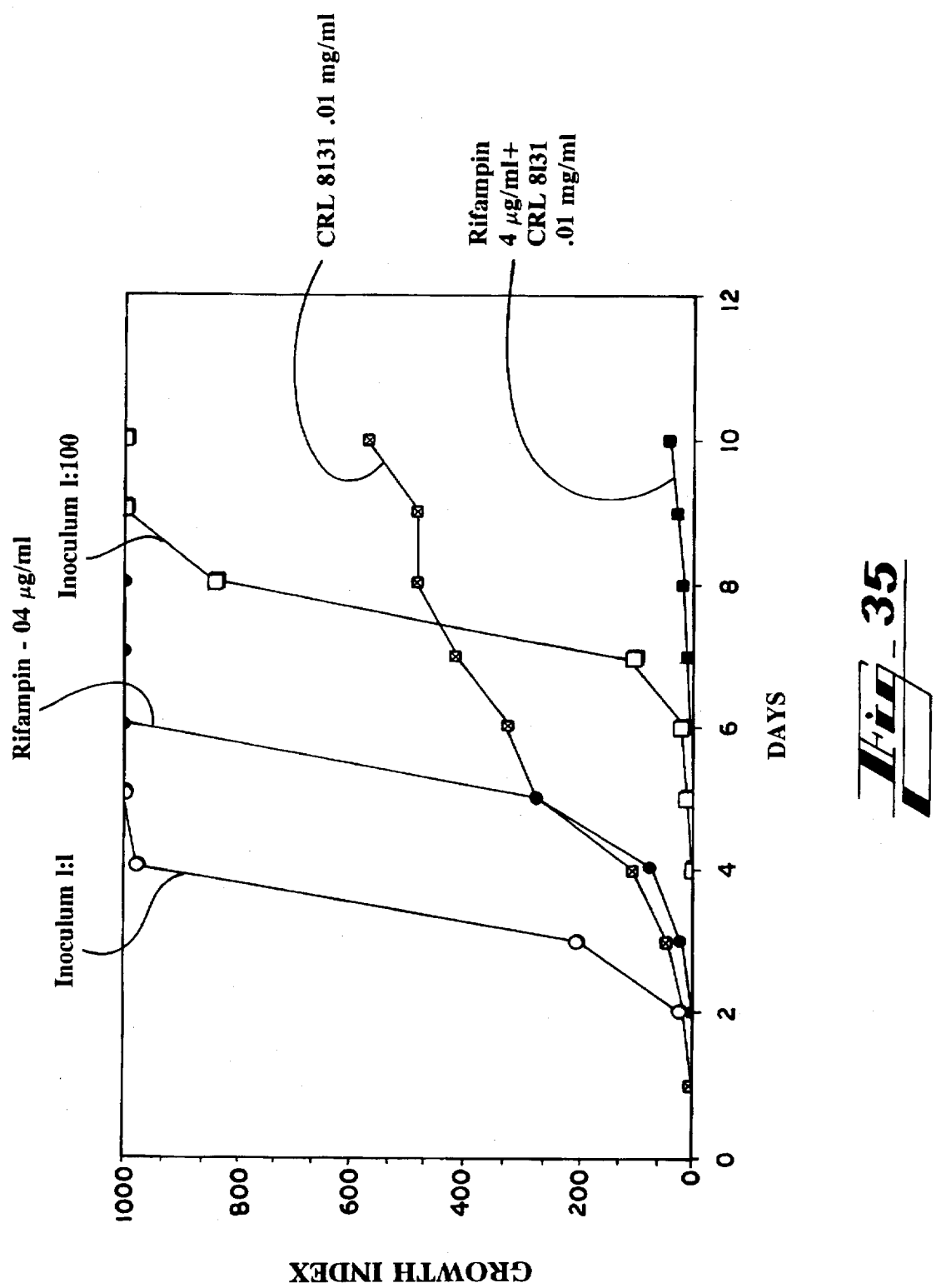
FIG. 35 is a graphic illustration of the synergistic effect of poloxamer formulation CRL-8131 in combination with rifampin.

Growth studies as described above in Example XII were conducted to study the effect of rifampin alone, CRL-8131 alone, and a combination of rifampin and CRL-8131. Rifampin at a concentration of 0.04 µg/ml was effective in inhibiting growth of *M. avium* as was CRL-8131 at a concentration of 0.01 mg/ml. The combination of rifampin and CRL-8131 at these concentrations, however, unexpectedly and dramatically inhibited growth, and provided almost 100% protection. Results are shown in FIG. 35.

EXAMPLE XXII

A therapeutic delivery vehicle is prepared by combining any of the antiinfective copolymers, such as CRL-8131 with any of a variety of antimicrobial agents, such as streptomycin. For CRL-8131 a concentration of three to five percent weight per volume is desirable to construct the therapeutic vehicle. For more hydrophilic copolymer a five to ten percent weight per volume.

300 milligrams of CRL-8131 was added to 10 ml of 0.9% NaCl and the mixture is solubilized by storage at temperatures of 2°–4° C. until a clear solution is formed. 3.0 grams of streptomycin is added to the clear poloxamer solution and mixed thoroughly until the streptomycin is in solution. The final concentration of streptomycin and copolymer in the mixture is 30% weight per volume and 3% weight per volume, respectively.

Micelles associating the copolymer and streptomycin are formed by raising the temperature above 5° C. and allowing the suspension of micelles to equilibrate. The equilibrated suspension is suitable for administration.

It should be understood that the foregoing relates only to a preferred embodiment of the present invention and that numerous modifications or alterations may be made therein without departing from the spirit and the scope of the invention as set forth in the appended claims.

We claim:

1. A method for treating an infection in a human or animal caused by a microorganism, comprising:

administering to the human or animal an effective amount of a therapeutic drug and a surface-active copolymer comprising a polyoxypropylene/polyoxyethylene block copolymer with the following general formula:

wherein "a" is an integer such that the polypropyleneoxide hydrophobe represented by ($C_3H_6O$) has a molecular weight of approximately 1,200 to 15,000 Daltons, and "b" is an integer such that the polyethyleneoxide hydrophile portion represented by ($C_2H_4O$) constitutes approximately 1% to approximately 50% by weight of the copolymer, and the polydispersity value of the copolymer is less than approximately 1.17.

2. The method of claim 1, wherein "a" is an integer such that the polypropyleneoxide hydrophobe represented by ($C_3H_6O$) has a molecular weight of approximately 3,250 Daltons, and "b" is an integer such that the polyethyleneoxide hydrophile portion represented by ($C_2H_4O$) constitutes approximately 10% by weight of the total molecular weight of the copolymer, and the polydispersity value of the copolymer is less than approximately 1.17.

3. The method of claim 1, wherein the therapeutic drug is selected from the group consisting of rifampin, isoniazid, ethambutol, gentamicin, tetracycline, erythromycin, pyrazinamide, streptomycin, clofazimine, rifabutin, fluoroquinolones, ofloxacin, sparfloxacin, azithromycin, clarithromycin, dapsone, doxycyline, ciprofloxacin, ampicillin, amphotericin B, fluconazole, ketoconazole, ciprofloxacin, fluconazole, pyrimethamine, sulfadiazine, clindamycin, azithromycin, paromycin, diclazaril, clarithromycin, atovaquone, pentamidine, acyclovir, ribavirin, trifluorouridine, AZT, DDI, DDC, foscornat, ganciclovir, and antisense oligonucleotides.

4. The method of claim 1, wherein the therapeutic drug comprises a mixture of several antibiotics.

5. The method of claim 1, further comprising approximately 0.1% to approximately 5% by weight of a surfactant, and approximately 0.5% to approximately 5% by volume of a low molecular weight alcohol.

6. The method of claim 5, wherein the surfactant is polyoxyethylenesorbitan monooleate and the alcohol is ethanol.

7. The method of claim 1, wherein the microorganism is a bacteria.

8. The method of claim 7, wherein the bacteria is selected from the group consisting of *Mycobacterium tuberculosis, Mycobacterium avium, Mycobacterium leprae, Chlamydia trachomatis, Chlamydia pneumoniae, Chlamydia psittaei, Toxoplasma gondii* and *Listeria monocytogenes*.

9. The method of claim 1, wherein the microorganism is a virus.

10. The method of claim 9, wherein the virus is HIV or herpes or antigenically-related strains thereof.

11. The method of claim 1, wherein the microorganism is a fungus.

12. The method of claim 11, wherein the fungus is a Candida species.

13. The method of claim 12, wherein the Candida species is *Candida albicans*.

14. The method of claim 1, wherein the administration of the copolymer and the administration of the therapeutic drug are selected from the group consisting of injection, intravenous, intramuscular, topical, transdermal, inhalation, trans-mucosal, oral ingestion, or a plurality of modes of administration.

15. The method of claim 1, wherein the therapeutic drug is admixed with the copolymer.

16. A method of treating a human or animal with an infection caused by an intracellular pathogen, comprising the step of: administering to the human or animal an effective amount of a therapeutic drug and a surface-active copolymer comprising a polyoxypropylene/polyoxyethylene block copolymer with the following general formula:

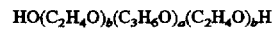

wherein "a" is an integer such that the polypropyleneoxide hydrophobe represented by ($C_3H_6O$) has a molecular weight of approximately 1,200 to 15,000 Daltons, and "b" is an integer such that the polyethyleneoxide hydrophile portion represented by ($C_2H_4O$) constitutes approximately 1% to approximately 50% by weight of the copolymer, and the polydispersity value of the copolymer is less than approximately 1.17.

17. The method of claim 1 wherein the microorganism is a protozoa.

* * * * *